(12) United States Patent
Hiroaki et al.

(10) Patent No.: US 8,415,146 B2
(45) Date of Patent: Apr. 9, 2013

(54) VECTOR AND UTILIZATION OF THE SAME

(75) Inventors: Hidekazu Hiroaki, Yokohama (JP);
Takeshi Tenno, Yokohama (JP);
Natsuko Goda, Yokohama (JP)

(73) Assignee: Yokohama City University, Kanagawa (JP)

( * ) Notice: Subject to any disclaimer, the term of this patent is extended or adjusted under 35 U.S.C. 154(b) by 0 days.

(21) Appl. No.: 10/570,511

(22) PCT Filed: Aug. 31, 2004

(86) PCT No.: PCT/JP2004/012523
§ 371 (c)(1),
(2), (4) Date: Feb. 28, 2006

(87) PCT Pub. No.: WO2005/021747
PCT Pub. Date: Mar. 10, 2005

(65) Prior Publication Data
US 2008/0102448 A1    May 1, 2008

(30) Foreign Application Priority Data

Sep. 1, 2003 (JP) ................................. 2003-308773

(51) Int. Cl.
*C12N 15/00* (2006.01)
*C12N 15/70* (2006.01)
*C12N 15/72* (2006.01)

(52) U.S. Cl.
USPC ....................... 435/320.1; 435/6.1; 435/252.3

(58) Field of Classification Search .......................... None
See application file for complete search history.

(56) References Cited

PUBLICATIONS

Goda et al. (Published Mar. 2004, Protein Science, vol. 13, No. 3, pp. 652-658).*
Jeung et al. (2002) Plasmid, vol. 48, pp. 160-163.*
Noriko Arashi-Heese et al. Molecular Biotechnology, vol. 12, 1999, pp. 281-283.*
http://tools.neb.com/NEBcutter2-Xcml_restriction sites 1.*
http://tools.neb.com/NEBcutter2-Xcml_restriction sites 2.*
BsoB fact sheet: NEB website: http://www.neb.com/nebecomm/products/productR0586.asp.*
Supplementary European Search Report forPCT/JP2004012523 mailed Nov. 8, 2006.
Goda, N. et al, The PRESAT-vector: Asymmetric T-vector for high-throughput screening of soluble protein domains for structural proteomics, Protein Science (2004), 13:652-658. Published by Cold Spring Harbor Laboratory Press.
Jeung, J. U., et al., Construction of two pGEM-7Zf(+) phagemid T-tail vectors using Ahdl-restriction Endonuclease sites for direct cloning of PCR products, Plasmid 48 (2002) 160-163.
Zhou, M et al., Universal TA Cloning, Current Issues Mo. Biol. (2000) 2(1): 1-7.
WO 01/07633 A1 (The United States of America), Feb. 1, 2001, & US 6,184,000 B1.
Siegal, M.L. et al., Triple-ligation strategy with advantages over directional cloning., Biotechniques, vol. 21, No. 4, pp. 614, 616, 618 to 619 (1996).
Yang, Y.S. et al., Directional cloning of an oligonucleotide fragment into a single restriction site., J. Immunol. Methods, vol. 181, No. 1, pp. 137 to 140 (1995).
English Translation of the International Preliminary Report on Patentability for International application PCT/JP2004/012523 mailed Jun. 29, 2006.

* cited by examiner

*Primary Examiner* — Janet Epps-Smith
(74) *Attorney, Agent, or Firm* — DLA Piper LLP (US)

(57) ABSTRACT

The present invention provides a tool for reducing the time and labor required for obtaining a protein by recombinant expression of a gene in a host.
A vector characterized by having two restriction recognition sequences different in nucleotide sequence both of which are recognized by a first restriction enzyme, one of the restriction recognition sequences comprising a part of a restriction recognition sequence recognized by a second restriction enzyme that is different from the first restriction enzyme, and the other one of the restriction recognition sequences not comprising the part of the restriction recognition sequence recognized by the second restriction enzyme. A method of producing a protein and/or a protein domain, using the above-described vector.

12 Claims, 7 Drawing Sheets

VECTOR AND UTILIZATION OF THE SAME

TECHNICAL FIELD

The present invention relates to a novel vector and use thereof.

BACKGROUND ART

Technology to obtain protein materials by recombinant expression of various gene products simultaneously and in parallel using *Escherichia coli* is very important in the scientific field of structural proteomics/functional proteomics which is generally called post-genomics.

In order to obtain a protein sample from a gene of interest, conventionally, the gene of interest was amplified by PCR; the resultant PCR product was ligated into a sub-cloning vector, with which a host was transformed; the transformed host was allowed to form single colonies; plasmid was purified from the host derived from each colony; the nucleotide sequence of the plasmid was determined to thereby select those clones in which the gene of interest was inserted. Subsequently, a DNA fragment containing the gene of interest was cleaved out from the selected clone using restriction enzymes; the cleaved DNA fragment was purified and then integrated into a fusion protein expression vector; a host was transformed with the vector; the transformed host was allowed to form single colonies; plasmid was purified from the host derived from each colony; a host bacteria for protein expression was transformed with the purified plasmid to thereby express the protein encoded by the gene of interest. The above-described operations are time-consuming; they require nine days at the quickest. Besides, the step of cleaving DNA fragments containing the gene of interest from the sub-cloning vector using restriction enzymes and the step of purifying the resultant DNA fragments require skill.

DISCLOSURE OF THE INVENTION

Problem for Solution by the Invention

It is an object of the invention to provide a tool for reducing the time and labor required for obtaining a protein by recombinant expression of a gene in a host.

It is another object of the invention to provide a method of producing a protein encoded by a gene using the above-mentioned tool.

Means to Solve the Problem

It is known that most representative enzymes used in PCR, such as Taq DNA polymerase/Tth DNA polymerase, has an activity of a side reaction of adding an extra residue dA to the 3' end of the amplified DNA product in a template independent manner. Therefore, most of the double-stranded DNA fragments amplified by PCR have a 3'-overhang structure in which one dA residue is added.

When a plasmid vector having a 3'-dT overhang that will form a complementary base pair with dA is prepared and mixed with the PCR-amplified product described above, base pair formation utilizing the one-base overhangs readily occurs. When DNA ligase is added thereto, ligation between the vector and the PCR amplified product occurs. Since DNA ligase does not cause ligation between mismatch-containing DNA ends, it is known that self-ligation of plasmid vector alone without the PCR amplified product hardly occurs.

A method in which an open circular vector having a 3'-dT overhang structure (T-vector) is prepared in advance and then a PCR product is mixed for ligation without restriction enzyme treatment or blunt-ending treatment utilizing the above-described nature is called TA-cloning.

Methods for preparing T-vector are classified into three according to their principles.

The first method uses TdT. TdT (terminal deoxinucleotidyltransferase) is an enzyme which adds any deoxynucleotide to DNA ends in a template independent manner. Therefore, when a plasmid is first digested with a blunt-end restriction enzyme and then treated with TdT in the presence of dTTP, a vector in which one to several dT's are added to its 3' end can be prepared. However, it seems that no report of T-vector preparation by this method has been made efficiently.

The second method uses the TdT activity of Taq DNA polymerase. As described above, Taq DNA polymerase adds one molecule of dA to the blunt end of DNA in PCR reaction solution. However, when Taq is reacted with the blunt end of DNA in the presence of excessive $Mg^{2+}$ and in the presence of dTTP alone without other dNTPs, one residue of dT is added to DNA. Therefore, it is possible to prepare T-vector utilizing this nature. Briefly, a vector having one dT added to its 3' end can be prepared by digesting a plasmid with a blunt-end restriction enzyme and then reacting the digested plasmid with Taq in the presence of dTTP and $Mg^{2+}$. In this method, it seems that the T-overhang generation efficiency varies remarkably depending on the recognition sequence of the blunt-end restriction enzyme used. EcoRV is used in most of the preparation examples reported so far, whereas it is known that the generation efficiency is low when SmaI is used. Methods for avoiding this are disclosed on the internet.

The third method is a method in which a "cassette" DNA sequence containing two restriction enzyme sites directly generating T-overhangs is designed and digested with a relevant restriction enzyme. As an example in which a restriction enzyme capable of generating a single 3'-T overhang is used in an actual T-vector, use of XcmI, Eam11051 and AhdI is reported. According to this method, the above-described "cassette" DNA sequence containing two restriction enzyme sites is designed and inserted into a plasmid of interest. Then, the plasmid is digested with a relevant restriction enzyme. As a result, an open circular plasmid having a dT-overhang at both ends is prepared. (This time, the present inventors used AhdI to prepare a T-vector. With this method, it is possible to design an open circular plasmid having "asymmetric" dT-overhangs. Besides, almost 100% of the open circular plasmids obtained by this method are expected to have a dT-overhang at both ends. Thus, the plasmid is of extremely high quality.)

However, conventional TA-cloning has a drawback that this method cannot control the orientation of a gene of interest inserted into the vector. As a result, most of those plasmids prepared as T-vector have been mainly applied only as (1) a vector for cloning (or sub-cloning) unknown genes or (2) a vector for cloning genes having novel promoter activity. There have been only a small number of T-vectors which are used for TA-cloning of a region to be expressed as a protein (ORF) into an expression vector directly. In the above-described two uses, the orientation of ORF does not matter. The orientation of ORF only matters when conducting protein expression experiments. (This time, in order to select those plasmids in which a foreign gene (PCR product) is inserted in the proper orientation easily, the present inventors designed a sequence in such a manner that the restriction sequence of restriction enzyme NcoI or NdeI appears only when the foreign gene is inserted in the opposite direction. As a result, it becomes possible to selectively transform only those plasmids which express a fusion protein linked to such as glutathione-5-transferase [GST] in the proper orientation into *Escherichia coli*.)

Vectors for expressing a foreign gene as a GST fusion protein in *E. coli* have been commercialized. PGEX series vectors which are provided with protease recognition and cleavage sequence with multicloning site following the coding region of *Schistosoma japonicum*-derived GST are sold by Amersham Pharmacia Biotech. Because GST-fusion proteins are relatively high in solubility and expressed at high levels in *E. coli*; the protein can be purified in almost one step when affinity chromatography using glutathione-immobilized carrier (beads) is employed; interactions between a fusion protein of interest immobilized on glutathione beads and its target molecule (protein, nucleic acid, low molecular weight molecule, etc.) can be observed easily (pull-down assay); compared to proteins without tag, functions of GST-fusion proteins are less damaged when immobilized on a measuring chip for molecular interaction experiments by surface plasmon resonance; the vecors of this series are used very widely in biochemistry and molecular biology as an expression vector. The inventors considered it will be very useful to prepare a number of expression systems in parallel, each of which expresses various proteins and protein fragments of various lengths, by modifying the pGEX series vector into a TA-vector.

After the completion of genome projects, in order to identify functional proteins and functional domains of proteins and to apply the results in industries, it has become important to perform both determination of tertiary structures and determination of molecular functions at high speed. For that purpose, it is necessary to obtain protein samples retaining their activities which may be used for a series of experiments in the form of soluble proteins. Generally, when a full-length or a part of a gene encoding a protein derived from human, mammal or plant is expressed in *E. coli*, the protein often becomes insoluble and makes it very difficult to prepare samples for structural/functional analyses. In such cases, it is known that changing the region/length to be expressed as a protein (this technique is called domain mapping or domainization) or introducing one or several site-specific mutations of amino acids improves the solubility dramatically. The same techniques are also used on a protein obtained as a soluble protein, in the process of preparing NMR samples for determination of its tertiary structure, or in the process of improving its solubility for crystallization or its crystallizing property. Among these processes, the process of obtaining many types of gene fragments in a short period of time and at low cost has become possible to achieve due to advances in PCR and reduced prices of synthesized PCR primers. Therefore, the current technical problems are human and time costs for preparing expression vectors, and methods for promptly discriminating whether the protein of interest is soluble or not. The advantage of using GST-fusion proteins for this purpose is that the following procedures are possible: after separating *E. coli* extract containing a GST-fusion protein into soluble and insoluble fractions by centrifugation, the amount of the GST-fusion protein can be measured by calorimetric assay utilizing the enzyme activity of GST as an indicator in the mixture of *E. coli* and crude protein. For example, it is possible to colorimetrically determine the amount of the GST-fusion protein on 96-well plates in parallel and in a short period of time.

Considering what have been described above, the inventors have tried the following.

1. Trial generation of GST-T vector was carried out by the above-described method using "SmaI/Taq". Although a GST-T vector was obtained, it lacked reproducibility and its efficiency in PCR product sub-cloning was low. Thus, it was not practical.

2. Methods for improving the efficiency when SmaI/Taq are used were obtained from documents on the internet and tested. However, no improvement was recognized.

3. The inventors considered that the nucleotide sequence of the blunt end digested by SmaI may be the reason for the low efficiency, and tested a unique improvement method in which the cohesive end generated by BamHI digestion was blunt-ended with Klenow fragment and then dT is attached with Taq. However, the efficiency was not improved.

4. Strategy was changed to the above-described "method of using a restriction enzyme cassette". As the restriction enzyme, AhdI was selected.

5. It was found that when AhdI is reacted with antibiotic-resistant plasmids [not only pGEX-2T/pGEX-4T3 (GST-fusion vectors)], the ampicillin resistance gene of the plasmids is cleaved. Then, the inventors modified pGEX-4T3 in which the AhdI restriction site contained in ampicillin resistance gene was mutated by introducing a silent, site-directed mutation. (The sequence of the primer (Anti AhdI) used for the site-directed mutagenesis is shown in SEQ ID NO: 21 of the sequence listing.)

6. An AhdI-linker was prepared. Briefly, using PCR primers of SEQ ID NOS: 22 and 23 and a derivative pET32aPACAP from pET32a (Novagen) as a template, PCR was performed to thereby obtain an approximately 500 bp fragment. This fragment was integrated into an existing TA-vector (this time, pGEM-T from Promega was used) by conventional methods, followed by confirmation of the sequence and amplification of the appropriate clone. A purified plasmid was obtained. Then, the plasmid was digested with BamHI to thereby obtain AhdI linker (approx. 500 bp).

7. A vector to be used as the base for GST-T vector (i.e., TA-vector using GST-fusion) was prepared. Briefly, the mutant of pGEX-4T3 obtained in paragraph 5 above was amplified and digested with BamHI. The AhdI linker obtained in paragraph 6 above was ligated into that BamHI site. Appropriately prepared clones were isolated and amplified. The AhdI linker at this stage has no orientation (the linker may be inserted in either direction).

8. GST-T vector was prepared. Briefly, the vector prepared in paragraph 7 above was digested with AhdI to obtain an open circular plasmid, which was then separated and purified using agarose gel. Since the resultant vector has a 3'-dT overhang, it may be used in conventional TA-cloning.

9. An AhdI linker applicable to NcoI ORF selection was prepared. In NcoI ORF selection, those vectors (e.g., plasmids) having a foreign gene inserted in the opposite orientation are digested when treated with NcoI; and hosts harboring such vectors cannot grow. As a result, only those hosts harboring vectors having a foreign gene inserted in the proper orientation can be selected. The method of preparation of this linker is the same as described in paragraph 6 above except that a combination of SEQ ID NOS: 22 and 24 was used as primers. The sequences of the thus prepared AhdI linker applicable to NcoI ORF selection are shown in SEQ ID NOS: 26 and 27. A DNA strand having the sequence of SEQ ID NO: 26 is associated with a DNA strand having the sequence of SEQ ID NO: 27 to form a double-stranded DNA that is the AhdI linker.

10. dGST-T vector applicable to NcoI ORF selection (directional GST-T vector; this means a GST-T vector capable of selecting the orientation of ORF) was prepared. The method of preparation is the same as described in paragraphs 7 and 8 above. However, at the time of sequence confirmation as described in paragraph 7, those vectors in which the sequence corresponding to the primer sequence of SEQ ID NO: 22 at the fusion site with GST is located proximal to the coding region of GST (GST side) were selected to thereby obtain closed circular vectors to be used as the base for the vector capable of NcoI ORF selection. This closed circular vector was also capable of NdeI ORF selection when the design of PCR primers for amplifying the inserted foreign gene was changed; in NdeI ORF selection, vectors (e.g., plasmids) having a foreign gene inserted in the opposite orientation are digested not with NcoI but with NdeI; hosts harboring such vectors cannot grow; as a result, only those hosts harboring vectors having a foreign gene inserted in the proper orientation can be selected.

The present invention has been achieved based on the above-described experimental procedures and results.

The first invention of the present patent application provides a vector having two restriction recognition sequences different in nucleotide sequence which are recognized by a first restriction enzyme, wherein one of the restriction recognition sequences comprises a part of a restriction recognition sequence recognized by a second restriction enzyme that is different from the first restriction enzyme, and the other one of the first restriction recognition sequences does not comprise the part of the restriction recognition sequence recognized by the second restriction enzyme.

The first restriction enzyme may be a restriction enzyme that produces a 3'-overhang in the digested DNA. As a specific example of the base at the 3'-overhang, thymine may be given.

The first restriction enzyme may be selected from the group consisting of AhdI or an isoschizomer thereof, XcmI or an isoschizomer thereof, or a combination thereof.

When the first restriction enzyme is AhdI or an isoschizomer thereof, it is preferred that one of the two restriction recognition sequences different in nucleotide sequence which are recognized by AhdI be represented by the following sequences (I) and (II), and that the other one be represented by the following sequences (III) and (IV).

| | | |
|---|---|---|
| 5'-GACX$^{1a}$X$^{2a}$TX$^{3a}$X$^{4a}$GTC-3' | (I) | (SEQ ID NO: 1) |
| 3'-CTGX$^{1b}$X$^{2b}$AX$^{3b}$X$^{4b}$CAG-5' | (II) | (SEQ ID NO: 2) |
| 5'-GACX$^{5a}$X$^{6a}$AX$^{7a}$X$^{8a}$GTC-3' | (III) | (SEQ ID NO: 3) |
| 3'-CTGX$^{5b}$X$^{6b}$TX$^{7b}$X$^{8b}$CAG-5' | (IV) | (SEQ ID NO: 4) |

(in sequences (I) to (IV), G is guanine, A is adenine, C is cytosine, and T is thymine;
$X^{1a}$ to $X^{8a}$ and $X^{1b}$ to $X^{8b}$ are each independently any base selected from guanine, adenine, cytosine or thymine; $X^{1a}$ and $X^{1b}$ are bases capable of forming a base pair with each other, $X^{2a}$ and $X^{2b}$ are bases capable of forming a base pair with each other, $X^{3a}$ and $X^{3b}$ are bases capable of forming a base pair with each other, $X^{4a}$ and $X^{4b}$ are bases capable of forming a base pair with each other, $X^{5a}$ and $X^{5b}$ are bases capable of forming a base pair with each other, $X^{6a}$ and $X^{6b}$ are bases capable of forming a base pair with each other, $X^{7a}$ and $X^{7b}$ are bases capable of forming a base pair with each other, $X^{8a}$ and $X^{8b}$ are bases capable of forming a base pair with each other;

sequence $CX^{1a}X^{2a}T$ is a nucleotide sequence comprising a partial sequence on 5' side of the restriction recognition sequence of the second restriction enzyme;
sequence $CX^{8b}X^{7b}T$ is a nucleotide sequence not comprising the partial sequence of the restriction recognition sequence of the second restriction enzyme that is included in sequence $CX^{1a}X^{2a}T$; and 5'- and 3'-represent the individual termini of the double-stranded DNA.)

When the first restriction enzyme is XcmI or an isoschizomer thereof, it is preferred that one of the two restriction recognition sequences different in nucleotide sequence which are recognized by XcmI be represented by the following sequences (V) and (VI), and that the other one be represented by the following sequences (VII) and (VIII).

| | | |
|---|---|---|
| 5'-CCAY$^{1a}$Y$^{2a}$Y$^{3a}$Y$^{4a}$TY$^{5a}$Y$^{6a}$Y$^{7a}$Y$^{8a}$TGG-3' | (V) | (SEQ ID NO: 5) |
| 3'-GGTY$^{1b}$Y$^{2b}$Y$^{3b}$Y$^{4b}$AY$^{5b}$Y$^{6b}$Y$^{7b}$Y$^{8b}$ACC-5' | (VI) | (SEQ ID NO: 6) |
| 5'-CCAY$^{9a}$Y$^{10a}$Y$^{11a}$Y$^{12a}$AY$^{13a}$Y$^{14a}$Y$^{15a}$Y$^{16a}$TGG-3' | (VII) | (SEQ ID NO: 7) |
| 3'-GGTY$^{9b}$Y$^{10b}$Y$^{11b}$Y$^{12b}$TY$^{13b}$Y$^{14b}$Y$^{15b}$Y$^{16b}$ACC-5' | (VIII) | (SEQ ID NO: 8) |

(in sequences (V) to (VIII), G is guanine, A is adenine, C is cytosine, and T is thymine;
$Y^{1a}$ to $Y^{16a}$ and $Y^{1b}$ to $Y^{16b}$ are each independently any base selected from guanine, adenine, cytosine or thymine; $Y^{1a}$ and $Y^{1b}$ are bases capable of forming a base pair with each other, $Y^{2a}$ and $Y^{2b}$ are bases capable of forming a base pair with each other, $Y^{3a}$ and $Y^{3b}$ are bases capable of forming a base pair with each other, $Y^{4a}$ and $Y^{4b}$ are bases capable of forming a base pair with each other, $Y^{5a}$ and $Y^{5b}$ are bases capable of forming a base pair with each other, $Y^{6a}$ and $Y^{6b}$ are bases capable of forming a base pair with each other, $Y^{7a}$ and $Y^{7b}$ are bases capable of forming a base pair with each other, $Y^{8a}$ and $Y^{8b}$ are bases capable of forming a base pair with each other, $Y^{9a}$ and $Y^{9b}$ are bases capable of forming a base pair with each other, $Y^{10a}$ and $Y^{10b}$ are bases capable of forming a base pair with each other, $Y^{11a}$ and $Y^{11b}$ are bases capable of forming a base pair with each other, $Y^{12a}$ and $Y^{12b}$ are bases capable of forming a base pair with each other, $Y^{13a}$ and $Y^{13b}$ are bases capable of forming a base pair with each other, $Y^{14a}$ and $Y^{14b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other; sequence $Y^{1a}Y^{2a}Y^{3a}Y^{4a}T$ is a nucleotide sequence comprising a partial sequence on 5' side of the restriction recognition sequence of the second restriction enzyme;
sequence $Y^{16b}Y^{15b}Y^{14b}Y^{13b}T$ is a nucleotide sequence not comprising the partial sequence of the restriction recognition sequence of the second restriction enzyme that is included in sequence $Y^{1a}Y^{2a}Y^{3a}Y^{4a}T$; and
5'- and 3'-represent the individual termini of the double-stranded DNA.)

When the first restriction enzyme is a combination of AhdI or an isoschizomer thereof and XcmI or an isoschizomer thereof, one of the two restriction recognition sequences different in nucleotide sequence which are recognized by the first restriction enzyme may be a restriction recognition sequence recognized by AhdI or the isoschizomer thereof and comprise a part of a recognition restriction sequence recognized by a second restriction enzyme that is different from AhdI or the isoschizomer; and the other one of the two restriction recognition sequences may be a restriction recognition sequence recognized by XcmI or an isoschizomer thereof and not comprise the part of the restriction recognition sequence recognized by the second restriction enzyme. The restriction recognition sequence which is recognized by AhdI or the isoschizomer and comprises a part of a recognition restriction sequence recognized by a second restriction enzyme that is different from AhdI or the isoschizomer is preferably represented by the following sequences (I) and (II). The restriction recognition sequence which is recognized by XcmI or the isoschizomer and does not comprise the part of the recognition restriction sequence recognized by the second restriction enzyme is preferably represented by the following sequences (VII) and (VIII).

5'-GACX$^{1a}$X$^{2a}$TX$^{3a}$X$^{4a}$GTC-3'    (I)    (SEQ ID NO: 1)

3'-CTGX$^{1b}$X$^{2b}$AX$^{3b}$X$^{4b}$CAG-5'    (II)    (SEQ ID NO: 2)

(in sequences (I) and (II), G is guanine, A is adenine, C is cytosine, and T is thymine;
X$^{1a}$ to X$^{4a}$ and X$^{1b}$ to X$^{4b}$ are each independently any base selected from guanine, adenine, cytosine or thymine; X$^{1a}$ and X$^{1b}$ are bases capable of forming a base pair with each other, X$^{2a}$ and X$^{2b}$ are bases capable of forming a base pair with each other, X$^{3a}$ and X$^{3b}$ are bases capable of forming a base pair with each other, X$^{4a}$ and X$^{4b}$ are bases capable of forming a base pair with each other;
sequence CX$^{1a}$X$^{2a}$T is a nucleotide sequence comprising a partial sequence on 5' side of the restriction recognition sequence of the second restriction enzyme; and
5'- and 3'-represent the individual termini of the double-stranded DNA.)

5'-CCAY$^{9a}$Y$^{10a}$Y$^{11a}$Y$^{12a}$AY$^{13a}$Y$^{14a}$Y$^{15a}$Y$^{16a}$TGG-3'    (SEQ ID NO: 7) (VII)

3'-GGTY$^{9b}$Y$^{10b}$Y$^{11b}$Y$^{12b}$TY$^{13b}$Y$^{14b}$Y$^{15b}$Y$^{16b}$ACC-5'    (SEQ ID NO: 8) (VIII)

(in sequences (VII) and (VIII), G is guanine, A is adenine, C is cytosine, and T is thymine;
Y$^{9a}$ to Y$^{16a}$ an Y$^{9b}$ to Y$^{16b}$ are each independently any base selected from guanine, adenine, cytosine or thymine; Y$^{9a}$ and Y$^{9b}$ are bases capable of forming a base pair with each other, Y$^{10a}$ and Y$^{10b}$ are bases capable of forming a base pair with each other, Y$^{11a}$ and Y$^{11b}$ are bases capable of forming a base pair with each other, Y$^{12a}$ and Y$^{12b}$ are bases capable of forming a base pair with each other, Y$^{13a}$ and Y$^{13b}$ are bases capable of forming a base pair with each other, Y$^{14a}$ and Y$^{14b}$ are bases capable of forming a base pair with each other, Y$^{15a}$ and Y$^{15b}$ are bases capable of forming a base pair with each other, Y$^{16a}$ and Y$^{16b}$ are bases capable of forming a base pair with each other; and
sequence Y$^{16b}$Y$^{15b}$Y$^{14b}$Y$^{13b}$T is a nucleotide sequence not comprising the part of the restriction recognition sequence of the second restriction enzyme that is included in sequence CX$^{1a}$X$^{2a}$T; and 5'- and 3'-represent the individual termini of the double-stranded DNA.)

When the first restriction enzyme is selected from the group consisting of AhdI or an isoschizomer thereof, XcmI or an isoschizomer thereof, or a combination thereof, the second restriction enzyme is preferably selected from the group consisting of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV and their isoschizomers.

When the first restriction enzyme is XcmI or an isoschizomer thereof, the second restriction enzyme is preferably selected from the group consisting of AflIII, BspLU11I, NspI, SphI, BspHI, BsaAI, PmaCI, SnaBI, NspBII, PvuII, BanII, HgiAI, SacI and their isoschizomers.

The two restriction recognition sequences different in nucleotide sequence which are recognized by the first restriction enzyme may be inserted into the multicloning site of the vector.

When the first restriction enzyme is AhdI or an isoschizomer thereof, it is preferred that a double-stranded DNA represented by the following sequences (IX) and (X) be inserted into the multicloning site.

5'-GACX$^{1a}$X$^{2a}$TX$^{3a}$X$^{4a}$GTC-N$^1$-GACX$^{5a}$X$^{6a}$AX$^{7a}$X$^{8a}$GTC-3'    (SEQ ID NO: 9) (IX)

3'-CTGX$^{1b}$X$^{2b}$AX$^{3b}$X$^{4b}$CAG-N$^2$-CTGX$^{5b}$X$^{6b}$TX$^{7b}$X$^{8b}$CAG-5'    (SEQ ID NO: 10) (X)

(in sequences (IX) and (X), G is guanine, A is adenine, C is cytosine, and T is thymine;
X$^{1a}$ to X$^{8a}$ and X$^{1b}$ to X$^{8b}$ are each independently any base selected from guanine, adenine, cytosine or thymine; X$^{1a}$ and X$^{1b}$ are bases capable of forming a base pair with each other, X$^{2a}$ and X$^{2b}$ are bases capable of forming a base pair with each other, X$^{3a}$ and X$^{3b}$ are bases capable of forming a base pair with each other, X$^{4a}$ and X$^{4b}$ are bases capable of forming a base pair with each other, X$^{5a}$ and X$^{5b}$ are bases capable of forming a base pair with each other, X$^{6a}$ and X$^{6b}$ are bases capable of forming a base pair with each other, X$^{7a}$ and X$^{7b}$ are bases capable of forming a base pair with each other, X$^{8a}$ and X$^{8b}$ are bases capable of forming a base pair with each other;
sequence CX$^{1a}$X$^{2a}$T is a nucleotide sequence comprising a partial sequence on 5' side of the restriction recognition sequence of the second restriction enzyme;
sequence CX$^{8b}$X$^{7b}$T is a nucleotide sequence not comprising the partial sequence of the restriction recognition sequence of the second restriction enzyme that is included in sequence CX$^{1a}$X$^{2a}$T;
5'- and 3'-represent the individual termini of the double-stranded DNA;
N$^1$ may not exist, and when it exists it is any nucleotide sequence having 1-1000 bases; and
N$^2$ may not exist, and when it exists it is a nucleotide sequence complementary to the nucleotide sequence of N$^1$.)

When the first restriction enzyme is XcmI or an isoschizomer thereof, it is preferred that a double-stranded DNA represented by the following sequences (XI) and (XII) be inserted into the multicloning site.

5'-CCAY$^{1a}$Y$^{2a}$Y$^{3a}$Y$^{4a}$TY$^{5a}$Y$^{6a}$Y$^{7a}$Y$^{8a}$TGG-N$^1$-CCAY$^{9a}$Y$^{10a}$Y$^{11a}$Y$^{12a}$AY$^{13a}$Y$^{14a}$Y$^{15a}$Y$^{16a}$TGG-3'    (SEQ ID NO: 11) (XI)

3'-GGTY$^{1b}$Y$^{2b}$Y$^{3b}$Y$^{4b}$AY$^{5b}$Y$^{6b}$Y$^{7b}$Y$^{8b}$ACC-N$^2$-GGTY$^{9b}$Y$^{10b}$Y$^{11b}$Y$^{12b}$TY$^{13b}$Y$^{14b}$Y$^{15b}$Y$^{16b}$ACC-5'    (SEQ ID NO: 12) (XII)

(in sequences (XI) and (XII), G is guanine, A is adenine, C is cytosine, and T is thymine;

$Y^{1a}$ to $Y^{16a}$ and $Y^{1b}$ to $Y^{16b}$ are each independently any base selected from guanine, adenine, cytosine or thymine; $Y^{1a}$ and $Y^{1b}$ are bases capable of forming a base pair with each other, $Y^{2a}$ and $Y^{2b}$ are bases capable of forming a base pair with each other, $Y^{3a}$ and $Y^{3b}$ are bases capable of forming a base pair with each other, $Y^{4a}$ and $Y^{4b}$ are bases capable of forming a base pair with each other, $Y^{5a}$ and $Y^{5b}$ are bases capable of forming a base pair with each other, $Y^{6a}$ and $Y^{6b}$ are bases capable of forming a base pair with each other, $Y^{7a}$ and $Y^{7b}$ are bases capable of forming a base pair with each other, $Y^{8a}$ and $Y^{8b}$ are bases capable of forming a base pair with each other, $Y^{9a}$ and $Y^{9b}$ are bases capable of forming a base pair with each other, $Y^{10a}$ and $Y^{10b}$ are bases capable of forming a base pair with each other, $Y^{11a}$ and $Y^{11b}$ are bases capable of forming a base pair with each other, $Y^{12a}$ and $Y^{12b}$ are bases capable of forming a base pair with each other, $Y^{13a}$ and $Y^{13b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other sequence $Y^{1a}Y^{2a}Y^{3a}Y^{4a}T$ is a nucleotide sequence comprising a partial sequence on 5' side of the restriction recognition sequence of the second restriction enzyme;

sequence $Y^{16b}Y^{15b}Y^{14b}Y^{13b}T$ is a nucleotide sequence not comprising the partial sequence of the restriction recognition sequence of the second restriction enzyme that is included in sequence $Y^{1a}Y^{2a}Y^{3a}Y^{4a}T$;

5'- and 3'-represent the individual termini of the double-stranded DNA;

$N^1$ may not exist, and when it exists it is any nucleotide sequence having 1-1000 bases; and $N^2$ may not exist, and when it exists it is a nucleotide sequence complementary to the nucleotide sequence of $N^1$.)

When the first restriction enzyme is a combination of AhdI or an isoschizomer thereof and XcmI or an isoschizomer thereof, it is preferred that a double-stranded DNA represented by the following sequences (XIII) and (XIV) be inserted in the multicloning site.

5'-GACX$^{1a}$X$^{2a}$TX$^{3a}$X$^{4a}$GTC-N$^1$-  (SEQ ID NO: 13)
CCAY$^{9a}$Y$^{10a}$Y$^{11a}$Y$^{12a}$AY$^{13a}$Y$^{14a}$Y$^{15a}$Y$^{16a}$TGG-3'  (XIII)

3'-CTGX$^{1b}$X$^{2b}$AX$^{3b}$X$^{4b}$CAG-N$^2$-  (SEQ ID NO: 14)
GGTY$^{9b}$Y$^{10b}$Y$^{11b}$Y$^{12b}$TY$^{13b}$Y$^{14b}$Y$^{15b}$Y$^{16b}$ACC-5'  (XIV)

(in sequences (XIII) and (XIV), G is guanine, A is adenine, C is cytosine, and T is thymine;

$X^{1a}$ to $X^{4a}$ and $X^{1b}$ to $X^{4b}$ are each independently any base selected from guanine, adenine, cytosine or thymine; $X^{1a}$ and $X^{1b}$ are bases capable of forming a base pair with each other, $X^{2a}$ and $X^{2b}$ are bases capable of forming a base pair with each other, $X^{3a}$ and $X^{3b}$ are bases capable of forming a base pair with each other, $X^{4a}$ and $X^{4b}$ are bases capable of forming a base pair with each other;

$Y^{9a}$ to $Y^{16a}$ and $Y^{9b}$ to $Y^{16b}$ are each independently any base selected from guanine, adenine, cytosine or thymine; $Y^{9a}$ and $Y^{9b}$ are bases capable of forming a base pair with each other, $Y^{10a}$ and $Y^{10b}$ are bases capable of forming a base pair with each other, $Y^{11a}$ and $Y^{11b}$ are bases capable of forming a base pair with each other, $Y^{12a}$ and $Y^{12b}$ are bases capable of forming a base pair with each other, $Y^{13a}$ and $Y^{13b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other; sequence $CX^{1a}X^{2a}T$ is a nucleotide sequence comprising a partial sequence on 5' side of the restriction recognition sequence of the second restriction enzyme;

sequence $Y^{16b}Y^{1b}Y^{14b}Y^{13b}T$ is a nucleotide sequence not comprising the partial sequence of the restriction recognition sequence of the second restriction enzyme that is included in sequence $CX^{1a}X^{2a}T$;

5'- and 3'-represent the individual termini of the double-stranded DNA;

$N^1$ may not exist, and when it exists it is any nucleotide sequence having 1-1000 bases; and $N^2$ may not exist, and when it exists it is a nucleotide sequence complementary to the nucleotide sequence of $N^1$.)

In sequences (IX) to (XIV), $N^1$ may be, for example, a sequence from a derivative which has been prepared by introducing a gene (e.g., thioredoxin gene) and an artificial gene (e.g., PACAP) into an appropriate restriction enzyme site of a commercial vector (such as pET21b or pET32a). It may be preferred that a part of the $N^1$ sequence comprise the second restriction enzyme site. In such a case, even when the purification of the open circular vector that is obtained by treating the vector of the present invention (hereinafter, sometimes referred to as the "PRESAT-vector") with the first restriction enzyme (hereinafter, sometimes referred to as the "open circular PRESAT-vector") is incomplete, "empty" PRESAT-vectors generating therefrom by self-ligation are cleaved by the second restriction enzyme digestion and, thus, do not form colonies after ORF selection. Therefore, even when the purification of the open circular PRESAT-vector is incomplete, an advantage that background is very low remains.

As a specific example of $N^1$, the following sequence may be given.

5'-CACCTGACTGACGACAGTTTTGACACGGATGTACTCAAAGCGGACGGGGCGATCCTCGT  (SEQ ID NO: 55)

CGATTTCTGGGCAGAGTGGTGCGGTCCGTGCAAAATGATCGCCCCGATTCTGGATGAAATCG

CTGACGAATATCAGGGCAAACTGACCGTTGCAAAACTGAACATCGATCAAAACCCTGGCACT

GCGCCGAAATATGGCATCCGTGGTATCCCGACTCTGCTGCTGTTCAAAAACGGTGAAGTGGC

GGCAACCAAAGTGGGTGCACTGTCTAAAGGTCAGTTGAAAGAGTTCCTCGACGCTAACCTGG

CCGGTTCTGGTTCTGGCCATATGGCTAGCCATCACCACCACCACAGCAGCGGCATTGAC

GGCCGGCATAGCGATGGCATCTTTACCGATAGCTATAGCCGCTATCGCAAACAGATGGCGGT

GAAAAAGTATCTGGCGGCGGTGCTGGGCTAATAA-3'

The sequence of SEQ ID NO: 55 is a sequence derived from pET32aPACAP (a pET32 derivative) that has been prepared by inserting both an NdeI fragment comprising pET32a-derived thioredoxin gene and an artificial gene of PACAP into the NheI site of pET21b.

In sequences (IX) to (XIV), $N^2$ is a nucleotide sequence complementary to the nucleotide sequence of $N^1$. As a specific example of $N^2$, the following sequence may be given.

```
3'-GTGGACTGACTGCTGTCAAAACTGTGCCTACATGAGTTTCGCCTGCCCCGCTAGGAGCA  (SEQ ID NO: 56)

GCTAAAGACCCGTCTCACCACGCCAGGCACGTTTTACTAGCGGGGCTAAGACCTACTTTAGC

GACTGCTTATAGTCCCGTTTGACTGGCAACGTTTTGACTTGTAGCTAGTTTTGGGACCGTGA

CGCGGCTTTATACCGTAGGCACCATAGGGCTGAGACGACGACAAGTTTTTGCCACTTCACCG

CCGTTGGTTTCACCCACGTGACACATTTCCAGTCAACTTTCTCAAGGAGCTGCGATTGGACC

GGCCAAGACCAAGACCGGTATACCGATCGGTAGTGGTGGTGGTGGTGTCGTCGCCGTAACTG

CCGGCCGTATCGCTACCGTAGAAATGGCTATCGATATCGGCGATAGCGTTTGTCTACCGCCA

CTTTTTCATAGACCGCCGCCACGACCCGATTATT-5'
```

The sequence of SEQ ID NO: 56 is complementary to the sequence of SEQ ID NO: 55.

The vector of the first invention of the present patent application may comprise the coding region of a specific protein [e.g., glutathione-S-transferase (GST) from mammal, *Schistosoma japonicum* or *Escherichia coli*, thioredoxin (TRX), His-His-His-His-His-His (SEQ ID NO:62) (His6), lanthanide binding tag (LBT), Asp-Tyr-Lys-Asp-Asp-Asp-Asp-Lys (SEQ ID NO:63) (FLAG (registered trademark)), enhanced green fluorescense protein (EGFP), or the like] and express a protein and/or a protein domain encoded by a foreign gene in the form of a fusion protein linked to the specific protein encoded by the above-mentioned coding region when the foreign gene encoding the protein and/or the protein domain is integrated thereinto. In this case, it is convenient that the vector has the two restriction recognition sequences different in nucleotide sequence which are recognized by the first recognition enzyme on the carboxyl terminal side of the coding region of the specific protein, wherein one of the two restriction recognition sequences located proximal to the coding region of the specific protein comprises a part of a restriction recognition sequence recognized by a second restriction enzyme that is different from the first restriction enzyme, but the restriction recognition sequence located distal to the coding region of the specific protein does not comprise the part of the restriction recognition sequence recognized by the second restriction enzyme.

The second invention of the present patent application provides an open circular vector comprising a double-stranded DNA obtainable by treating the closed circular vector of the first invention of the present patent application with the first restriction enzyme.

As a specific example of the open circular vector of the present invention, an open circular vector comprising a double-stranded DNA represented by the following sequences (XV) and (XVI) may be given.

$$5'-X^{7a}X^{8a}\text{GTC-}N^3\text{-GACX}^{1a}X^{2a}T-3' \quad \text{(SEQ ID NO: 15)} \quad \text{(XV)}$$

$$3'-TX^{7b}X^{8b}\text{CAG-}N^4\text{-CTGX}^{1b}X^{2b}-5' \quad \text{(SEQ ID NO: 16)} \quad \text{(XVI)}$$

(in sequences (XV) and (XVI), G is guanine, A is adenine, C is cytosine, and T is thymine;

$X^{7a}$, $X^{8a}$, $X^{7b}$ and $X^{8b}$ are each independently any base selected from guanine, adenine, cytosine or thymine; $X^{7a}$ and $X^{7b}$ are bases capable of forming a base pair with each other, $X^{8a}$ and $X^{8b}$ are bases capable of forming a base pair with each other;

$X^{1a}$, $X^{2a}$, $X^{1b}$ and $X^{2b}$ are each independently any base selected from guanine, adenine, cytosine or thymine; $X^{1a}$ and $X^{1b}$ are bases capable of forming a base pair with each other, $X^{2a}$ and $X^{2b}$ are bases capable of forming a base pair with each other;

sequence $CX^{1a}X^{2a}T$ is a nucleotide sequence comprising a partial sequence on 5' side of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof;

sequence $CX^{8b}X^{7b}T$ is a nucleotide sequence not comprising the partial sequence of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, TatI, HgiCI, KpnI, SpeI, BlnI, NheI, XbaI, SspI, EcoRV or an isoschizomer thereof that is included in sequence $CX^{1a}X^{2a}T$;

5'- and 3'-represent the individual termini of the double-stranded DNA;

$N^3$ is any nucleotide sequence having 2000-7000 bases; and $N^4$ is a nucleotide sequence complementary to the nucleotide sequence of $N^3$.)

In sequences (XV) and (XVI), preferably, $X^{7a}$ is A, $X^{8a}$ is T, $X^{1a}$ is C, $X^{2a}$ is A, $X^{7b}$ is T, $X^{8b}$ is A, $X^{1b}$ is G, and $X^{2b}$ is T.

As another example of the open circular vector of the present invention, an open circular vector comprising a double-stranded DNA represented by the following sequences (XVII) and (XVIII) may be given.

$$5'-Y^{13a}Y^{14a}Y^{15a}Y^{16a}\text{TGG-}N^3\text{-CCAY}^{1a}Y^{2a}Y^{3a}Y^{4a}T-3' \quad \text{(SEQ ID NO: 17)} \quad \text{(XVII)}$$

$$3'-TY^{13b}Y^{14b}Y^{15b}Y^{16b}\text{ACC-}N^4\text{-GGTY}^{1b}Y^{2b}Y^{3b}Y^{4b}-5' \quad \text{(SEQ ID NO: 18)} \quad \text{(XVIII)}$$

(in sequences (XVII) and (XVIII), G is guanine, A is adenine, C is cytosine, and T is thymine;

$Y^{1a}$, $Y^{2a}$, $Y^{3a}$, $Y^{4a}$, $Y^{1b}$, $Y^{2b}$, $Y^{3b}$ and $Y^{4b}$ are each independently any base selected from guanine, adenine, cytosine or thymine; $Y^{1a}$ and $Y^{1b}$ are bases capable of forming a base pair with each other, $Y^{2a}$ and $Y^{2b}$ are bases capable of forming a base pair with each other, $Y^{3a}$ and $Y^{3b}$ are bases capable of forming a base pair with each other, $Y^{4a}$ and $Y^{4b}$ are bases capable of forming a base pair with each other; sequence $Y^{1a}Y^{2a}Y^{3a}Y^{4a}T$ is a nucleotide sequence comprising a partial sequence on 5' side of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV, AflIII, BspLU11I, NspI, SphI, BspHI, BsaAI, PmaCI, SnaBI, NspBII, PvuII, BanII, HgiAI, SacI or isoschizomer thereof;

$Y^{13a}$, $Y^{14a}$, $Y^{15a}$, $Y^{16a}$, $Y^{13b}$, $Y^{14b}$, $Y^{15b}$ and $Y^{16b}$ are each independently any base selected from guanine, adenine, cytosine or thymine; $Y^{13a}$ and $Y^{13b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other; sequence $Y^{16b}Y^{15b}Y^{14b}Y^{13b}T$ is a nucleotide sequence not comprising the partial sequence of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV, AflIII, BspLU11I, NspI, SphI, BspHI, BsaAI, PmaCI, SnaBI, NspBII, PVuII, BanII, HgiAI, SacI or an isoschizomer that is included in sequence $Y^{1a}Y^{2a}Y^{3a}Y^{4a}T$;

5'- and 3'-represent the individual termini of the double-stranded DNA;

$N^3$ is any nucleotide sequence having 2000-7000 bases; and $N^4$ is a nucleotide sequence complementary to the nucleotide sequence of $N^3$.)

In sequences (XVII) and (XVIII), preferably, $Y^{2a}$ is C, $Y^{3a}$ is C, $Y^{4a}$ is A, $Y^{2b}$ is G, $Y^{3b}$ is G, $Y^{4b}$ is T, $Y^{13a}$ is T, $Y^{14a}$ is G, $Y^{15a}$ is T, $Y^{13b}$ is A, $Y^{14b}$ is C, and $Y^{15b}$ is A.

As still another example of the open circular vector of the present invention, an open circular vector comprising a double-stranded DNA represented by the following sequences (XIX) and (XX) may be given.

```
5'-Y13aY14aY15aY16aTGG-N3-GACX1aX2aT-3'    (SEQ ID NO: 19)
                                            (XIX)
```

```
3'-TY13bY14bY15bY16bACC-5' N4-CTGX1bX2b-5'  (SEQ ID NO: 20)
                                            (XX)
```

(in sequences (XIX) and (XX), G is guanine, A is adenine, C is cytosine, and T is thymine;

$Y^{13a}$, $Y^{14a}$, $Y^{15a}$, $Y^{16a}$, $Y^{13b}$, $Y^{14b}$, $Y^{15b}$ and $Y^{16b}$ are each independently any base selected from guanine, adenine, cytosine or thymine; $Y^{13a}$ and $Y^{13b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other; $X^{1a}$, $X^{2a}$, $X^{1b}$ and $X^{2b}$ are each independently any base selected from guanine, adenine, cytosine or thymine; $X^{1a}$ and $X^{1b}$ are bases capable of forming a base pair with each other, $X^{2a}$ and $X^{2b}$ are bases capable of forming a base pair with each other;

sequence $CX^{1a}X^{2a}T$ is a nucleotide sequence comprising a partial sequence on 5' side of the restriction recognition sequence of NcoI, DsaI, EcoT14I, NdeI, SfeI, AvaI, SmlI, XhoI, PstI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof;

sequence $Y^{14b}Y^{13b}T$ is a nucleotide sequence not comprising the partial sequence of the restriction recognition sequence of NcoI, DsaI, EcoT14I, NdeI, SfeI, AvaI, SmlI, XhoI, PstI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof that is included in sequence $CX^{1a}X^{2a}T$; 5'- and 3'-represent the individual termini of the double-stranded DNA;

$N^3$ is any nucleotide sequence having 2000-7000 bases; and $N^4$ is a nucleotide sequence complementary to the nucleotide sequence of $N^3$.)

In sequences (XIX) and (XX), preferably, $X^{1a}$ is C, $X^{2a}$ is A, $X^{1b}$ is G, $X^{2b}$ is T, $Y^{13a}$ is T, $Y^{14a}$ is G, $Y^{15a}$ is T, $Y^{13b}$ is A, $Y^{14b}$ is C, and $Y^{15b}$ is A.

In sequences (XV) to (XX), $N^3$ may be, for example, a sequence derived from a commercial vector (e.g., pGEX-4T3, pGEX-2T, pGEX-3X, pET21b, pET32a or the like). As a specific example of $N^3$, the following sequence may be given.

```
5'-GGATCCCCGAATTCCCGGGTCGACTCGAGCGGCCGCATCGTGACTGACTGACGATCTGC  (SEQ ID NO: 57)

CTCGCGCGTTTCGGTGATGACGGTGAAAACCTCTGACACATGCAGCTCCCGGAGACGGTCAC

AGCTTGTCTGTAAGCGGATGCCGGGAGCAGACAAGCCCGTCAGGGCGCGTCAGCGGGTGTTG

GCGGGTGTCGGGGCGCAGCCATGACCCAGTCACGTAGCGATAGCGGAGTGTATAATTCTTGA

AGACGAAAGGGCCTCGTGATACGCCTATTTTTATAGGTTAATGTCATGATAATAATGGTTTC

TTAGACGTCAGGTGGCACTTTTCGGGGAAATGTGCGCGGAACCCCTATTTGTTTATTTTTCT

AAATACATTCAAATATGTATCCGCTCATGAGACAATAACCCTGATAAATGCTTCAATAATAT

TGAAAAAGGAAGAGTATGAGTATTCAACATTTCCGTGTCGCCCTTATTCCCTTTTTTGCCGC

ATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGT

TTTCGCCCCGAAGAACGTTTTCCAATGATGAGCACTTTTAAAGTTCTGCTATGTGGCGCGGT

ATTATCCCGTGTTGACGCCGGGCAAGAGCAACTCCGTCGCCGCATACACTATTCTCAGAATG
```

-continued

```
ACTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGCCT
GCAGCAATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTACACCACGGGGAG
CCAGGCAACTATGGATGAACGAAATAGACAGATCGCTGAGATAGGTGCCTCACTGATTAAGC
ATTGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCCGTGGTT
TGTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTAG
CACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTCAG
TGAGCGAGGAAGCGGAAGAGCGCCTGATGCGGTATTTTCTCCTTACGCATCTGTGCGGTATT
TCACACCGCATAAATTCCGACACCATCGAATGGTGCAAAACCTTTCGCGGTATGGCATGATA
GCGCCCGGAAGAGAGTCAATTCAGCGTGGTGAATGTGAAACCAGTAACGTTATACGATGTCG
CAGAGTATGCCGGTGTCTCTTATCAGACCGTTTCCCGCGTGGTGAACCAGGCCAGCCACGTT
TCTGCGAAAACGCGGGAAAAAGTGGAAGCGGCGATGGCGGAGCTGAATTACATTCCCAACCG
CGTGGCACAACAACTGGCGGGCAAACAGTCGTTGCTGATTGGCGTTGCCACCTCCAGTCTGG
CCCTGCACGCGCCGTCGCAAATTGTCGCGGCGATTAAATCTCGCGCCGATCAACTGGGTGCC
AGCGTGGTGGTGTCGATGGTAGAACGAAGCGGCGTCGAAGCCTGTAAAGCGGCGGTGCACAA
TCTTCTCGCGCAACGCGTCAGTGGGCTGATCATTAACTATCCGCTGGATGACCAGGATGCCA
TTGCTGTGGAAGCTGCCTGCACTAATGTTCCGGCGTTATTTCTTGATGTCTCTGACCAGACA
CCCATCAACAGTATTATTTTCTCCCATGAAGACGGTACGCGACTGGGCGTGGAGCATCTGGT
CGCATTGGGTCACCAGCAAATCCCGCTGTTAGCGGGCCCATTAAGTTCTGTCTCGGCGCGTC
TGCGTCTGGCTGGCTGGCATAAATATCTCACTCGCAATCAAATTCAGCCGATAGCGGAACGG
GAAGGCGACTGGAGTGCCATGTCCGGTTTTCAACAAACCATGCAAATGCTGAATGAGGGCAT
CGTTCCCACTCCGATGCTGGTTGCCAACGATCAGATGGCGCTGGGCGCAATGCGCGCCATTA
CCGAGTCCGGGCTGCGCGTTGGTGCGGATATCTCGCTAGTGGGATACGACGATACCGAAGAC
AGCTCATGTTATATCCCGCCGTTAACCACCATCAAACAGGATTTTCGCCTGCTGGGGCAAAC
```

-continued

```
CAGCGTCGACCGCTTGCTGCAACTCTCTCAGGGCCAGGCGGTGAAGGGCAATCAGCTGTTGC
CCGTCTCACTGGTGAAAAGAAAAACCACCCTGGCGCCCAATACGCAAACCGCCTCTCCCCGC
GCGTTGGCCGATTCATTAATGCAGCTGGCACGACAGGTTTCCCGACTGGAAACCGGGCAGTG
AGCGCAACGCAATTAATGTGAGTTAGCTCACTCATTAGGCACCCCAGGCTTTACACTTTATG
CTTCCGGCTCGTATGTTGTGTGGAATTGTGAGCGGATAACAATTTCACACAGGAAACAGCTA
TGACCATGATTACGGATTCACTGGCCGTCGTTTTACAACGTCGTGACTGGGAAAACCCTGGC
GTTACCCAACTTAATCGCCTTGCAGCACATCCCCCTTTCGCCAGCTGGCGTAATAGCGAAGA
GGCCCGCACCGATCGCCCTTCCCAACAGTTGCGCAGCCTGAATGGCGAATGGCGCTTTGCCT
GGTTTCCGGCACCAGAAGCGGTGCCCGAAAGCTGGCTGCAGTGCGATCTTCCTGAGGCCGAT
ACTGTCGTCGTCCCCTCAAACTGGCAGATGCACGGTTACGATGCGCCCATCTACACCAACGT
AACCTATCCCATTACGGTCAATCCGCCGTTTGTTCCCACGGAGAATCCGACGGGTTGTTACT
CGCTCACATTTAATGTTGATGAAAGCTGGCTACAGGAAGGCCAGACGCGAATTATTTTTGAT
GGCGTTGGAATTACGTTATCGACTGCACGGTGCACCAATGCTTCTGGCGTCAGGCAGCCATC
GGAAGCTGTGGTATGGCTGTGCAGGTCGTAAATCACTGCATAATTCGTGTCGCTCAAGGCGC
ACTCCCGTTCTGGATAATGTTTTTTGCGCCGACATCATAACGGTTCTGGCAAATATTCTGAA
ATGAGCTGTTGACAATTAATCATCGGCTCGTATAATGTGTGGAATTGTGAGCGGATAACAAT
TTCACACAGGAAACAGTATTCATGTCCCCTATACTAGGTTATTGGAAAATTAAGGGCCTTGT
GCAACCCACTCGACTTCTTTTGGAATATCTTGAAGAAAAATATGAAGAGCATTTGTATGAGC
GCGATGAAGGTGATAAATGGCGAAACAAAAAGTTTGAATTGGGTTTGGAGTTTCCCAATCTT
CCTTATTATATTGATGGTGATGTTAAATTAACACACTCTATGGCCATCATACGTTATATAGC
TGACAAGCACAACATGTTGGGTGGTTGTCCAAAAGAGCGTGCAGAGATTTCAATGCTTGAAG
GAGCGGTTTTGCATATTAGATACGGTGTTTCGAGAATTGCATATAGTAAAGACTTTGAAACT
CTCAAAGTTGATTTTCTTAGCAAGCTACCTGAAATGCTGAAAATGTTCGAAGATCGTTTATG
TCATAAAACATATTTAAATGGTGATCATGTAACCCATCCTGACTTCATGTTGTATGACGCTC
TTGATGTTGTTTTATACATGGACCCAATGTGCCTGGATGCGTTCCCAAAATTAGTTTGTTTT
AAAAAACGTATTGAAGCTATCCCACAAATTGATAAGTACTTGAAATCCAGCAAGTATATAGC
ATGGCCTTTGCAGGGCTGGCAAGCCACGTTTGGTGGTGGCGACCATCCTCCAAAATCGGATC
TGGTTCCGCGTGCATCC-3'
```

The sequence of SEQ ID NO: 57 is derived from pGEX-4T3.

In sequences (XV) to (XX), $N^4$ is a nucleotide sequence complementary to the nucleotide sequence of $N^3$. As a specific example of $N^4$, the following sequence may be given.

```
3'-CCTAGGGGCTTAAGGGCCCAGCTGAGCTCGCCGGCGTAGCACTGACTGACTGCTAGACG   (SEQ ID NO: 58)
GAGCGCGCAAAGCCACTACTGCCACTTTTGGAGACTGTGTACGTCGAGGGCCTCTGCCAGTG
TCGAACAGACATTCGCCTACGGCCCTCGTCTGTTCGGGCAGTCCCGCGCAGTCGCCCACAAC
CGCCCACAGCCCCGCGTCGGTACTGGGTCAGTGCATCGCTATCGCCTCACATATTAAGAACT
TCTGCTTTCCCGGAGCACTATGCGGATAAAAATATCCAATTACAGTACTATTATTACCAAAG
AATCTGCAGTCCACCGTGAAAAGCCCCTTTACACGCGCCTTGGGGATAAACAAATAAAAAGA
TTTATGTAAGTTTATACATAGGCGAGTACTCTGTTATTGGGACTATTTACGAAGTTATTATA
ACTTTTTCCTTCTCATACTCATAAGTTGTAAAGGCACAGCGGGAATAAGGGAAAAAACGCCG
```

-continued

```
TAAAACGGAAGGACAAAAACGAGTGGGTCTTTGCGACCACTTTCATTTTCTACGACTTCTAG

TCAACCCACGTGCTCACCCAATGTAGCTTGACCTAGAGTTGTCGCCATTCTAGGAACTCTCA

AAAGCGGGGCTTCTTGCAAAAGGTTACTACTCGTGAAAATTTCAAGACGATACACCGCGCCA

TAATAGGGCACAACTGCGGCCCGTTCTCGTTGAGCCAGCGGCGTATGTGATAAGAGTCTTAC

TGAACCAACTCATGAGTGGTCAGTGTCTTTTCGTAGAATGCCTACCGTACTGTCATTCTCTT

AATACGTCACGACGGTATTGGTACTCACTATTGTGACGCCGGTTGAATGAAGACTGTTGCTA

GCCTCCTGGCTTCCTCGATTGGCGAAAAAACGTGTTGTACCCCCTAGTACATTGAGCGGAAC

TAGCAACCCTTGGCCTCGACTTACTTCGGTATGGTTTGCTGCTCGCACTGTGGTGCTACGGA

CGTCGTTACCGTTGTTGCAACGCGTTTGATAATTGACCGCTTGATGAATGAGATCGAAGGGC

CGTTGTTAATTATCTGACCTACCTCCGCCTATTTCAACGTCCTGGTGAAGACGCGAGCCGGG

AAGGCCGACCGACCAAATAACGACTATTTAGACCTCGGCCACTCGCACCCAGAGCGCCATAG

TAACGTCGTGACCCCGGTCTACCATTCGGAGGGCATAGCATCAATAGATGTGGTGCCCCTC

GGTCCGTTGATACCTACTTGCTTTATCTGTCTAGCGACTCTATCCACGGAGTGACTAATTCG

TAACCATTGACAGTCTGGTTCAAATGAGTATATATGAAATCTAACTAAATTTTGAAGTAAAA

ATTAAATTTTCCTAGATCCACTTCTAGCAAAAACTATTAGAGTACTGGTTTTAGGGAATTGC

ACTCAAAAGCAAGGTGACTCGCAGTCTGGGGCATCTTTTCTAGTTTCCTAGAAGAACTCTAG

GAAAAAAAGACGCGCATTAGACGACGAACGTTTGTTTTTTCGTGGCGATGGTCGCCACCAA

ACAAACGGCCTAGTTCTCGATGGTTGAGAAAAAGGCTTCCATTGACCGAAGTCGTCTCGCGT

CTATGGTTTATGACAGGAAGATCACATCGGCATCAATCCGGTGGTGAAGTTCTTGAGACATC

GTGGCGGATGTATGGAGCGAGACGATTAGGACAATGGTCACCGACGACGGTCACCGCTATTC

AGCACAGAATGGCCCAACCTGAGTTCTGCTATCAATGGCCTATTCCGCGTCGCCAGCCCGAC

TTGCCCCCCAAGCACGTGTGTCGGGTCGAACCTCGCTTGCTGGATGTGGCTTGACTCTATGG

ATGTCGCACTCGATACTCTTTCGCGGTGCGAAGGGCTTCCCTCTTTCCGCCTGTCCATAGGC

CATTCGCCGTCCCAGCCTTGTCCTCTCGCGTGCTCCCTCGAAGGTCCCCCTTTGCGGACCAT

AGAAATATCAGGACAGCCCAAAGCGGTGGACACTGAACTCGCAGCTAAAAACACTACGAGCA

GTCCCCCCGCCTCGGATACCTTTTTGCGCTCGTTGCGCCGGAAAAATGCCAAGGACCGGAAA

ACGACCGGAAAACGAGTGTACAAGAAAGGACGCAATAGGGGACTAAGACACCTATTGGCATA

ATGGCGGAAACTCACTCGACTATGGCGAGCGGCGTCGGCTTGCTGGCTCGCCTCGCTCAGTC

ACTCGCTCCTTCGCCTTCTCGCGGACTACGCCATAAAAGAGGAATGCGTAGACACGCCATAA

AGTGTGGCGTATTTAAGGCTGTGGTAGCTTACCACGTTTTGGAAAGCGCCATACCGTACTAT

CGCGGGCCTTCTCTCAGTTAAGTCCCACCACTTACACTTTGGTCATTGCAATATGCTACAGC

GTCTCATACGGCCACAGAGAATAGTCTGGCAAAGGGCGCACCACTTGGTCCGGTCGGTGCAA

AGACGCTTTTGCGCCCTTTTTCACCTTCGCCGCTACCGCCTCGACTTAATGTAAGGGTTGGC

GCACCGTGTTGTTGACCGCCCGTTTGTCAGCAACGACTAACCGCAACGGTGGAGGTCAGACC

GGGACGTGCGCGGCAGCGTTTAACAGCGCCGCTAATTTAGAGCGCGGCTAGTTGACCCACGG

TCGCACCACCACAGCTACCATCTTGCTTCGCCGCAGCTTCGGACATTTCGCCGCCACGTGTT

AGAAGAGCGCGTTGCGCAGTCACCCGACTAGTAATTGATAGGCGACCTACTGGTCCTACGGT

AACGACACCTTCGACGGACGTGATTACAAGGCCGCAATAAAGAACTACAGAGACTGGTCTGT

GGGTAGTTGTCATAATAAAAGAGGGTACTTCTGCCATGCGCTGACCCGCACCTCGTAGACCA

GCGTAACCCAGTGGTCGTTTAGCGCGACAATCGCCCGGGTAATTCAAGACAGAGCCGCGCAG
```

-continued
```
ACGCAGACCGACCGACCGTATTTATAGAGTGAGCGTTAGTTTAAGTCGGCTATCGCCTTGCC
CTTCCGCTGACCTCACGGTACAGGCCAAAAGTTGTTTGGTACGTTTACGACTTACTCCCGTA
GCAAGGGTGACGCTACGACCAACGGTTGCTAGTCTACCGCGACCCGCGTTACGCGCGGTAAT
GGCTCAGGCCCGACGCGCAACCACGCCTATAGAGCCATCACCCTATGCTGCTATGGCTTCTG
TCGAGTACAATATAGGGCGGCAATTGGTGGTAGTTTGTCCTAAAAGCGGACGACCCCGTTTG
GTCGCACCTGGCGAACGACGTTGAGAGAGTCCCGGTCCGCCACTTCCCGTTAGTCGACAACG
GGCAGAGTGACCACTTTTCTTTTTGGTGGGACCGCGGGTTATGCGTTTGGCGGAGAGGGGCG
CGCAACCGGCTAAGTAATTACGTCGACCGTGCTGTCCAAAGGGCTGACCTTTCGCCCGTCAC
TCGCGTTGCGTTAATTACACTCAATCGAGTGAGTAATCCGTGGGGTCCGAAATGTGAAATAC
GAAGGCCGAGCATACAACACACCTTAACACTCGCCTATTGTTAAAGTGTGTCCTTTGTCGAT
ACTGGTACTAATGCCTAAGTGACCGGCAGCAAAATGTTGCAGCACTGACCCTTTTGGGACCG
CAATGGGTTGAATTAGCCGAACGTCCTGTAGGGGGAAAGCGGTCGACCGCATTATCGCTTCT
CCGGGCGTGGCTAGCGGGAAGGGTTGTCAACGCGTCGGACTTACCGCTTACCGCGAAACGGA
CCAAAGGCCGTGGTCTTCGCCACGGCCTTTCGACCGACCTCACGCTAGAAGGACTCCGGCTA
TGACAGCAGCAGGGGAGTTTGACCGTCTACGTGCQAATGCTACGCGGGTACATGTGGTTGCA
TTGGATAGGGTAATGCCAGTTAGGCGGCAAACAAGGGTGCCTCTTAGGCTGCCCAACAATGA
GCGAGTGTAAATTACAACTACTTTCGACCGATGTCCTTCCGGTCTGCGCTTAATAAAAACTA
CCGCAACCTTAATGCAATAGCTGACGTGCCACGTGGTTACGAAGACCGCAGTCCGTCGGTAG
CCTTCGACACCATACCGACACGTCCAGCATTTACTGACGTATTAAGCACAGCGAGTTCCGCG
TGAGGGCAAGACCTATTACAAAAAACGCGGCTGTAGTATTGCCAAGACCGTTTATAAGACTT
TACTCGACAACTGTTAATTAGTAGCCGAGCATATTACACACCTTAACACTCGCCTATTGTTA
AAGTGTGTCCTTTGTCATAAGTACAGGGGATATGATCCAATAACCTTTTAATTCCCGGAACA
CGTTGGGTGAGCTGAAGAAAACCTTATAGAACTTCTTTTTATACTTCTCGTAAACATACTCG
CGCTACTTCCACTATTTACCGCTTTGTTTTTCAAACTTAACCCAAACCTCAAAGGGTTAGAA
GGAATAATATAACTACCACTACAATTTAATTGTGTCAGATACCGGTAGTATGCAATATATCG
ACTGTTCGTGTTGTACAACCCACCAACAGGTTTTCTCGCACGTCTCTAAAGTTACGAACTTC
CTCGCCAAAACCTATAATCTATGCCACAAAGCTCTTAACGTATATCATTTCTGAAACTTTGA
GAGTTTCAACTAAAAGAATCGTTCGATGGACTTTACGACTTTTACAAGCTTCTAGCAAATAC
AGTATTTTGTATAAATTTACCACTAGTACATTGGGTAGGACTGAAGTACAACATACTGCGAG
AACTACAACAAAATATGTACCTGGGTTACACGGACCTACGCAAGGGTTTTAATCAAAGAAAA
TTTTTTGCATAACTTCGATAGGGTGTTTAACTATTCATGAACTTTAGGTCGTTCATATATCG
TACCGGAAACGTCCCCACCGTTCGGTdCAAACCACCACCGCTGGTAGGAGGTTTTAGCCTAG
ACCAAGGCGCACCTAGG-5'
```

The sequence of SEQ ID NO: 58 is complementary to the sequence of SEQ ID NO: 57.

The third invention of the present patent application provides a recombinant vector in which a foreign gene is integrated into the vector of the first invention of the present patent application, the foreign gene comprising a sequence designed in such a manner that a restriction recognition sequence for the second restriction enzyme does not occur when the foreign gene is inserted in the proper orientation into the vector of the first invention treated with the first restriction enzyme, but the restriction recognition sequence for the second restriction enzyme occurs when the foreign gene is inserted thereinto in the opposite orientation. A recombinant vector in which a foreign gene is inserted in the proper direction into the vector of the first invention of the present patent application treated with the first restriction enzyme is preferable. The foreign gene may encode a protein and/or a protein domain.

The fourth invention of the present patent application provides a transformant comprising the recombinant vector of the third invention of the present patent application, or a progeny thereof.

The fifth invention of the present patent application provides a method of preparing the vector of the first invention of the present patent application, comprising introducing into a multicloning site of a plasmid, phage, cosmid, P1 vector, bacterial artificial chromosome vector or yeast artificial chromosome vector a double-stranded DNA comprising two restriction recognition sequences different in nucleotide sequence which are recognized by a first restriction enzyme, one of the restriction recognition sequences comprising a part of a restriction recognition sequence recognized by a second restriction enzyme that is different from the first restriction enzyme, and the other one of the restriction recognition sequences not comprising the part of the restriction recognition sequence recognized by the second restriction enzyme.

The sixth invention of the present patent application provides a double-stranded DNA comprising two restriction recognition sequences different in nucleotide sequence which are recognized by a first restriction enzyme, one of the restriction recognition sequences comprising a part of a restriction recognition sequence recognized by a second restriction enzyme that is different from the first restriction enzyme, and the other one of the restriction recognition sequences not comprising the part of the restriction recognition sequence recognized by the second restriction enzyme.

As a specific example of the double-stranded DNA of the sixth invention of the present patent application, a double-stranded DNA represented by the following sequences (IX) and (X) may be given.

$$5'\text{-GACX}^{1a}X^{2a}TX^{3a}X^{4a}\text{GTC-N}^1\text{-GACX}^{5a}X^{6a}AX^{7a}X^{8a}\text{GTC-3'} \quad \text{(SEQ ID NO: 9)}$$
(IX)

$$3'\text{-CTGX}^{1b}X^{2b}AX^{3b}X^{4b}\text{CAG-N}^2\text{-CTGX}^{5b}X^{6b}TX^{7b}X^{8b}\text{CAG-5'} \quad \text{(SEQ ID NO: 10)}$$
(X)

(in sequences (IX) and (X), G is guanine, A is adenine, C is cytosine, and T is thymine;

$X^{1a}$ to $X^{8a}$ and $X^{1b}$ to $X^{8b}$ are each independently any base selected from guanine, adenine, cytosine or thymine; $X^{1a}$ and $X^{1b}$ are bases capable of forming a base pair with each other, $X^{2a}$ and $X^{2b}$ are bases capable of forming a base pair with each other, $X^{3a}$ and $X^{3b}$ are bases capable of forming a base pair with each other, $X^{4a}$ and $X^{4b}$ are bases capable of forming a base pair with each other, $X^{5a}$ and $X^{5b}$ are bases capable of forming a base pair with each other, $X^{6a}$ and $X^{6b}$ are bases capable of forming a base pair with each other, $X^{7a}$ and $X^{7b}$ are bases capable of forming a base pair with each other, $X^{8a}$ and $X^{8b}$ are bases capable of forming a base pair with each other;

sequence $CX^{1a}X^{2a}T$ is a nucleotide sequence comprising a partial sequence on 5' side of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof;

sequence $CX^{8b}X^{7b}T$ is a nucleotide sequence not comprising the partial sequence of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof that is included in sequence $CX^{1a}X^{2a}T$;

5'- and 3'-represent the individual termini of the double-stranded DNA;

$N^1$ may not exist, and when it exists it is any nucleotide sequence having 1-1000 bases; and $N^2$ may not exist, and when it exists it is a nucleotide sequence complementary to the nucleotide sequence of $N^1$.)

As another specific example of the double-stranded DNA of the sixth invention of the present patent application, a double-stranded DNA represented by the following sequences (XI) and (XII) may be given.

$$5'\text{-CCAY}^{1a}Y^{2a}Y^{3a}Y^{4a}TY^{5a}Y^{6a}Y^{7a}Y^{8a}\text{TGG-N}^1\text{-} \quad \text{(SEQ ID NO: 11)}$$
$$\text{CCAY}^{9a}Y^{10a}Y^{11a}Y^{12a}AY^{13a}Y^{14a}Y^{15a}Y^{16a}\text{TGG-3'} \quad \text{(XI)}$$

$$3'\text{-GGTY}^{1b}Y^{2b}Y^{3b}Y^{4b}AY^{5b}Y^{6b}Y^{7b}Y^{8b}\text{ACC-N}^2\text{-} \quad \text{(SEQ ID NO: 12)}$$
$$\text{GGTY}^{9b}Y^{10b}Y^{11b}Y^{12b}TY^{13b}Y^{14b}Y^{15b}Y^{16b}\text{ACC-5'} \quad \text{(XII)}$$

(in sequences (XI) and (XII), G is guanine, A is adenine, C is cytosine, and T is thymine;

$Y^{1a}$ to $Y^{16a}$ and $Y^{1b}$ to $Y^{16b}$ are each independently any base selected from guanine, adenine, cytosine or thymine; $Y^{1a}$ and $Y^{1b}$ are bases capable of forming a base pair with each other, $Y^{2a}$ and $Y^{2b}$ are bases capable of forming a base pair with each other, $Y^{3a}$ and $Y^{3b}$ are bases capable of forming a base pair with each other, $Y^{4a}$ and $Y^{4b}$ are bases capable of forming a base pair with each other, $Y^{5a}$ and $Y^{5b}$ are bases capable of forming a base pair with each other, $Y^{6a}$ and $Y^{6b}$ are bases capable of forming a base pair with each other, $Y^{7a}$ and $Y^{7b}$ are bases capable of forming a base pair with each other, $Y^{8a}$ and $Y^{8b}$ are bases capable of forming a base pair with each other, $Y^{9a}$ and $Y^{9b}$ are bases capable of forming a base pair with each other, $Y^{10a}$ and $Y^{10b}$ are bases capable of forming a base pair with each other, $Y^{11a}$ and $Y^{11b}$ are bases capable of forming a base pair with each other, $Y^{12a}$ and $Y^{12b}$ are bases capable of forming a base pair with each other, $Y^{13a}$ and $Y^{13b}$ are bases capable of forming a base pair with each other, $Y^{14a}$ and $Y^{14b}$ are bases capable of forming a base pair with each other, $Y^{15a}$ and $Y^{15b}$ are bases capable of forming a base pair with each other, $Y^{16a}$ and $Y^{16b}$ are bases capable of forming a base pair with each other sequence $Y^{1a}Y^{2a}Y^{3a}Y^{4a}T$ is a nucleotide sequence comprising a partial sequence on 5' side of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV, AflIII, BspLU11I, NspI, SphI, BspHI, BsaAI, PmaCI, SnaBI, NspBII, PvuII, BanII, HgiAI, SacI or an isoschizomer thereof;

sequence $Y^{16b}Y^{15b}Y^{14b}Y^{13b}T$ is a nucleotide sequence not comprising the partial sequence of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV, AflIII, BspLU11I, NspI, SphI, BspHI, BsaAI, PmaCI, SnaBI, NspBII, PvuII, BanII, HgiAI, SacI or an isoschizomer thereof that is included in sequence $Y^{1a}Y^{2a}Y^{3a}Y^{4a}T$;

5- and 3-represent the individual termini of the double-stranded DNA;

$N^1$ may not exist, and when it exists it is any nucleotide sequence having 1-1000 bases; and $N^2$ may not exist, and when it exists it is a nucleotide sequence complementary to the nucleotide sequence of $N^1$.)

As a still another example of the double-stranded DNA of the sixth invention of the present patent application, a double-stranded DNA represented by the following sequences (XIII) and (XIV) may be given.

5'-GACX$^{1a}$X$^{2a}$TX$^{3a}$X$^{4a}$GTC-N$^1$- (SEQ ID NO: 13)
CCAY$^{9a}$Y$^{10a}$Y$^{11a}$Y$^{12a}$AY$^{13a}$Y$^{14a}$Y$^{15a}$Y$^{16a}$TGG-3' (XIII)

3'-CTGX$^{1b}$X$^{2b}$AX$^{3b}$X$^{4b}$CAG-N$^2$- (SEQ ID NO: 14)
GGTY$^{9b}$Y$^{10b}$Y$^{11b}$Y$^{12b}$TY$^{13b}$Y$^{14b}$Y$^{15b}$Y$^{16b}$ACC-5' (XIV)

(in sequences (XIII) and (XIV), G is guanine, A is adenine, C is cytosine, and T is thymine;

X$^{1a}$ to X$^{4a}$ and X$^{1b}$ to X$^{4b}$ are each independently any base selected from guanine, adenine, cytosine or thymine; X$^{1a}$ and X$^{1b}$ are bases capable of forming a base pair with each other, X$^{2a}$ and X$^{2b}$ are bases capable of forming a base pair with each other, X$^{3a}$ and X$^{3b}$ are bases capable of forming a base pair with each other, X$^{4a}$ and X$^{4b}$ are bases capable of forming a base pair with each other;

Y$^{9a}$ to Y$^{16a}$ and Y$^{9b}$ to Y$^{16b}$ are each independently any base selected from guanine, adenine, cytosine or thymine; Y$^{9a}$ and Y$^{9b}$ are bases capable of forming a base pair with each other, Y$^{10a}$ and Y$^{10b}$ are bases capable of forming a base pair with each other, Y$^{11a}$ and Y$^{11b}$ are bases capable of forming a base pair with each other, Y$^{12a}$ and Y$^{12}$b are bases capable of forming a base pair with each other, Y$^{13a}$ and Y$^{13b}$ are bases capable of forming a base pair with each other, Y$^{14a}$ and Y$^{14b}$ are bases capable of forming a base pair with each other, Y$^{15a}$ and Y$^{15b}$ are bases capable of forming a base pair with each other, Y$^{16a}$ and Y$^{16b}$ are bases capable of forming a base pair with each other, sequence CX$^{1a}$X$^{2a}$T is a nucleotide sequence comprising a partial sequence on 5' side of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof;

sequence Y$^{14b}$Y$^{13b}$T is a nucleotide sequence not comprising the partial sequence of the restriction recognition sequence of NcoI, DsaI, EcoT14I, NdeI, SfeI, AvaI, SmlI, XhoI, PstI, EcoT22I, PshBI, AccI, ApaLI, PsiI, ScaI, SplI, Bsp1107I, Bsp1286I, BspT107I, Bsp1407I, TatI, HgiCI, KpnI, SpeI, BlnI, NheI, XbaI, SspI, EcoRV or an isoschizomer thereof that is included in sequence CX$^{1a}$X$^{2a}$T;

5'- and 3'-represent the individual termini of the double-stranded DNA;

N$^1$ may not exist, and when it exists it is any nucleotide sequence having 1-1000 bases; and N$^2$ may not exist, and when it exists it is a nucleotide sequence complementary to the nucleotide sequence of N$^1$.)

The seventh invention of the present patent application provides a method of producing a protein and/or a protein domain encoded by a foreign gene, using the vector of the first invention of the present patent application.

In one embodiment of the seventh invention, a recombinant vector may be prepared by integrating into the first vector of the present application a foreign gene which encodes a protein and/or a protein domain and comprises a sequence designed in such a manner that a restriction recognition sequence for the second restriction enzyme does not occur when the foreign gene is inserted in the proper orientation into the vector of the first invention treated with the first restriction enzyme, but the restriction recognition sequence for the second restriction enzyme occurs when the foreign gene is inserted thereinto in the opposite orientation. This recombinant vector may be treated with the second restriction enzyme and then introduced into a host to thereby allow the host to form single colonies. By culturing the single colony-derived host, it is possible to express the protein and/or the protein domain encoded by the foreign gene.

In another embodiment of the seventh invention of the present application, a primer may be used which comprises a sequence designed in such a manner that a restriction recognition sequence for the second restriction enzyme does not occur when the foreign gene is inserted in the proper orientation into the vector of the first invention treated with the first restriction enzyme, but the restriction recognition sequence for the second restriction enzyme occurs when the foreign gene is inserted thereinto in the opposite orientation and which is capable of amplifying the cDNA of a foreign gene encoding a protein and/or protein domain. Using the cDNA as a template, DNA mixtures corresponding to cDNA partial sequences different in location and/or length and/or a part of the sequence of the cDNA may be amplified. Each of the thus amplified mixtures is integrated into the vector of the first invention treated with the first restriction enzyme to thereby prepare a recombinant vector. The recombinant vector is treated with the second restriction enzyme and then introduced into a host to thereby allow the host to form single colonies. By culturing the single colony-derived host, it is possible to express the protein and/or the protein domain encoded by the foreign gene.

The eighth invention of the present patent application provides a method of linearizing a recombinant vector in which a foreign gene is inserted in the opposite orientation and allowing a recombinant vector in which the foreign gene is inserted in the proper orientation to remain unlinearized, using the vector of the first invention of the present patent application.

In one embodiment of the eighth invention of the present patent application, the recombinant vector of the third invention of the present patent application may be treated with the second restriction enzyme to thereby linearize the vector in which a foreign gene is inserted in the opposite orientation and allowing the vector in which the foreign gene is inserted in the proper orientation to remain unlinearized.

The ninth invention of the present patent application provides a method of testing the expression level and/or the solubility of a protein and/or protein domain encoded by a foreign gene, using the vector of the first invention of the present patent application.

In one embodiment of the ninth invention of the present patent application, a recombinant vector may be prepared by integrating into the first vector of the present application a foreign gene which encodes a protein and/or a protein domain and comprises a sequence designed in such a manner that a restriction recognition sequence for the second restriction enzyme does not occur when the foreign gene is inserted in the proper orientation into the vector of the first invention treated with the first restriction enzyme, but the restriction recognition sequence for the second restriction enzyme occurs when the foreign gene is inserted thereinto in the opposite orientation. This recombinant vector may be treated with the second restriction enzyme and then introduced into a host. By culturing the host and/or its progeny, it is possible to express the protein and/or the protein domain encoded by the foreign gene and to examine the expression level and/or the solubility of the thus expressed protein and/or protein domain.

Sequence (I) is shown in SEQ ID NO: 1 of the sequence listing.

Sequence (II) is shown in SEQ ID NO: 2 of the sequence listing.

Sequence (III) is shown in SEQ ID NO: 3 of the sequence listing.

Sequence (IV) is shown in SEQ ID NO: 4 of the sequence listing.

Sequence (V) is shown in SEQ ID NO: 5 of the sequence listing.

Sequence (VI) is shown in SEQ ID NO: 6 of the sequence listing.

Sequence (VII) is shown in SEQ ID NO: 7 of the sequence listing.

Sequence (VIII) is shown in SEQ ID NO: 8 of the sequence listing.

One example of sequence (IX) (when $N^1$ has one base) is shown in SEQ ID NO: 9 of the sequence listing.

One example of sequence (X) (when $N^2$ has one base) is shown in SEQ ID NO: 10 of the sequence listing.

One example of sequence (XI) (when $N^1$ has one base) is shown in SEQ ID NO: 11 of the sequence listing.

One example of sequence (XII) (when $N^2$ has one base) is shown in SEQ ID NO: 12 of the sequence listing.

One example of sequence (XIII) (when $N^3$ has one base) is shown in SEQ ID NO: 13 of the sequence listing.

One example of sequence (XIV) (when $N^4$ has one base) is shown in SEQ ID NO: 14 of the sequence listing.

One example of sequence (XV) (when $N^3$ has one base) is shown in SEQ ID NO: 15 of the sequence listing.

One example of sequence (XVI) (when $N^4$ has one base) is shown in SEQ ID NO: 16 of the sequence listing.

One example of sequence (XVII) (when $N^3$ has one base) is shown in SEQ ID NO: 17 of the sequence listing.

One example of sequence (XVIII) (when $N^4$ has one base) is shown in SEQ ID NO: 18 of the sequence listing.

One example of sequence (XIX) (when $N^3$ has one base) is shown in SEQ ID NO: 19 of the sequence listing.

One example of sequence (XX) (when $N^4$ has one base) is shown in SEQ ID NO: 20 of the sequence listing.

In the present specification, the term "protein domain" refers to a partial sequence of a protein and means a polypeptide having any one of the following properties by itself: some physiological activity, biochemical function, characteristic physicochemical property or tertiary structure.

The expression "(a foreign gene) is inserted in the proper orientation" means that the ORF contained in the gene is inserted into a plasmid in the proper orientation relative to the direction of translation of the plasmid.

The expression "(a foreign gene) is inserted in the opposite orientation" means that the ORF contained in the gene is inserted into a plasmid in the opposite orientation relative to the direction of translation of the plasmid.

The term "restriction recognition sequence" refers to the nucleotide sequence of a double-stranded DNA inherent to each restriction enzyme, which is recognized and cut by the restriction enzyme.

The term "restriction enzyme site" refers to the restriction recognition sequence of a specific restriction enzyme.

The term "multicloning site" refers to a nucleotide sequence in a vector which is designed so that a plurality of restriction enzyme sites occur consecutively.

The term "transformant" refers to a cell which has acquired a novel character as a result of introduction of a foreign gene (DNA), wherein the character is inherited to progeny cells.

The term "host" refers to a living cell into which a recombinant DNA molecule is introduced in recombinant DNA experiments.

The term "vector" refers to a DNA which delivers a heterogenous DNA to a host in recombinant DNA experiments.

The expression "single-colony derived host (or transformant)" refers to a host (or transformant) which has been obtained by inoculating living cells into a medium after sufficient dilution, culturing the cells until they form colonies, separating single colonies, and further culturing those single colonies.

Effect of the Invention

According to the present invention, a vector is provided which is capable of allowing expression of a protein and/or a protein domain by simple operations and in a short period of time.

Further, according to the present invention, a method of allowing expression of proteins and/or protein domains by simple operations and in a short period of time is provided.

Further, according to the present invention, a method of testing the expression level and the solubility of a protein and/or a protein domain by simple operations and in a short period of time is provided.

The present specification encompasses the contents disclosed in the specification and/or drawings of Japanese Patent Application No. 2003-308773 upon which the present patent application claims priority.

BRIEF DESCRIPTION OF THE DRAWINGS

FIG. 2 shows an example where the second restriction enzyme is NcoI, and rear PCR primer is so designed to have 5'-GG. When an insert amplified with this primer is inserted into the plasmid in the opposite orientation, an NcoI site appears at the TA-cloning site. When the second restriction enzyme is NdeI, the rear PCR primer may be designed to have 5'-ATG instead of 5'-GG (SEQ ID NOS 67-70 are disclosed respectively in order of appearance).

FIG. 4 shows the results of analysis of GST-fusion protein expression with 15% SDS-PAGE. Lane M represents molecular weight standards; lanes a1-a5 represent yeast Vps4; lanes b1-b5 represent human Vps4; lanes c1-c5 represent mouse Vps4; lanes d1-d5 represent human Snx15a; and lanes e1-e5 represent mouse Snx15a.

FIG. 6 shows the results of measurement of the solubility of GST-fusion proteins immediately after cell disruption by an assay using 1-chloro-2,4-dinitrobenzene (a method for measuring GST enzyme activity). In this Figure, the horizontal axis shows the time (unit: min) after the start of the reaction and the vertical axis shows UV absorbance at 350 nm. In this graph, Δ represents yeast Vps4; ○ represents human Vps4b; ● represents mouse Vps4b; □ represents human Snx15a; and ▲ represents mouse Snx15a.

BEST MODE FOR CARRYING OUT THE INVENTION

Figure 1:
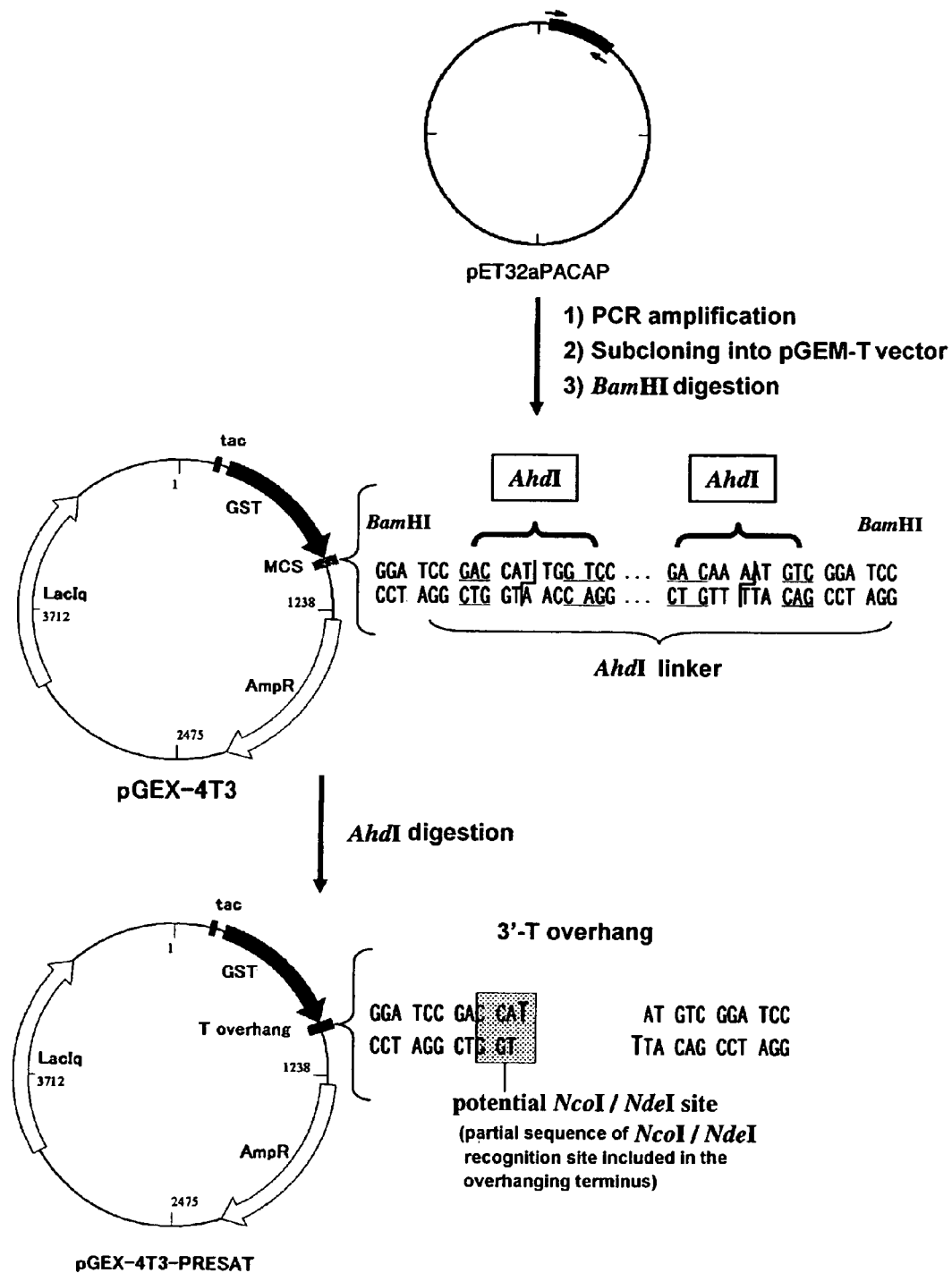
FIG. 1 shows construction of dGST-T vector (pGEX-4T3-PRESAT) (SEQ ID NOS 132 & 64-66 respectively in order of appearance).

Hereinbelow, preferred embodiments of the present invention will be described in detail.

1. Preparation of Vectors

First, a vector is provided. For example, a commercial vector may be purchased and, when this vector has restriction recognition sequences recognized by a first and second restriction enzymes, mutations may be introduced into these restriction recognition sequences. When this vector is a fusion protein expression vector, it is convenient for the following reasons: it is easy to detect/measure the expression level/solubility of the protein and/or protein domain of interest; it is easy to purify the protein and/or protein domain of interest; and such a vector is advantageous in conducting biochemical experiments for functional analysis/interaction analysis of the protein of interest. In Example 1 described later, mutation was introduced into pGEX-4T3 vector using a 5' phosphorylated DNA represented by SEQ ID NO: 21 by site-directed mutagenesis. As a result of this mutagenesis, the AhdI site which pGEX-4T3 originally had in its sequence becomes uncleavable.

Subsequently, a linker is provided which is used for introducing into the above vector two restriction recognition sequences which are different in nucleotide sequence but are both recognized by the first restriction enzyme (only one of these restriction sequences comprises a part of the restriction recognition sequence of the second restriction enzyme that is different from the first restriction enzyme). This linker is designed so that it has a restriction enzyme site at both ends for introduction into the multicloning site of the vector and has the two restriction recognition sequences which are different in nucleotide sequence but are both recognized by the first restriction enzyme (only one of these restriction sequences comprises a part of the restriction recognition sequence of the second restriction enzyme that is different from the first restriction enzyme). In Example 1 described later, PCR was performed using pET32aPACAP (a derivative from pET32a vector) as a template and a pair of primers represented by the sequences of SEQ ID NOS: 22 and 24. As a result, a PCR product with BamHI sites at both ends was obtained; to each of the BamHI sites, AhdI site was linked. This PCR product was subcloned into a TA-cloning vector pGEM-T. After confirmation of the sequence, the plasmid was prepared/purified and then digested with restriction enzyme BamHI to thereby obtain an approx. 500 bp fragment (AhdI linker).

The above-described vector (mutation-introduced pGEX-4T3 vector in Example 1 described later) is linearized with a restriction enzyme (BamHI in Example 1 described later), dephosphorylated, ligated to the above-described linker (AhdI linker in Example 1 described later) and transformed into $E.$ $coli$. Subsequently, plasmids are prepared/purified from transformants derived from a plurality of single colonies. Their nucleotide sequences are confirmed to select those plasmids in which the linker was introduced in the proper orientation. The thus selected plasmids are treated with the first restriction enzyme (AhdI in Example 1 described later) to thereby obtain an open circular vector (pGEX-4T3-PRESAT in Example 1 described later).

2. Preparation of Foreign Genes

A foreign gene is prepared. This foreign gene comprises a sequence which is designed in such a manner that the restriction recognition sequence of the second restriction enzyme does not appear when this gene is inserted into the vector prepared in 1 above in the proper orientation, but the restriction recognition sequence of the second restriction enzyme occurs when this gene is inserted in the opposite orientation. The foreign gene may encode a protein and/or a protein domain.

The foreign gene may be prepared, for example, by PCR. As a template, a cDNA, plasmid, synthetic DNA, RNA or the like comprising a gene of interest may be used. As primers, two oligonucleotides which are complementary to the DNA sequences at both terminals of the gene of interest may be used. These primers must be designed exactly in advance so that the following conditions are satisfied: for one of these primers, the reading frame of translation should not shift after insertion into the vector and, for the other one of these primers, a sequence of 1-10 bases not included in the gene of interest should be added at its 5' end.

The PCR reaction is usually performed by repeating 20 to 40 cycles, one cycle consisting of the three reactions of dissociation of two DNA strands, annealing with oligonucleotides, and synthesis of complementary strands by DNA polymerase. By using an enzyme having DNA reverse transcription activity in the first reaction, it is also possible to amplify DNA from RNA.

The nucleotide sequences of the primers are designed in such a manner that the restriction recognition sequence of the second restriction enzyme does not occur when the PCR product is inserted into the vector prepared in 1 above in the proper orientation, but the restriction recognition sequence of the second restriction enzyme occurs when the PCR product is inserted in the opposite orientation. In Example 2 described later, the front primer (primer corresponding to the N-terminal of the ORF of the cDNA) was designed in such a manner that (i) it starts with the first codon of any amino acid so that the reading frame coincides with that of the preceding GST and (ii) the 5'-end nucleotides of this primer do not start with 5'-GG. The rear primer (primer corresponding to the C-terminal of the ORF) was designed in such a manner that (i) a stop codon is contained after the boundary of the presumed C terminal region of the protein domain and (ii) the 5'-end nucleotides of this primer start with 5'-GG. As a result, the PCR product amplified with these primers has an NcoI site generated only when it has been ligated to pGEX-4T3-PRESAT in the opposite orientation. This newly generated NcoI site is used in the subsequent selection step.

Other matters to be attended to in designing PCR primers for amplifying DNA to be integrated into pGEX-4T3-PRESAT for recombinant protein production will be described below.

(1) When the First Restriction Enzyme is AhdI and the Second Restriction Enzyme is NcoI (NcoI Selection)

The primer corresponding to the N-terminal of the ORF may be designed according to the following four rules.
(ia) The first base of the primer sequence must correspond to the first base of an amino acid codon so that the reading frame coincides with the reading frame of the preceding GST.
(iia) The base at 5'-end must be G or A. (If necessary, a DNA sequence encoding a small number of amino acids may be inserted.)
(iiia) 5'-end sequence must not be GG.
(iva) NcoI restriction enzyme site must not be included in the PCR amplified fragment.

The primer corresponding to the C-terminal of the ORF may be designed according to the following two rules.
(va) 5'-end sequence must be GG.
(via) When the protein domain of interest does not contain a stop codon, 5'-end sequence must start with GG-Xn-TTA [where Xn may be any bases in a number of n (where n is an integer from 0 to 30); e.g., Xn may be A] (an example of sequence where n=5 is shown in SEQ ID NO: 53).

(2) When the First Restriction Enzyme is AhdI and the Second Restriction Enzyme is NdeI (NdeI Selection)

The primer corresponding to the N-terminal of the ORF may be designed according to the following four rules.
(ib) The first base of the primer sequence must correspond to the first base of an amino acid codon so that the reading frame coincides with the reading frame of the preceding GST.
(iib) The base at 5'-end must be G or A. (If necessary, a DNA sequence encoding a small number of amino acids may be inserted.)
(iiib) 5'-end sequence must not be ATG.
(ivb) NdeI restriction enzyme site must not be included in the PCR amplified fragment.

The primer corresponding to the C-terminal of the ORF may be designed according to the following two rules.
(vb) 5'-end sequence must be ATG.
(vib) When the protein domain of interest does not contain a stop codon, 5'-end sequence must start with ATG-Xn-TTA [where Xn may be any bases in a number of n (where n is an integer from 0 to 30); e.g., Xn may be A] (an example of sequence where n=4 is shown in SEQ ID NO: 54).

3. Cloning

The foreign gene prepared in 2 above is ligated to the vector prepared in 1 above (pGEX-4T3-PRESAT vector in Example 2 described later), which is then transformed into *E. Coli*. The transformed *E. coli* is not inoculated into agar medium or allowed single colony formation. The transformant is cultured in liquid medium, from which a plasmid mixture is purified. When this plasmid mixture is treated with the second restriction enzyme (NcoI in Example 2 described later), those plasmids in which the foreign gene has been inserted into the vector in the opposite orientation are cut at the newly generated restriction site of the second restriction enzyme and linearized. On the other hand, those plasmids in which the foreign gene has been inserted into the vector in the proper orientation remain unlinearized. Therefore, when the plasmid mixture treated with the second restriction enzyme is transformed into an *E. coli* host for expression and the resultant transformant is spread on agar medium, only those *E. coli* cells which harbor a plasmid where the foreign gene has been inserted into the vector in the proper orientation form colonies. From each of the single colonies formed on the agar-medium, *E. coli* is collected, cultured and allowed to express a fusion protein. Those *E. coli* cells which have completed expression are harvested and disrupted by sonication or the like to thereby prepare a total cell lysate fraction. Further, the total cell lysate fraction is centrifuged to obtain the supernatant as a soluble fraction. The precipitate is dissolved completely with an SDS-containing buffer of the same volume as that of the solubilized fraction, to thereby prepare an insoluble fraction. The total cell lysate fraction alone or each of the total cell lysate fraction, soluble fraction and insoluble fraction is analyzed by SDS-PAGE, followed by confirmation of the band of the protein of interest on the gel. Subsequently, a ratio between the soluble fraction and the insoluble fraction is determined from the thickness of the bands of the fusion protein on the gel. This ratio is used as an indicator for the solubility of the fusion protein of interest (solubility test). It will be still better to quantitatively determine protein bands on the gel using densitometry or the like.

Solubility tests using the enzyme activity of GST are performed based on the method described in the Amersham Pharmacia's manual for handling pGEX series vectors. Briefly, *E. coli* soluble fraction containing the fusion protein of interest diluted in an appropriate buffer is placed in a cuvette in a UV spectrophotometer. After 1-chloro-2,4-dinitrobenzene and reduced glutathione are added thereto and agitated thoroughly, time course of UV absorbance at 340 nm is measured consecutively up to 5 to 10 minutes. The resultant slope is used as an indicator for the amount of the fusion protein of interest. When a large number of samples are handled in parallel, use of a microplate reader is convenient.

After the above-described operations, clones which are good in the expression level and solubility of the fusion protein of interest are selected. Then, plasmids are purified and their nucleotide sequences are determined. A plasmid comprising the foreign gene of interest is employed as an expression vector for the protein and/or protein domain, and used in subsequent mass production experiments. According to this method, it has become possible to reduce the time period required for preparing an expression vector for a protein and/or protein domain of interest by about 30% compared to the conventional method.

4. Mass Production of Proteins and/or Protein Domains

The protein and/or protein domain expression vector employed in 3 above is transformed into an *E. coli* host for expression. The resultant transformant is cultured and allowed to express the protein and/or protein domain of interest. When the protein and/or protein domain expression vector is a fusion protein expression vector, it is convenient for the following reasons: it is easy to detect/measure the expression level/solubility of the protein and/or protein domain of interest (e.g., detection by means of fluorescence, calorimetric assay using the enzyme activity of GST as an indicator, etc.); it is easy to purify the protein and/or protein domain of interest (e.g., one step purification using GSH-immobilized beads is possible); and such a vector is advantageous in conducting biochemical experiments for functional analysis/interaction analysis of the protein of interest (e.g., in vitro binding experiment using BIACORE, in vitro binding experiments using pull down assay, etc.).

Isolation and purification of the expressed protein and/or protein domain may be performed by known methods. Known methods of isolation and purification include, but are not limited to, methods using solubility (such as salting out and solvent precipitation); methods using difference in molecular weight (such as dialysis, ultra-filtration, gel filtration, and SDS-polyacrylamide gel electrophoresis); methods using difference in electric charge (such as ion exchange chromatography); methods using specific affinity (such as affinity chromatography); methods using difference in hydrophobicity (such as reversed phase HPLC and hydrophobic chromatography); and methods using difference in isoelectric point (such as isoelectric focusing).

The present invention has been described so far using *E. coli* as a host. However, the host used in the present invention is not limited to *E. coli*. Examples of hosts which may be used in the present invention include, but are not limited to, bacterial cells (e.g., *Escherichia bacteria*, *Bacillus bacteria*, *Bacillus subtilis*), fungal cells (e.g., budding yeast, fission yeast, *Aspergillus*), insect cells (e.g., S2 cells, Sf cells), animal cells (e.g., CHO cells, COS cells, HeLa cells, C127 cells, 3T3 cells, BHK cells, HEK293 cells) and plant cells.

The first restriction enzyme, second restriction enzyme, two restriction recognition sequences different in nucleotide sequence which are recognized by the first restriction enzyme (one comprising a part of the restriction recognition sequence recognized by the second restriction enzyme, and the other not comprising that part) and pair of PCR primers for preparing a foreign gene used in the present invention are not limited to those described above. The enzymes and sequences summarized in the following Tables (I II and III) may be used. In the Tables, G is guanine, A is adenine, C is cytosine, T is thymine, X is any base, and Xn represents any bases in a number of n (where n is an integer from 0 to 30).

Table I

TABLE I

| First restriction enzyme | Restriction recognition sequence (i) of first restriction enzyme (comprising a part (underlined portion) of the restriction recognition sequence of second restriction enzyme) | Restriction recognition sequence (ii) of first restriction enzyme (not comprising the part the restriction recognition sequence of second restriction enzyme) | Second restriction enzyme | Restriction recognition sequence of second restriction enzyme |
|---|---|---|---|---|
| Ahdt | 5'-GA<u>CC</u>ATTGGTC-3'<br>3'-CT<u>GG</u>TAACCAG-5'<br>(SEQ ID NO: 71) | 5'-GACAAAATGTC-3'<br>3'-CTGTTTTACAG-5'<br>(SEQ ID NO: 77) | NcoI<br>DsaI<br>EcoT14I | 5'-CCATGG-3'<br>3'-GGTACC-5' |
|  | 5'-GAC<u>CA</u>TTGGTC-3'<br>3'-CT<u>GG</u>TAACCAG-5'<br>(SEQ ID NO: 71) | 5'-GACAAAATGTC-3'<br>3'-CTGTTTTACAG-5'<br>(SEQ ID NO: 77) | NdeI | 5'-CATATG-3'<br>3'-GTATAC-5' |
|  | 5'-GACX<u>C</u>TTGGTC-3'<br>3'-CTGX<u>GA</u>ACCAG-5'<br>(X is any base)<br>(SEQ ID NO: 72) | 5'-GACAAAATGTC-3'<br>3'-CTGTTTTACAG-5'<br>(SEQ ID NO: 77) | Sfe I | 5'-CTATAG-3'<br>3'GATATC-5' |
|  | 5'-GA<u>CTAT</u>TGGTC-3'<br>3'-CT<u>GATA</u>ACCAG-5'<br>(SEQ ID NO: 73) | 5'GACAAAATGTC-3'<br>3'CTGTTTTACAG-5'<br>(SEQ ID NO: 77) | Sfe I | 5'-CTATAG-3'<br>3'-GATATC-5' |
|  | 5'-CA<u>CAA</u>TTGGTC-3'<br>3'CT<u>GTT</u>AACCAG-5'<br>(SEQ ID NO: 74) | 5'GACAAAATGTC-3'<br>3'-CTGTTTTACAG-5'<br>(SEQ ID NO: 77) | Mun I | 5'-CAATTG-3'<br>3'-GTTAAC-5' |
|  | 5'-GA<u>CG</u>ATTGGTC-3'<br>3'-CT<u>GCTA</u>ACCAG-5'<br>(SEQ ID NO: 75) | 5'GACAAAATGTC-3'<br>3'-CTGTTTTACAG-5'<br>(SEQ ID NO: 77) | Mcr I<br>Pvu I | 5'-CGATCG-3'<br>3'-GCTAGC-5' |
|  | 5'-GACX<u>C</u>TTGGTC-3'<br>3'-CTGX<u>GA</u>ACCAG-5'<br>(X is any base)<br>(SEQ ID NO: 72) | 5'-GACAAAATGTC-3'<br>3'-CTGTTTTACAG-5'<br>(SEQ ID NO: 77) | Ava I<br>Sml I<br>Xho I | 5'CTCGAG-3'<br>3'-GAGCTC-5' |
|  | 5'-GACX<u>C</u>TTGGTC-3'<br>3'-CTGX<u>GA</u>ACCAG-5'<br>(X is any base)<br>(SEQ ID NO: 72) | 5'-GACAAAATGTC-3'<br>3'-CTGTTTTACAG-5'<br>(SEQ ID NO: 77) | Pst I<br>Sfe I | 5'-CTGCAG-3'<br>3'GACGTC-5' |

TABLE I-continued

| | | | |
|---|---|---|---|
| 5'GACXCTTGGTC-3'<br>3'-CTGXGAACCAG-5'<br>(X is any base)<br>(SEQ ID NO: 72) | 5'-GACAAAATGTC-3'<br>3'-CTGTTTTACAG-5'<br>(SEQ ID NO: 77) | Afl II<br>Sml I | 5'-CTTAAG-3'<br>3'-GAATTC-5' |
| 5'-GACXATTGGTC-3'<br>3'-CTGXTAACCAG-5'<br>(X is any base)<br>(SEQ ID NO: 76) | 5'-GACAAAATGTC-3'<br>3'-CTGTTTTACAG-5'<br>(SEQ ID NO: 77) | Cla I | 5'-ATCGAT-3'<br>3'-TAGCTA-5' |
| 5'-GACXATTGGTC-3'<br>3'-CTGXTAACCAG-5'<br>(X is any base)<br>(SEQ ID NO: 76) | 5'-GACAAAATGTC-3'<br>3'-CTGTTTTACAG-5'<br>(SEQ ID NO: 77) | EcoT22I | 5'-ATGCAT-3'<br>3'TACGTA-5' |
| 5'-GACXATTGGTC-3'<br>3'-CTGXTAACCAG-5'<br>(X is any base)<br>(SEQ ID NO: 76) | 5'-GACAAAATGTC-3'<br>3'-CTGTTTTACAG-5'<br>(SEQ ID NO: 77) | PshB I | 5'-ATTAAT-3'<br>3'-TAATTA-5' |
| 5'-GACATTTGGTC-3'<br>3'-CTGTAAACCAG-5'<br>(SEQ ID NO: 78) | 5'-GACAAATTGTC-3'<br>3'-CTGTTTAACAG-5'<br>(SEQ ID NO: 86) | PshB I | 5'-ATTAAT-3'<br>3'-TAATTA-5' |
| 5'-GACXGTTGGTC-3'<br>3'-CTGXCAACCAG-5'<br>(X is any base)<br>(SEQ ID NO: 79) | 5'-GACAAAATGTC-3'<br>3'-CTGTTTTACAG-5'<br>(SEQ ID NO: 77) | Acc I<br>Bst1107 I | 5'-GTATAC-3'<br>3'-CATATG-5' |
| 5'-GACXGTTGGTC-3'<br>3'-CTGXCAACCAG-5'<br>(X is any base)<br>(SEQ ID NO: 79) | 5'-GACAAAATGTC-3'<br>3'-CTGTTTTACAG-5'<br>(SEQ ID NO: 77) | Acc I<br>Hinc II<br>Sal I | 5'-GTCGAC-3'<br>3'CAGCTG-5' |
| 5'-GACXGTTGGTC-3'<br>3'-CTGXCAACCAG-5'<br>(X is any base)<br>(SEQ ID NO: 79) | 5'-GACAAAATGTC-3'<br>3'-CTGTTTTACAG-5'<br>(SEQ ID NO: 77) | ApaL I<br>Bsp1286 I<br>HgiA I | 5'GTGAC-3'<br>3'-CACTG-5 |
| 5'-GACXGTTGGTC-3'<br>3'-CTGXCAACCAG-5'<br>(X is any base)<br>(SEQ ID NO: 79) | 5'-GACAAAATGTC-3'<br>3'-CTGTTTTACAG-5'<br>(SEQ ID NO: 77) | Hinc II<br>Hpa I | 5'-GTTAC-3'<br>3'-CAATTG-5' |
| 5'GACXTTTGGTC-3'<br>3'-CTGXAAACCAG-5'<br>(X is any base)<br>(SEQ ID NO: 80) | 5'-GACAAATTGTC-3'<br>3'-CTGTTTAACAG-5'<br>(SEQ ID NO: 86) | Psi I | 5'-TTATAA-3'<br>3'-AATATT-5' |
| 5'-GACXTTTGGTC-3'<br>3'-CTGXAAACCAG-5'<br>(X is any base)<br>(SEQ ID NO: 80) | 5'-GACAAATTGTC-3'<br>3'-CTGTTTAACAG-5'<br>(SEQ ID NO: 86) | NspV<br>BspT104I | 5'-TTCGAA-3'<br>3'-AAGCTT-5' |
| 5'-GACXTTTGGTC-3'<br>3'-CTGXAAACCAG-5'<br>(X is any base)<br>(SEQ ID NO: 80) | 5'-GACAAATTGTC-3'<br>3'-CTGTTTAACAG-5'<br>(SEQ ID NO: 86) | Dra I | 5'-TTTAAA-3'<br>3'-AAATTT-5 |
| 5'-GACAGTTGGTC-3'<br>3'CTGTCAACCAG-5'<br>(SEQ ID NO: 81) | 5'GACAAAATGTC-3'<br>3'-CTGTTTTACAG-5'<br>(SEQ ID NO: 77) | Sca I<br>Tat I | 5'-AGTACT-3'<br>3'-TCATGA-5' |
| 5'-GACCGTTGGTC-3'<br>3'-CTCGCAACCAG-5'<br>(SEQ ID NO: 82) | 5'-GACAAAATGC-3'<br>3'-CTGTTTTACAG-5'<br>(SEQ ID NO: 77) | Spl I | 5'-CGTACG-3'<br>3'-GCATGC-5' |
| 5'GACGGTTGGTC-3'<br>3'-CTGCCAACCAG-5'<br>(SEQ ID NO: 83) | 5'-GACAAAATGTC-3'<br>3'-CTGTTTTACAG-5'<br>(SEQ ID NO: 77) | BspT107I<br>HgiCI<br>Kpn I | 5'-GGTACC-3'<br>3'-CCATGG-5' |
| 5'GACTGTTGGTC-3'<br>3'-CTGACAACCAG-5'<br>(SEQ ID NO: 84) | 5'-GACAAAAGTC-3'<br>3'-CTGTTTTACAG-5'<br>(SEQ ID NO: 77) | Bsp1407 I<br>Tat I | 5'-TGTACA-3'<br>3'-ACATGT-5' |
| 5'-GACACTTGGTC-3'<br>3'-CTGTGAACCAG-5'<br>(SEQ ID NO: 85) | 5'-GACAAAATGTC-3'<br>3'-CGTTTTACAG-5'<br>(SEQ ID NO: 77) | Spe I | 5'-ACTAGT-3'<br>3'-TGATCA-5' |

TABLE I-continued

| | | | |
|---|---|---|---|
| 5'-GACCCTTGGTC-3'<br>3'-CTGGGAACCAG-5'<br>(SEQ ID NO: 87) | 5'-GACAAAATGTC-3'<br>3'-CTGTTTTACAG-5'<br>(SEQ ID NO: 77) | Bln I<br>EcoT14I | 5'-CCTAGG-3'<br>3'-GGATCC-5' |
| 5'-GACGCTTGGTC-3'<br>3'-CTGCGAACCAG-5'<br>(SEQ ID NO: 88) | 5'GACAAAATGTC-3'<br>3'CTGTTTTACAG-5'<br>(SEQ ID NO: 77) | Nhe I | 5'-GCTAGC-3'<br>3'-CGATCG-5' |
| 5'-GACTCTTGGTC-3'<br>3'-CTGAGAACCAG-5'<br>(SEQ ID NO: 89) | 5'-GACAAAATGTC-3'<br>3'-CTGTTTTACAG-5'<br>(SEQ ID NO: 77) | Xba I | 5'-TCTAGA-3'<br>3'-AGATCT-5' |
| 5'-GACAATTGGTC-3'<br>3'-CTGTTAACCAG-5'<br>(SEQ ID NO: 74) | 5'-GACAAAATGTC-3'<br>3'-CTGTTTTACAG-5'<br>(SEQ ID NO: 77) | Ssp I | 5'-AATATT-3'<br>3'-TTATAA-5' |
| 5'-GACGATTGGTC-3'<br>3'-CTGCTAACCAG-5'<br>(SEQ ID NO: 75) | 5'-GACAAAATGTC-3'<br>3'-CTGTTTTACAG-5'<br>(SEQ ID NO: 77) | EcoRV | 5'-GATATC-3'<br>3'-CTATAG-5' |

| First restriction enzyme | 5'-end and 3'-end sequences of a foreign gene to be inserted into a vector (large letter "A" represents the base of a nucleotide added in PCR reaction) | Requirement that the 5'-end sequence of front primer for preparing a foreign gene must satisfy | Sequence added to the 5'-end of rear primer for preparing a foreign gene (when stop codon is not added) | Sequence added to the 5' end of rear primer for preparing a foreign gene (when stop codon is also added) |
|---|---|---|---|---|
| Ahdt | 5'-XXXX-//-XXCA-3'<br>3'-AXXXX-//-XXGG-5'<br>(X is any base) | Not including 5'-GG | 5'-GG | 5'-GGXnTTA<br>(Xn represents any bases in a number of n) |
| | 5'-XXXX-//-XXCATA-3'<br>3'AXXXX-//-XXGTA-5'<br>(X is any base) | Not including 5'-ATG | 5'-ATG | 5'ATGXnTTA<br>(Xn represents any bases in a number of n) |
| | 5'-XXXX-//-XXCTATA-3'<br>3'-AXXXX-//-XXGATA-5'<br>(X is any base) | Not including 5'-ATG | 5'-ATAG | 5'ATAGXnTTA<br>(Xn represents any bases in a number of n) |
| | 5'-XXXX-//-XXCTA-3'<br>3'-AXXXX-//-XXGA-5'<br>(X is any base) | Not including 5'-AG | 5'-AG | 5'-AGXnTTA<br>(Xn represents any bases in a number of n) |
| | 5'-XXXX-//-XXCA-3'<br>3'-AXXXX-//-XXGT-5'<br>(X is any base) | Not including 5'-TG | 5'-TG | 5'-TGXnTTA<br>(Xn represents any bases in a number of n) |
| | 5'-XXXX-//-XXCGA-3'<br>3'-AXXXX-//-XXGC-5'<br>(X is any base) | Not including 5'-CG | 5'-CG | 5'-CGXnTTA<br>(Xn represents any bases in a number of n) |
| | 5'-XXXX-//-XXCTCGA-3'<br>3'-AXXXX-//-XXGAGC-5'<br>(X is any base) | Not including 5'-CGAG | 5'-GCAC | 5'CGAGXnTTA<br>(Xn represents any bases in a number of n) |
| | 5'-XXXX-//-XXCTGCA-3'<br>3'-AXXXX-//-XXGAGG-5'<br>(X is any base) | Not including 5'-GCAG | 5'-GCAG | 5'GCAGXnTTA<br>(Xn represents any bases in a number of n) |
| | 5'-XXXX-//-XXCTTAA-3'<br>3'-AXXXX-//-XXGAAT-5'<br>(X is any base) | Not including 5'-TAAG | 5'-TAAG | 5'-TAAGXnTTA<br>(Xn represents any bases in a number of n) |

TABLE I-continued

| | | |
|---|---|---|
| 5'-XXXX-//-XXATCGA-3'<br>3'-AXXXX-//-XXTAGC-5'<br>(X is any base) | Not including 5'-CGAT<br>5'-CGAT | 5'-CGATXnTTA<br>(Xn represents any bases in a number of n) |
| 5'-XXXX-//-XXATGCA-3'<br>3'AXXXX-//-XXTACG-5'<br>(X is any base) | Not including 5'-GCAT<br>5'-GCAT) | 5'-GCATXnTTA<br>(Xn represents any bases in a number of n) |
| 5'-XXXX-//-XXATTA-3'<br>3'AXXX-//-XXTAAT-5'<br>(X is any base) | Not including 5'-TAAT<br>5'-TAAT | 5'-TAATXnTTA<br>(Xn represents any bases in a number of n) |
| 5'-XXXX-//-XXATTA-3'<br>3'-AXXXX-//-XXTAA-5'<br>(X is any base) | Not including 5'-AAT<br>5'-AAT | 5'-AATXnTTA<br>(Xn represents any bases in a number of n) |
| 5'-XXXX-//-XXGTATA-3'<br>3'-AXXXX-//-XXCATA-5'<br>(X is any base) | Not including 5'-ATAC<br>5'-ATAC | 5'-ATACXnTTA<br>(Xn represents any bases in a number of n) |
| 5'-XXXX-//-XXGTCGA-3'<br>3'-AXXXX-//-XXCAGC-5'<br>(X is any base) | Not including 5'-CGAC<br>5'-CGAC | 5'-CGACXnTTA<br>(Xn represents any bases in a number of n) |
| 5'-XXXX-//-XXGTGCA-3'<br>3'-AXXXX-//-XXCACG-5'<br>(X is any base) | Not including 5'-GCAC<br>5'-GCAC | 5'GCACXnTTA<br>(Xn represents any bases in a number of n) |
| 5'-XXXX-//-XXGTTAA-3'<br>3'-AXXXX-//-XXCAAT-5'<br>(X is any base) | Not including 5'-TAAC<br>5'-TAAC | 5'TAACXnTTA<br>(Xn represents any bases in a number of n) |
| 5'-XXXX-//-XXTTATA-3'<br>3'-AXXX-//-XXAATA-5'<br>(X is any base) | Not including 5'-ATAA<br>5'-ATAA | 5'-ATAAXnTTA<br>(Xn represents any bases in a number of n) |
| 5'-XXXX-//-XXTTCGA-3'<br>3'-AXXXX-//-XXAAGC-5'<br>(X is any base) | Not including 5'-CGAA<br>5'-CGAA | 5'-CGAAXnTTA<br>(Xn represents any bases in a number of n) |
| 5'-XXXX-//-XXTTTAA-3'<br>3'-AXXXX-//-XXAAAT-5'<br>(X is any base) | Not including 5'-TAAA<br>5'-TAAA | 5'-TAAAXnTTA<br>(Xn represents any bases in a number of n) |
| 5'-XXXX-//-XXGTA-3'<br>3'-AXXXX-//-XXTCA-5'<br>(X is any base) | Not including 5'-ACT<br>5'-ACT | 5'-ACTXnTTA<br>(Xn represents any bases in a number of n) |
| 5'-XXXX-//-XXGGTA-3'<br>3'-AXXXX-//-XXGCA-5'<br>(X is any base) | Not including 5'-ACG<br>5'-ACG | 5'-ACGXnTTA<br>(Xn represents any bases in a number of n) |
| 5'-XXXX-//-XXGGTA-3'<br>3'-AXXXX-//-XXCCA-5'<br>(X is any base) | Not including 5'-ACC<br>5'-ACC | 5'-ACCXnTTA<br>(Xn represents any bases in a number of n) |
| 5'-XXXX-//-XXGTA-3'<br>3'-AXXXX-//-XXCA-5'<br>(X is any base) | Not including 5'-ACA<br>5'-ACA | 5'-ACAXnTA<br>(Xn represents any bases in a number of n) |
| 5'-XXXX-//-XXACTA-3'<br>3'-AXXXX//-XXTGA-5'<br>(X is any base) | Not including 5'-AGT<br>5'-AGT | 5'-AGTXnTTA<br>(Xn represents any bases in a number of n) |

TABLE I-continued

| | | |
|---|---|---|
| 5'-XXXX-//-XXCCTA-3'<br>3'-AXXX-//-XXGA-5'<br>(X is any base) | Not including 5'-AGG<br>5'-AGG | 5'-AGGXnTTA<br>(Xn represents any bases in a number of n) |
| 5'-XXXX-//-XXGCTA-3'<br>3'-AXXXX-//-XXCGA-5'<br>(X is any base) | Not including 5'-AGC<br>5'-AGC | 5'-AGCXnTTA<br>(Xn represents any bases in a number of n) |
| 5'-XXXX-//-XXTCTA-3'<br>3'-AXXXX-//-XXAGA-5'<br>(X is any base) | Not including 5'-AGA<br>5'-AGA | 5'-AGAXnTTA<br>(Xn represents any bases in a number of n) |
| 5'-XXXX-//-XXAATA-3'<br>3'-AXXXX-//-XXTTA-5'<br>(X is any base) | Not including 5'-ATT<br>5'-ATT | 5'-ATTXnTTA<br>(Xn represents any bases in a number of n) |
| 5'-XXXX-//-XXGATA-3'<br>3'-AXXXX-//-XXCTA-5'<br>(X is any base) | Not including 5'-ATC<br>5'-ATC | 5'ATCXnTTA<br>(Xn represents any bases in a number of n) |

TABLE II

| First restriction enzyme | Restriction recognition sequence (i) of first restriction enzyme (comprising a part (underlined portion) of the restriction recognition sequence of second restriction enzyme) | Restriction recognition sequence (ii) of first restriction enzyme (not comprising the part of the restriction recognition sequence of second restriction enzyme) | Second restriction enzyme | Restriction recognition sequence of second restriction enzyme |
|---|---|---|---|---|
| Ahdt/XcmI | 5'-GACCATTCGTC-3'<br>3'-CTGGTAAACCAG-5'<br>(SEQ ID NO: 71) | 5'-CCAATAAATGGCTGG-3'<br>3'-GGTTATTTACCGACC-5'<br>(SEQ ID NO: 90) | NcoI<br>DsaI<br>EcoT14I | 5'-CCATCG-3'<br>3'-GGTACC-5' |
| | 5'-GACCATTGGTC-3'<br>3'-CTGGTAACCAG-5'<br>(SEQ ID NO: 71) | 5'-CCAATAAATGGCTGG-3'<br>3'-GGTTATTTACCGACC-5'<br>(SEQ ID NO: 90) | NdeI | 5'-CATATG-3'<br>3'-GTATAC-5' |
| | 5'-GACXCTTGGTC-3'<br>3'-CTGXGAACCAG-5'<br>(X is any base)<br>(SEQ ID NO: 72) | 5'-CCAATAAATGGCTGG-3'<br>3'-GGTTATTTACCGACC-5'<br>(SEQ ID NO: 90) | Sfe I | 5'-CTATAG-3'<br>3'-GATATC-5' |
| | 5'-GACTATTGGTC-3'<br>3'-CTGATAACCAG-5'<br>(SEQ ID NO: 73) | 5'-CCAATAAATGGCTGG-3'<br>3'-GGTTATTTACCGACC-5'<br>(SEQ ID NO: 90) | Sfe I | 5'-CTATAG-3'<br>3'-GATATC-5' |
| | 5'-GACAATTGGTC-3'<br>3'-CTGTTAACAG-5'<br>(SEQ ID NO: 74) | 5'-CCAATAAATGGCTGG-3'<br>3'-GGTTATTTACGGACC-5'<br>(SEQ ID NO: 90) | Mun I | 5'-CAATTG-3'<br>3'-GTTAAC-5' |
| | 5'-GACGATTGGTC-3'<br>3'-CTGCTAACCAG-5'<br>(SEQ ID NO: 75) | 5'-CCAATAAAGGCTGG-3'<br>3'-GGTTATTTACCGAGC-5'<br>(SEQ ID NO: 90) | Mcr I<br>Pvu I | 5'-CGATCG-3'<br>3'-GCTAGC-5' |
| | 5'-GACXCTTGGTC-3'<br>3'-CTGXGAACCAG-5'<br>(X is any base)<br>(SEQ ID NO: 72) | 5'-CCAATAAATGGCTGG-3'<br>3'-GGTTATTTACCGACC-5'<br>(SEQ ID NO: 90) | Ava I<br>Sml I<br>Xho I | 5'-CTCGAG-3'<br>3'-GAGCTC-5' |
| | 5'-GACXCTTGGTC-3'<br>3'-CTGXGAACCAG-5'<br>(X is any base)<br>(SEQ ID NO: 72) | 5'-CCAATAAATGGCTGG-3'<br>3'-GGTTATTTACCGACC-5'<br>(SEQ ID NO: 90) | Pst I<br>Sfe I | 5'-CTGCAG-3'<br>3'-GACGTC-5' |
| | 5'-GACXCTTGGTC-3'<br>3'-CTCXGAACCAG-5'<br>(X is any base)<br>(SEQ ID NO: 72) | 5'-CCAATAAATGGCTGG-3'<br>3'-GGTTATTTACGGACC-5'<br>(SEQ ID NO: 90) | Afl II<br>Sml I | 5'-CTTAAG-3'<br>3'-GAATTC-5' |

TABLE II-continued

| | | | |
|---|---|---|---|
| 5'-GACX<u>A</u>TTGGTC-3'<br>3'-CTGX<u>T</u>AACCAG-5'<br>(X is any base)<br>(SEQ ID NO: 76) | 5'-CCAATAAATGGCTCG-3'<br>3'-GGTTATTTACGGACC-5'<br>(SEQ ID NO: 90) | Cla I | 5'-ATCGAT-3'<br>3'-TAGCTA-5'<br>(X is any base) |
| 5'-GACX<u>A</u>TTGGTC-3'<br>3'-CTGX<u>T</u>AACCAG-5'<br>(X is any base)<br>(SEQ ID NO: 76) | 5'-CCAATAAATCGCTGG-3'<br>3'-GGTTAATTTACCAGAC-5'<br>(SEQ ID NO: 90) | EcoT22I | 5'-ATGGAT-3'<br>3'-TAGGTA-5' |
| 5'-GACX<u>A</u>TTGGTC-3'<br>3'-GTGX<u>T</u>AACCAG-5'<br>(X is any base)<br>(SEQ ID NO: 76) | 5'-CCAATAAATGGCTGG-3'<br>3'-GGTTATTTACCGACC-5'<br>(SEQ ID NO: 90) | PshB I | 5'-ATTAAT-3'<br>3'-TAATA-5' |
| 5'-GAC<u>A</u>TTTGGTC-3'<br>3'-CTG<u>T</u>AAACCAG-5'<br>(SEQ ID NO: 78) | 5'-CCAATAAATGGCTGG-3'<br>3'-GGTTATTTACCGACC-5'<br><u>(SEQ ID NO: 90)</u> | PshB I | 5'-ATTAAT-3'<br>3'-TAATTA-5' |
| 5'-GACX<u>G</u>TTGGTC-3'<br>3'-CTGX<u>C</u>AACCAG-5'<br>(X is any base)<br>(SEQ ID NO: 79) | 5'-CCAATAAATGGCTGG-3'<br>3'-GGTTATTTACGGACC-5'<br>(SEQ ID NO: 90) | Acc I<br>Bst1107 I | 5'-GTATAC-3'<br>3'-CATATG-5' |
| 5'-GACX<u>G</u>TTGGTC-3'<br>3'-CTGX<u>C</u>AACCAG-5'<br>(X is any base)<br>(SEQ ID NO: 79) | 5'-CCAATAAATGGCTGG-3'<br>3'-GGTTATTTACCGACC-5'<br>(SEQ ID NO: 90) | Acc I<br>Hinc II<br>Sal I | 5'-GTCGAC-3'<br>3'-CAGGTG-5' |
| 5'-GACX<u>G</u>TTGGTC-3'<br>3'-CTGX<u>C</u>AACCAG-5'<br>(X is any base)<br>(SEQ ID NO: 79) | 5'-CCAATAAATGGCTGG-3'<br>3'-GGTTATTTACCGACC-5'<br>(SEQ ID NO: 90) | ApaL I<br>Bsp1286 I<br>HgiAI | 5'-CTGCAG-3'<br>3'-CACGTG-5'<br>(X is any base) |
| 5'-GACX<u>G</u>TTGGTC-3'<br>3'-CTGX<u>C</u>AACCAG-5'<br>(X is any base)<br>(SEQ ID NO: 79) | 5'-CCAATAAATGGCTGG-3'<br>3'-GGTTATTTACCGACC-5'<br>(SEQ ID NO: 90) | Hinc II<br>Hpa I | 5'-GTTAAC-3'<br>3'-CAATTG-5' |
| 5'-GACX<u>T</u>TTGGTC-3'<br>3'-CTGX<u>A</u>ACCAG-5'<br>(X is any base)<br>(SEQ ID NO: 80) | 5'-CCAATAAATGGCTGG-3'<br>3'-GGTTATTTACCGACC-5'<br><u>(SEQ ID NO:90)</u> | Psi I | 5'-TTATAA-3'<br>3'-AATAAT-5' |
| 5'-GACX<u>T</u>TTGGTC-3'<br>3'-CTGX<u>A</u>AACCAG-5'<br>(X is any base)<br>(SEQ ID NO: 80) | 5'-CCAATAAATGGCTGG-3'<br>3'-GGTTATTTACCGACC-5'<br>(SEQ ID NO: 90) | Nsp V<br>BspT104I | 5'-TTCGAA-3'<br>3'-AAGCTT-5' |
| 5'-CACX<u>T</u>TGGTC-3'<br>3'-CTGX<u>AA</u>ACCAG-5'<br>(X is any base)<br>(SEQ ID NO: 80) | 5'-CCAATAAATGGCTGG-3'<br>3'-GGTTATTTACCGACC-5'<br>(SEQ ID NO: 90) | Dra I | 5'-TTTAAA-3'<br>3'-AAATTT-5' |
| 5'-GAC<u>A</u>GTTGGTC-3'<br>3'-CTG<u>TC</u>AACCAG-5'<br>(SEQ ID NO: 81) | 5'-CCAATAAAGGCTGG-3'<br>3'-GGTTATTTACCGACC-5'<br>(SEQ ID NO: 90) | Sca I<br>Tat I | 5'-AGTACT-3'<br>3'-TCATGA-5' |
| 5'-GAC<u>C</u>GTTGGTC-3'<br>3'-CTG<u>GC</u>AACCAG-5'<br>(SEQ ID NO: 82) | 5'-CCAATAAATGGCTGG-3'<br>3'-GGTTATTACGACC-5'<br>(SEQ ID NO: 90) | Spl I | 5'-CGTACG-3'<br>3'-GCATGC-5' |
| 5'-GAC<u>G</u>GTTGGTC-3'<br>3'-CTG<u>CC</u>AACCAG-5'<br>(SEQ ID NO: 83) | 5'-CCAATAAATGGCTGG-3'<br>3'-GGTTATTTACCGACC-5'<br>(SEQ ID NO: 90) | BspT107 I<br>HgiC I<br>Kpn I | 5'-GGTACC-3'<br>3'-CCATGG-5' |
| 5'-GAC<u>T</u>GTTGGTC-3'<br>3'-CTG<u>AC</u>AACCAG-5'<br>(SEQ ID NO: 84) | 5'-CCAATAAATGGCTGG-3'<br>3'-GGTTATTTACCGACC-5'<br>(SEQ ID NO: 90) | Bsp1407 I<br>Tat I | 5'-TGTACA-3'<br>3'-ACATGT-5' |
| 5'-GAC<u>A</u>CTTGGTC-3'<br>3'-CTG<u>TG</u>AACCAG-5'<br>(SEQ ID NO: 85) | 5'-CCAATAAATGGCTGG-3'<br>3'-GGTTATTTACCGACC-5'<br>(SEQ ID NO: 90) | Spe I | 5'-ACTAGT-3'<br>3'-TGATCA-5' |
| 5'-GAC<u>CC</u>TTGGTC-3'<br>3'-CTG<u>GG</u>AACCAG-5'<br>(SEQ ID NO: 87) | 5'-CCAATAAATGGCTGG-3'<br>3'-GGTTATTTACCGACC-5'<br>(SEQ ID NO: 90) | Bln I<br>EcoT14I | 5'-CCTAGG-3'<br>3'-GGATCC-5' |

TABLE II-continued

| | | | |
|---|---|---|---|
| 5'-GACGCTTGGTC-3'<br>3'-CTGCGAACCAG-5'<br>(SEQ ID NO: 88) | 5'-CCAATAAATGGCTGG-3'<br>3'-GGTTATTTAGGAGC-5'<br>(SEQ ID NO: 90) | Nhe I | 5'-GCTAGC-3'<br>3'-CGATCG-5' |
| 5'-GACTCTTGGTC-3'<br>3'-CTGAGAACCAG-5'<br>(SEQ ID NO: 89) | 5'-CCAATAAATGGCTGG-3'<br>3'-GGTTATTTACCGACC-5'<br>(SEQ ID NO: 90) | Xba I | 5'-TCTAGA-3'<br>3'-AGATCT-5' |
| 5'-GACAATTGGTC-3'<br>3'-CTGTTAACCAG-5'<br>(SEQ ID NO: 74) | 5'-CCAATAAATGGCTGG-3'<br>3'-GGTTATTTACCGACC-5'<br>(SEQ ID NO: 90) | Ssp I | 5'-AATATT-3'<br>3'-TTATAA-5' |
| 5'-GACGATTGGTC-3'<br>3'-CTGCTAACCAG-5'<br>(SEQ ID NO: 75) | 5'-CCAATAAATGGCTGG-3'<br>3'-GGTTATTTACCGACC-5'<br>(SEQ ID NO: 90) | EcoRV | 5'GATATC-3'<br>3'-CTATAG-5' |

| First restriction enzyme | 5'-end and 3'-end sequences of a foreign gene to be inserted into a vector (large letter "A" represents the base of a nucleotide added in PCR reaction) | Requirement that the 5'-end sequence of front primer for preparing a foreign gene must satisfy | Sequence added to the 5' end of rear primer for preparing a foreign gene (when stop codon is not added) | Sequence added to the 5' end of rear primer for preparing a foreign gene (when stop codon is also added) |
|---|---|---|---|---|
| Ahdt/XccmI | 5'-XXXX-//-XXCCA-3'<br>3'-AXXX-//-XXGG-5'<br>(X is any base) | Not including 5'-CG | 5'-GG | 5'-GGXnTTA<br>(Xn represents any basis in a number of n) |
| | 5'-XXXX-//-XXCATA-3'<br>3'-XXXX-//-XXGTA-5'<br>(X is any base) | Not including 5'-ATG | 5'-ATG | 5'-ATGXnTTA<br>(Xn represents any bases in a number of n) |
| | 5'-XXXX-//-XXCTATA-3'<br>3'-AXXXX-//-XXGATA-5'<br>(X is any base) | Not including 5'-ATAG | 5'-ATAG | 5'-ATAGXnTTA<br>(Xn represents any bases in a number of n) |
| | 5'-XXXX-//-XXCTA-3'<br>3'-AXXXX-//-XXGA-5'<br>(X is any base) | Not including 5'-AG | 5'-AG | 5'-AGXnTTA<br>(xn represents any bases in a number of n) |
| | 5'-XXXX-//-XXCAA-3'<br>3'-AXXX-//-XXGT-5'<br>(X is any base) | Not including 5'-TG | 5'-TG | 5'-TGXnTTA<br>(Xn represents any bases in a number of n) |
| | 5'-XXXX-//-XXGGA-3'<br>3'-AXXXX-//-XXGC-5'<br>(X is any base) | Not including 5'-CG | 5'-CG | (5'-CGXnTTA<br>(Xn represents any bases in a number of n) |
| | 5'-XXXX-//-XXCTCGA-3'<br>3'-AXXXX-//-XXGAGC-5'<br>(X is any base) | Not including 5'-CGAG | 5'-CGAG | 5'-CGAGXnTTA<br>(Xn represents any bases in a number of n) |
| | 5'-XXXX-//-XXTGCA-3'<br>3'-AXXX-//-XXGACG-5'<br>(X is any base) | Not including 5'-GCAG | 5'-GCAG | 5'GCAGXnTTA<br>(Xn represents any bases in a number of n) |
| | 5'-XXXX-//-XXCTTAA-3'<br>3'-AXXXX-//-XXGAAT-5'<br>(X is any base) | Not including 5'-TAAG | 5'-TAAG | 5'-TAAGXnTTA<br>(Xn represents any bases in a number of n) |
| | | Not including 5'-CGAT | 5'-CGAT | 5'-CGATXnTTA<br>(Xn represents any bases in a number of n) |

TABLE II-continued

| | | | |
|---|---|---|---|
| Not including 5'-CGAT | 5'-CGAT | 5'-CGAT | 5'-CGATXnTTA (Xn represents any bases in a number of n) |
| 5'-XXXX-//-XXATTA-3'<br>3'-AXXXX-//-XXTAA-5'<br>(X is any base) | Not including 5'-TAAT | 5'-TAAT | 5'-TAATXnTTA (Xn represents any bases in a number of n) |
| 5'-XXXX-//-XXATTA-3'<br>3'-AXXXX-//-XXTAA-5'<br>(X is any base) | Not including 5'-AAT | 5'-AAT | 5'-AATXXnTTA (Xn represents any bases in a number of n) |
| 5'-XXXX-//-XXGTATA-3'<br>3'-AXXXX-//-XXCATA-5'<br>(X is any base) | Not including 5'-ATAC | 5'-ATAC | 5'-ATACXnTTA (Xn represents any bases in a number of n) |
| 5'-XXXX-//-XXGTCGA-3'<br>3'-AXXXX-//-XXCAGC-5'<br>(X is any base) | Not including 5'-CGAC | 5'-CGAC | 5'-CGACXnTTA (Xn represents any bases in a number of n) |
| 5'-XXXX-//-XXGTGCA-3'<br>3'-AXXXX-//-XXCACG-5'<br>(X is any base) | Not including 5'-GCAC | 5'-GCAC | 5'-GCACXnTTA (Xn represents any bases in a number of n) |
| 5'-XXXX-//-XXGTTAA-3'<br>3'-AXXXX-//-XXCAAT-5'<br>(X is any base) | Not including 5'-TAAC | 5'-TAAC | 5'-TAACXnTTA (Xn represents any bases in a number of n) |
| 5'-XXXX-//-XXTTATA-3'<br>3'-AXXXX-//-XXAATA-5'<br>(X is any base) | Not including 5'-ATAA | 5'-ATAA | 5'-ATAAXnTTA (Xn represents any bases in a number of n) |
| 5'-XXXX-//-XXTTCGA-3'<br>3'-AXXXX-//-XXAAGC-'<br>(X is any base) | Not including 5'-CGAA | 5'-CGAA | 5'-CGAAXnTTA (Xn represents any bases in a number of n) |
| 5'-XXXX-//-XXTTAA-3'<br>3'-AXXX-//-XXAAT-5'<br>(X is any base) | Not including 5'-TAAA | 5'-TAAA | 5'-TAAXnTTA (Xn represents any bases in a number of n) |
| 5'-XXXX-//-XXAGTA-3'<br>3'-AXXXX-//-XXTCA-5'<br>(X is any base) | Not including 5'-ACT | 5'-ACT | 5'-ACTnTTA (Xn represents any bases in a number of n) |
| 5'-XXXX-//-XXCGTA-3'<br>3'-AXXXX-//-XXGCA-5'<br>(X is any base) | Not including 5'-ACG | 5'-ACG | 5'-ACGXnTTA (Xn represents any bases in a number of n) |
| 5'-XXXX-//-XXGGTA-3'<br>3'-AXXXX-//-XXCCA-5'<br>(X is any base) | Not including 5'-ACC | 5'-ACC | 5'-ACCXnTTA (Xn represents any bases in a number of n) |
| 5'-XXXX-//-XXTGTA-3'<br>3'-AXXXX-//-XXACA-5'<br>(X is any base) | Not including 5'-ACA | 5'-ACA | 5'-ACAXnTTA (Xn represents any bases in a number of n) |
| 5'-XXXX-//-XXACTA-3'<br>3'-AXXXX-//-XXTGA-5'<br>(X is any base) | Not including 5'-AGT | 5'-AGT | 5'-AGTXnTTA<br>5'-AGTXnTTA (Xn represents any bases in a number of n) |

TABLE II-continued

| | | |
|---|---|---|
| 5'-XXXX-//-XXCCTA-3'<br>3'-AXXXX-//-XXGGA-5'<br>(X is any base) | Not including 5'-ACG | 5'-ACG<br>5'-ACGXnTTA<br>5'-AGTXnTTA<br>(Xn represents any bases in a number of n) |
| 5'-XXXX-//-XXGCTA-3'<br>3'-AXXXX-//-XXCGA-5'<br>(X is any base) | Not including 5'-AGC | 5'-AGC<br>5'-ACGXnTTA<br>5'-AGTXnTTA<br>(Xn represents any bases in a number of n) |
| 5'-XXXX-//-XXTCTA-3'<br>3'-AXXXX-//-XXAGA-5'<br>(X is any base) | Not including 5'-AGA | 5'-AGA<br>5'-AGAXnTTA<br>5'-AGTXnTTA<br>(Xn represents any bases in a number of n) |
| 5'-XXXX-//-XXAATA-3'<br>3'-AXXXX-//-XXTTA-5'<br>(X is any base) | Not including 5'-ATT | 5'-ATT<br>5'-ATTXnTTA<br>5'-AGTXnTTA<br>(Xn represents any bases in a number of n) |
| 5'-XXXX-//-XXGATA-3'<br>3'-AXXXX-//-XXCTA-5'<br>(X is any base) | Not including 5'-ATC | 5'-ATC<br>5'-ATCXnTTA<br>5'-AGTXnTTA<br>(Xn represents any bases in a number of n) |

TABLE III

| First restriction enzyme | Restriction recognition sequence (i) of first restriction enzyme (comprising a part (underlined portion) of the restriction recognition sequence of second restriction enzyme) | Restriction recognition sequence (ii) of first restriction enzyme (not comprising the part of the restriction recognition sequence of second restriction enzyme) | Second restriction enzyme | Restriction recognition sequence of second restriction enzyme |
|---|---|---|---|---|
| XcmI | 5'-CCAXCCATGGTATGG-3'<br>3'-GGTXGGTACCATACC-5'<br>(SEQ ID NO: 91) | 5'-CCAATAAACCGCTGG-3'<br>3'-GGTTATTTGCCGACC-5'<br>(SEQ ID NO: 98) | NcoI<br>DsaI<br>EcoT14I | 5'-CCATGG-3'<br>3'-GGTACC-5' |
| | 5'-CCAXXCATGGTATGG-3'<br>3'-GGTXXGTAACCTACC-5'<br>(SEQ ID NO: 92) | 5'-CCAATAAACGGCTGG-3'<br>3'-GGTTATTTGCCGACC-5'<br>(SEQ ID NO: 98) | NdeI | 5'-CATATG-3'<br>3'-GTATAC-5 |
| | 5'-CCAXXXCTGGTATGG-3'<br>3'-GGTXXXGACCATACC-5'<br>(SEQ ID NO: 93) | 5'-CCAATAAATGGCTGG-3'<br>3'-GGTTATTTACCGACC-5'<br>(SEQ ID NO: 99) | Sfe I | 5'-CTATAG-3'<br>3'-GATATC-5' |
| | 5'-CCAXCTATGGTATGG-3'<br>3'-GGTXGACACCATACC-5'<br>(SEQ ID NO: 94) | 5'-CCAATAAATGGCTGG-3'<br>3'-GGTTATTTACCGACC-5'<br>(SEQ ID NO: 99) | Sfe I | 5'-CTATAG-3'<br>3'-GATATC-5' |
| | 5'-CCAXCAATGGTATGG-3'<br>3'-GGTXGTTACCATACC-5'<br>(SEQ ID NO: 95) | 5'-CCAATAAATGGCTGG-3'<br>3'-GGTTATTTACCGACC-5'<br>(SEQ ID NO: 99) | Mun I | 5'-CAATTG-3'<br>3'-GTTAAC-5' |
| | 5'-CCAXCGATGGTATGG-3'<br>3'-GGTXGCTACCATACC-5'<br>(SEQ ID NO: 96) | 5'-CCAATAAATGGCTGG-3'<br>3'-GGTTATTTACCGACC-5'<br>(SEQ ID NO: 99) | Mcr I<br>Pvu I | 5'-CGATCG-3'<br>3'-GCTAGC-5' |
| | 5'-CCAXXXCTGGTATGG-3'<br>3'-GGTXXXGACCATACC-5'<br>(SEQ ID NO: 97) | 5'-CCAATAAATGGCTGG-3'<br>3'-GGTTATTTACCGACC-5'<br>(SEQ ID NO: 99) | Ava I<br>Sml I<br>Xho I | 5'-CTCGAG-3'<br>3'-GAGCTC-5' |
| | 5'-CCAXXXCTGGTATGG-3'<br>3'-GGTXXXGACCATACC-5'<br>(SEQ ID NO: 97) | 5'-CCAATAAATGGCTGG-3'<br>3'-GGTTATTTACCGACC-5'<br>(SEQ ID NO: 99) | Pst I<br>Sfe I | 5'-CTGCAG-3'<br>3'-GACGTC-5' |
| | 5'-CCAXXXCTGGTATGG-3<br>3'-GGTXXXGACCATACC-5'<br>(SEQ ID NO: 97) | 5'-CCAATAAATGGCTGG-3'<br>3'-GGTTATTTACCGACC-5'<br>(SEQ ID NO: 99) | Afl II<br>Sml I | 5'-CTTAAG-3'<br>3'-GAATTC-5' |

TABLE III-continued

| | | | |
|---|---|---|---|
| 5'-CCAXXXATGGTATGG-3'<br>3'-GGTXXXTACCATACC-5'<br>(SEQ ID NO: 100) | 5'-CCAATAAACGGCTGG-3'<br>3'-GGTATTTGCCGACC-5'<br>(SEQ ID NO: 105) | Cla I | 5'-ATCGAT-3'<br>3'-TAGCTA-5' |
| 5'-CCAXXXATGGTATGG-3'<br>3'-GGTXXXTACCATACC-5'<br>(SEQ ID NO: 100) | 5'-CAATAAACCGCCTGG-3'<br>3'-GGTATTTGCCGACC-5'<br>(SEQ ID NO: 105) | EcoT22I | 5'-ATGCAT-3'<br>3'-TACGTA-5' |
| 5'-CCAXXXATGGTATGG-3'<br>3'-GGTXXTAACCATACC-5'<br>(SEQ ID NO: 100) | 5'-CCAATAAATGGCTGG-3'<br>3'-GGTATTTGCCGACC-5'<br>(SEQ ID NO: 105) | PshB I | 5'-ATTAAT-3'<br>3'-TAATTA-5' |
| 5'-CCAXXATTGGTATGG-3'<br>3'-GGTXXTAACCATACC-5'<br>(SEQ ID NO: 101) | 5'-CCAATAAATGCCTGG-3'<br>3'-GGTATTTACCGACC-5'<br>(SEQ ID NO: 99) | PshB I | 5'-ATTAAT-3'<br>3'-TAATTA-5' |
| 5'-CCAXXXGTGGTATGG-3'<br>3'-GGTXXXCACCATACC-5'<br>(SEQ ID NO: 102) | 5'-CCAATAAATGGCTGG-3'<br>3'-GGTATTTACCGACC-5'<br>(SEQ ID NO: 99) | Acc I<br>Bst1107I | 5'-GTATAC-3'<br>3'-CATATG-5' |
| 5'-CCAXXXGTGGTATGG-3'<br>3'-GGXXXCACCATACC-5'<br>(SEQ ID NO: 102) | 5'-CCAATAAATGGCTGG-3'<br>3'-GGTATTTACCGACC-5'<br>(SEQ ID NO: 99) | Acc I<br>Hinc II<br>Sal I | 5'-GTCGAC-3'<br>3'-CAGCTG-5' |
| 5'-CCAXXXGTGGTATGG-3'<br>3'-GGTXXXCACCATACC-5'<br>(SEQ ID NO: 102) | 5'-CCAATAAATGGCTGG-3'<br>3'-GGTATTTACCGACC-5'<br>(SEQ ID NO: 99) | ApaL I<br>Bsp1286 I<br>HgiA I | 5'-GTGCAC-3'<br>3'-CACGTG-5' |
| 5'-CCAXXXGTGGTATGG-3'<br>3'-GGTXXXCACCATACC-5'<br>(SEQ ID NO: 102) | 5'-CCAATAAATGGCTGG-3'<br>3'-GGTATTTACCGACC-5'<br>(SEQ ID NO: 99) | Hinc II<br>Hpa I | 5'-GTTAAC-3'<br>3'-CATTG-5' |
| 5'-CCAXXXTTGGTATGG-3'<br>3'-GGTXXXAACCATACC-5'<br>(SEQ ID NO: 103) | 5'-CCAATAAATGGCTGG-3'<br>3'-GGTATTTACCGACC-5'<br>(SEQ ID NO: 99) | Psi I | 5'-TTATAA-3'<br>3'-AATATT-5' |
| 5'-CCAXXXTTGGTATGG-3'<br>3'-GGTXXXAACCATACC-5'<br>(SEQ ID NO: 103) | 5'-CCAATAAATGGCTGG-3'<br>3'-GGTATTTACCGACC-5'<br>(SEQ ID NO: 99) | Nsp V<br>BspT104I | 5'-TTCGAA-3'<br>3'-AAGCTT-5' |
| 5'-CCAXXXTTGGTATGG-3'<br>3'-GGTXXXAACCATACC-5'<br>(SEQ ID NO: 103) | 5'-CCAATAAATGGCTGG-3'<br>3'-GGTATTTACCGACC-5'<br>(SEQ ID NO: 99) | Dra I | 5'-TTTAA-3'<br>3'-AAATTT-5' |
| 5'-CCAXXAGTGGTATGG-3'<br>3'-GGTXXTCACCATACC-5'<br>(SEQ ID NO: 104) | 5'-CCAATAAATGGCTGG-3'<br>3'-GGTATTTACCGACC-5'<br>(SEQ ID NO: 99) | Sca I<br>Tat I | 5'-AGTACT-3'<br>3'-TCATGA-5' |
| 5'-CCAXXCGTGGTATGG-3'<br>3'-GGTXXGCACCATACC-5'<br>+B87<br>(SEQ ID NO: 106) | 5'-CCAATAAATGGCTGG-3'<br>3'-GGTATTTACCGACC-5'<br>(SEQ ID NO: 99) | Spl I | 5'-CGTACG-3'<br>3'-GCATGC-5' |
| 5'-CCAXXGGTGGTATGG-3'<br>3'-GGTXXCCACCATACC-5'<br>(SEQ ID NO: 107) | 5'-CCAATAAATGGCTGG-3'<br>3'-GGTATTTACCGACC-5'<br>(SEQ ID NO: 99) | BspT107I<br>HgiCl<br>Kpn I | 5'-GGTACC-3'<br>3'-CCATGG-5' |
| 5'-CCAXXTGTGGTATGG-3'<br>3'-GGTXXACACCATACC-5'<br>(SEQ ID NO: 108) | 5'-CCAATAAATGGCTGG-3'<br>3'-GGTATTTACCGACC-5'<br>(SEQ ID NO: 99) | Bsp1407 I<br>Tat I | 5'-TGTACA-3'<br>3'-ACATGT-5' |
| 5'-CCAXXACTGGTATGG-3'<br>3'-GGTXXTGACCATACC-5'<br>(SEQ ID NO: 109) | 5'-CCAATAAATGCCTGG-3'<br>3'-GGTATTTACCGACC-5'<br>(SEQ ID NO: 99) | Spe I | 5'-ACTAGT-3'<br>3'-TGATCA-5' |
| 5'-CCAXXCCTGGTATGG-3'<br>3'-GGTXXGGACCATACC-5'<br>(SEQ ID NO: 110) | 5'-CCAATAAATGGCTGG-3'<br>3'-GGTATTTACCGACC-5'<br>(SEQ ID NO: 99) | Bln I<br>EcoT14I | 5'-CCTAGG-3'<br>3'-GATCC-5' |
| 5'-CCAXXGCTGGTATGG-3'<br>3'-GGTXXCCACCATAAC-5'<br>(SEQ ID NO: 111) | 5'-CCAATAAATGGCTGG-3'<br>3'-GGTATTTACCGACC-5'<br>(SEQ ID NO: 99) | Nhe I | 5'-GCTAGC-3'<br>3'-CGATCG-5' |
| 5'-CCAXXTCTGGTATGG-3'<br>3'-GGTXXAGACCATACC-5'<br>(SEQ ID NO: 112) | 5'-CCAATAAATGGCTGG-3'<br>3'-GGTATTTACCGACC-5'<br>(SEQ ID NO: 99) | Xba I | 5'-TCTAGA-3'<br>3'-AGATCT-5' |
| 5'-CCAXXAATGGTATGG-3'<br>3'-GGTXXTTACCATACC-5'<br>(SEQ ID NO: 113) | 5'-CCAATAAATGGCTGG-3'<br>3'-GGTATTTACCGACC-5'<br>(SEQ ID NO: 99) | Ssp I | 5'-AATATT-3'<br>3'-TTATAA-5' |

TABLE III-continued

| | | | |
|---|---|---|---|
| 5'-CCAXX<u>GA</u>TGGTATGG-3'<br>3'-GGTXX<u>CT</u>ACCATACC-5'<br>(SEQ ID NO: 114) | 3'-CCAATAAATGGCTGG-3'<br>3'-GGTTATTTACCGACC-5'<br>(SEQ ID NO: 99) | EcoRV | 5'-GATATC-3'<br>3'-CTATAG-5' |
| 5'-CCX<u>AAA</u>TGGTATGG-3'<br>3'-GGTX<u>TTT</u>ACCATACC-5'<br>(SEQ ID NO: 115) | 5'-CCAATAAACGGCTGG-3'<br>3'-GGTTATTTGCCGACC-5'<br>(SEQ ID NO: 105) | Apo I | 5'-AAATTT-3'<br>3'-TTTAAA-5' |
| 5'-CCAX<u>GAA</u>TGGTATGG-3'<br>3'-GGTX<u>CTT</u>ACCATACC-5'<br>(SEQ ID NO: 116) | 5'-CCAATAAACGGCTGG-3'<br>3'-GGTTATTTGCCGACC-5'<br>(SEQ ID NO: 105) | Apo I<br>EcoR I | 5'-GAATTC-3'<br>3'-CTTAAG-5' |
| 5'-CCAX<u>ACA</u>TGGTATGG-3'<br>3'-GGTX<u>TGT</u>ACCATACC-5'<br>(SEQ ID NO: 117) | 5'-CCAATAAACGGCTGG-3'<br>3'-GGTTATTTGCCGACC-5'<br>(SEQ ID NO: 105) | Afl III<br>BspLU11 I<br>Nsp I | 5'-ACATGT-3'<br>3'-TGTACA-5' |
| 5'-CCAX<u>GCA</u>TGGTATGG-3'<br>3'-GGTX<u>CGT</u>ACCATACC-5'<br>(SEQ ID NO: 118) | 5'-CCAATAAACGGCTGG-3'<br>3'-GGTTATTTGCCGACC-5'<br>(SEQ ID NO: 105) | Nsp I<br>Sph I | 5'-GCATGC-3'<br>3'-CGTACG-5' |
| 5'-CCAX<u>TCA</u>TGGTATGG-3'<br>3'-GGTX<u>AGT</u>ACCATACC-5'<br>(SEQ ID NO: 119) | 5'-CCAATAAACGGCTGG-3'<br>3'-GGTTATTTGCCGACC-5'<br>(SEQ ID NO: 105) | BspH I | 5'-TCATGA-3'<br>3'-AGTACT-5' |
| 5'-CCAX<u>AGA</u>TGGTATGG-3'<br>3'-GGTX<u>TCT</u>ACCATACC-5'<br>(SEQ ID NO: 120) | 5'-CCAATAAACGGCTGG-3'<br>3'-GGTTATTTGCCGACC-5'<br>(SEQ ID NO: 105) | Bgl II<br>Mfl I | 5'-AGATCT-3'<br>3'-AGTACT-5' |
| 5'-CCAX<u>GGA</u>TGGTATGG-3'<br>3'-CGTX<u>CCT</u>ACCATACC-5'<br>(SEQ ID NO: 121) | 5'-CCAATAAACGGCTGG-3'<br>3'-GGTTATTTGCCGACC-5'<br>(SEQ ID NO: 105) | BamH I<br>Mfl I | 5'-GGATCC-3'<br>3'-CCTAGG-5' |
| 5'-CCAX<u>TGA</u>TGGTATGG-3'<br>3'-GGTX<u>ACT</u>ACCATACC-5'<br>(SEQ ID NO: 122) | 5'-CCAATAAACGGCTGG-3'<br>3'-GGTTATTTGCCGACC-5'<br>(SEQ ID NO: 105) | Fba I | 5'-TGATCA-3'<br>3'-ACTAGT-5' |
| 5'-CCAX<u>GTA</u>TGGTATGG-3'<br>3'-GGTX<u>CAT</u>ACCATACC-5'<br>(SEQ ID NO: 123) | 5'-CCAATAAACGGCTGG-3'<br>3'-GGTTATTTGCCGACC-5'<br>(SEQ ID NO: 105) | Acc I<br>Bst1107 I | 5'-GTATAC-3'<br>3'-CATATG-5' |
| 5'-CCAX<u>TTA</u>TGGTATGG-3'<br>3'-GGTX<u>AAT</u>ACCATACC-5'<br>(SEQ ID NO: 124) | 5'-CCAATAAACGGCTGG-3'<br>3'-GGTTATTTGCCGACC-5'<br>(SEQ ID NO: 105) | Psi I | 5'-TTATAA-3'<br>3'-AATATT-5' |
| 5'-CCA<u>AACGT</u>GGTATGG-3'<br>3'-GGT<u>TTGCA</u>CCATACC-5'<br>(SEQ ID NO: 125) | 5'-CCAATAAACGGCTGG-3'<br>3'-GGTTATTTGCCGACC-5'<br>(SEQ ID NO: 105) | Psp1406 I | 5'-AACGTT-3'<br>3'-TTGCAA-5' |
| 5'-CCA<u>CACGT</u>GGTATGG-3'<br>3'-GGT<u>GTGCA</u>CCATACC-5'<br>(SEQ ID NO: 126) | 5'-CCAATAAACGGCTGG-3'<br>3'-GGTTATTTGCCGACC-5'<br>(SEQ ID NO: 105) | BsaA I<br>PmaC I | 5'-CACGTG-3'<br>3'-GTGCAC-5' |
| 5'-CCA<u>GACGT</u>GGTATGG-3'<br>3'-GGT<u>CTGCA</u>CCATACC-5'<br>(SEQ ID NO: 127) | 5'-CCAATAAACGGCTGG-3'<br>3'-GGTTATTTGCCGACC-5'<br>(SEQ ID NO: 105) | Aat II<br>Hin1 I | 5'-GACGTC-3'<br>3'-CTGCAG-5' |
| 5'-CCA<u>TACGT</u>GGTATGG-3'<br>3'-GGT<u>TAGCA</u>CCATACC-5'<br>(SEQ ID NO: 128) | 5'-CCAATAAACGGCTGG-3'<br>3'-GGTTATTTGCCGACC-5'<br>(SEQ ID NO: 105) | BsaA I<br>SnaB I | 5'-TACGTA-3'<br>3'-ATGCAT-5' |
| 5'-CCA<u>AAGCT</u>GGTATGG-3'<br>3'-GGT<u>TTCGA</u>CCATACC-5'<br>(SEQ ID NO: 129) | 5'-CCAATAAACGGCTGG-3'<br>3'-GGTTATTTGCCGACC-5'<br>(SEQ ID NO: 105) | Hind III | 5'-AAGCTT-3'<br>3'-TTCGAA-5' |
| 5'-CCA<u>CACCT</u>GGTATGG-3'<br>3'-GGT<u>GTCGA</u>CCATACC-5'<br>(SEQ ID NO: 130) | 5'-CCAATAAACGGCTGG-3'<br>3'-GGTTATTTGCCGACC-5'<br>(SEQ ID NO: 105) | NspB II<br>Pvu II | 5'-CAGCTG-3'<br>3'-GTCGAC-5' |
| 5'-CCA<u>GAGCT</u>GGTATGG-3'<br>3'-GGT<u>CTCGA</u>CCATACC-5'<br>(SEQ ID NO: 131) | 5'-CCAATAAACGGCTGG-3'<br>3'-GGTTATTTGCCGACC-5'<br>(SEQ ID NO: 105) | Ban II<br>Bsp1286 I<br>HgiA I<br>Sac I | 5'-GAGCTC-3'<br>3'-CTCGAG-5' |

TABLE III-continued

| First restriction enzyme | 5'-end and 3'-end sequences of a foreign gene to be inserted into a vector (large letter "A" represents the base of a nucleotide added in PCR reaction) | Requirement that the 5'-end sequence of front primer for preparing a foreign gene must satisfy | Sequence added to the 5' end of rear primer for preparing a foreign gene (when stop codon is not added) | Sequence added to the 5' end of rear primer for preparing a foreign gene (when stop codon is also added) |
|---|---|---|---|---|
| XcmI | 5'-XXXX-//-XXCCA-3'<br>3'-AXXXX-//-XXGG-5'<br>(X is any base) | Not including 5'-GG | 5'-GG | 5'-GGXnTA<br>(Xn represents any bases in a number of n) |
| | 5'-XXXX-//-XXCATA-3'<br>3'-AXXXX-//-XXGTA-5'<br>(X is any base) | Not including 5'-ATG | 5'-ATG | 5'-ATGXnTTA<br>(Xn represents any bases in a number of n) |
| | 5'-XXXX-//-XXCTATA-3'<br>3'-AXXXX-//-XXGATA-5'<br>(X is any base) | Not including 5'-ATAG | 5'-ATAG | 5'-ATAGXnTTA<br>(Xn represents any bases in a number of n) |
| | 5'-XXXX-//-XXCTA-3'<br>3'-AXXXX-//-XXGA-5'<br>(X is any base) | Not including 5'-AG | 5'-AG | 5'-AGXnTTA<br>(Xn represents any bases in a number of n) |
| | 5'-XXXX-//-XXCAA-3'<br>3'-AXXXX-//-XXGT-5'<br>(X is any base) | Not including 5'-TG | 5'-TG | 5'-TGXnTTA<br>(Xn represents any bases in a number of n) |
| | 5'-XXXX-//-XXCGA-3'<br>3'-AXXXX-//-XXGC-5'<br>(X is any base) | Not including 5'-CG | 5'-CG | 5'-CGXnTTA<br>(Xn represents any bases in a number of n) |
| | 5'-XXXX-//-XXCTCGA-3'<br>3'-AXXXX-//-XXGAGC-5'<br>(X is any base) | Not including 5'-CGAG | 5'-CGAG | 5'-CGAGXnTTA<br>(Xn represents any bases in a number of n) |
| | 5'-XXXX-//-XXCTGCA-3'<br>3'-AXXXX-//-XXGACG-5'<br>(X is any base) | Not including 5'-GCAG | 5'-GCAG | 5'-GCAGXnTTA<br>(Xn represents any bases in a number of n) |
| | 5'-XXXX-//-XXCTTAA-3'<br>3'-AXXXX-//-XXGAAT-5'<br>(X is any base) | Not including 5'-TAAG | 5'-TAAG | 5'-TAAGXnTTA<br>(Xn represents any bases in a number of n) |
| | 5'-XXXX-//-XXATCGA-3'<br>3'-AXXX-//-XXTAGC-5'<br>(X is any base) | Not including 5'-CGAT | 5'-CGAT | 5'-CGATXnTTA<br>(Xn represents any bases in a number of n) |
| | 5'-XXXX-//-XXATGCA-3'<br>3'-AXXX-//-XXTACG-5'<br>(X is any base) | Not including 5'-GCAT | 5'-GCAT | 5'-GCATXnTTA<br>(Xn represents any bases in a number of n) |
| | 5'-XXXX-//-XXATTA-3'<br>3'-AXXX-//-XXTAAT-5'<br>(X is any base) | Not including 5'-TAAT | 5'-TAAT | 5'-TAATXnTTA<br>(Xn represents any bases in a number of n) |
| | 5'-XXXX-//-XXATTA-3'<br>3'-AXXX-//-XXTAA-5'<br>(X is any base) | Not including 5'-AAT | 5'-AAT | 5'-AATXnTTA<br>(Xn represents any bases in a number of n) |

TABLE III-continued

| | | |
|---|---|---|
| 5'-XXXX-//-XXGTATA-3'<br>3'-AXXX-//-XXCATA-5'<br>(X is any base) | Not including<br>5'-ATAC | 5'-ATACXnTTA<br>(Xn represents any bases in a number of n) |
| 5'-XXXX-//-XXGTCGA-3'<br>3'-AXXX-//-XXCAGC-5'<br>(X is any base) | Not including<br>5'-GCAC | 5'-CGACXnTTA<br>(Xn represents any bases in a number of n) |
| 5'-XXXX-//-XXGTGCA-3'<br>3'-AXXX-/-XXCACG-5'<br>(X is any base) | Not including<br>5'-GCAC | 5'-GCACXnTTA<br>(Xn represents any bases in a number of n) |
| 5'-XXXX-//-XXGTTAA-3'<br>3'-AXXX-//-XXCATA-5'<br>(X is any base) | Not including<br>5'-TAAC | 5'-TAACXnTTA<br>(Xn represents any bases in a number of n) |
| 5'-XXXX-//-XXTTATA-3'<br>3'-AXXX-//-XXAATA-5'<br>(X is any base) | Not including<br>5'-ATAA | 5'-ATAAXnTTA<br>(Xn represents any bases in a number of n) |
| 5'-XXXX-//-XXTTCGA-3'<br>3'-AXXX-//-XXAAGC-5'<br>(X is any base) | Not including<br>5'-CGAA | 5'-CGAAXnTTA<br>(Xn represents any bases in a number of n) |
| 5'-XXXX-//-XXTTAA-3'<br>3'-AXXX-//-XXAAAT-5'<br>(X is any base) | Not including<br>5'-TAAA | 5'-TAAAXnTTA<br>(Xn represents any bases in a number of n) |
| 5'-XXXX-//-XXAGTA-3'<br>3'-AXXX-//-XXTCA-5'<br>(X is any base) | Not including<br>5'-ACT | 5'-ACTXnTTA<br>(Xn represents any bases in a number of n) |
| 5'-XXXX-//-XXCGTA-3'<br>3'-AXXX-//-XXGCA-5'<br>(X is any base) | Not including<br>5'-ACG | 5'-ACGXnTTA<br>(Xn represents any bases in a number of n) |
| 5'-XXXX-//-XXGGTA-3'<br>3'-AXXX-//-XXCCA-5'<br>(X is any base) | Not including<br>5'-ACC | 5'-ACCXnTTA<br>(Xn represents any bases in a number of n) |
| 5'-XXXX-//-XXTGTA-3'<br>3'-AXXX-//-XXACA-5'<br>(X is any base) | Not including<br>5'-ACA | 5'-ACAXnTTA<br>(Xn represents any bases in a number of n) |
| 5'-XXXX-//-XXACTA-3'<br>3'-AXXX-//-XXTGA-5'<br>(X is any base) | Not including<br>5'-AGT | 5'-AGTXnTTA<br>(Xn represents any bases in a number of n) |
| 5'-XXXX-//-XXCCTA-3'<br>3'-AXXX-//-XXGGA-5'<br>(X is any base) | Not including<br>5'-AGG | 5'-AGGXnTTA<br>(Xn represents any bases in a number of n) |
| 5'-XXXX-//-XXGCTA-3'<br>3'-AXXX-//-XXCGA-5'<br>(X is any base) | Nothing including<br>5'-AGC | 5'-AGCXnTTA<br>(Xn represents any bases in a number of n) |
| 5'-XXXX-//-XXTCTA-3'<br>3'-AXXXX-//-XXAGA-5'<br>(X is any base) | Not including<br>5'-AGA | 5'-AGAXnTTA<br>(Xn represents any bases in a number of n) |
| 5'-XXXX-//-XXAATA-3'<br>3'-AXXXX-//-XXTTA-5'<br>(X is any base) | Not including<br>5'-ATT | 5'-ATTXnTTA<br>(Xn represents any bases in a number of n) |

TABLE III-continued

| | | |
|---|---|---|
| 5'-XXXX-//-XXGATA-3'<br>3'-AXXX-//-XXCTA-5'<br>(X is any base) | Not including 5'-ATC<br>5'-ATC | 5'-ATCXnTTA<br>(Xn represents any bases in a number of n) |
| 5'-XXXX-//-XXAAA-3'<br>3'-AXXX-//-XXTT-5<br>(X is any base) | Not including 5'-TT<br>5'-TT | 5'-TTXnTTA<br>(Xn represents any bases in a number of n) |
| 5'-XXXX-//-XXGAA-3'<br>3'-AXXXX-//-XXCT-5'<br>(X is any base) | Not including 5'-TC<br>5'-TC | 5'-TCXnTTA<br>(Xn represents any bases in a number of n) |
| 5'-XXXX-//-XXACA-3'<br>3'-AXXX-//-XXTG-5'<br>(X is any base) | Not including 5'-GT<br>5'-GT | 5'-GTXnTTA<br>(Xn represents any bases in a number of n) |
| 5'-XXXX-//-XXGCA-3'<br>3'-AXXX-//XXGC-5'<br>(X is any base) | Not including 5'-GC<br>5'-GC | 5'-GCXnTTA<br>(Xn represents any bases in a number of n) |
| 5'-XXXX-//-XXTCA-3'<br>3'-AXXX-//-XXAG-5'<br>(X is any base) | Not including 5'-GA<br>5'-GA | 5'-GAXnTTA<br>(Xn represents any bases in a number of n) |
| 5'-XXXX-//-XXAGA-3'<br>3'-AXXXX-//-XXTC-5'<br>(X is any base) | Not including 5'-CT<br>5'-CT | 5'-CTXnTTA<br>(Xn represents any bases in a number of n) |
| 5'-XXXX-//-XXGGA-3'<br>3'-AXXXX-//-XXCC-5'<br>(X is any base) | Not including 5'-CC<br>5'-CC | 5'-CTXnTTA<br>(Xn represents any bases in a number of n) |
| 5'-XXXX-//-XXTGA-3'<br>3'-AXXXX-//-XXAC-5'<br>(X is any base) | Not including 5'-CA<br>5'-CT | 5'-CAXnTTA<br>(Xn represents any bases in a number of n) |
| 5'-XXXX-//-XXGTA-3'<br>3'-AXXXX-//-XXCA-5'<br>(X is any base) | Not including 5'-AC<br>5'-AC | 5'-ACXnTTA<br>(Xn represents any bases in a number of n) |
| 5'-XXXX-//-XXTTA-3'<br>3'-AXXXX-//-XXAA-5'<br>(X is any base) | Not including 5'-AA<br>5'-AA | 5'-AAXnTTA<br>(Xn represents any bases in a number of n) |
| 5'-XXXX-//-XXXAA-3'<br>3'-AXXXX-//-XXXT-5'<br>(X is any base) | Not including 5'-T<br>5'-T | 5'-TXnTTA<br>(Xn represents any bases in a number of n) |
| 5'-XXXX-//-XXXCA-3'<br>3'-AXXXX-//-XXXG-5'<br>(X is any base) | Not including 5'-G<br>5'-G | 5'-GXnTTA<br>(Xn represents any bases in a number of n) |
| 5'-XXXX-//-XXXGA-3'<br>3'-AXXXX-//-XXXC-5'<br>(X is any base) | Not including 5'-C<br>5'-C | 5'-CXnTTA<br>(Xn represents any bases in a number of n) |
| 5'-XXXX-//-XXXTA-3'<br>3'-AXXXX-//-XXXA-5'<br>(X is any base) | Not including 5'-A<br>5'-A | 5'-AXnTTA<br>(Xn represents any bases in a number of n) |
| 5'-XXXX-//-XXXAA-3'<br>3'-AXXXX-//-XXXT-5'<br>(X is any base) | Not including 5'-T<br>5'-T | 5'-TXnTTA<br>(Xn represents any bases in a number of n) |

TABLE III-continued

| | | |
|---|---|---|
| 5'-XXXX-//-XXXCA-3'<br>3'-AXXXX-//-XXXG-5'<br>(X is any base) | Not including 5'-G<br>5'-G | 5'-GXnTTA<br>(Xn represents any bases in a number of n) |
| 5'-XXXX-//-XXXGA-3'<br>3'-AXXXX-//-XXXC-5'<br>(X is any base) | Not including 5'-C<br>5'-C | 5'-CXnTTA<br>(Xn represents any bases in a number of n) |

When the first restriction enzyme is AhdI or an isoschizomer thereof, XcmI or an isoschizomer thereof, or a combination thereof, it is effective to select NcoI, NdeI or an isoschizomer thereof as the second restriction enzyme.

By using the vector of the present invention, it is possible to construct a library which is capable of expressing, as fusion proteins, partial sequences of a protein of interest different in location and/or length in the original protein. For example, a primer mixture is designed and used to amplify partial sequences of a protein of interest using the cDNA of the protein as a template; then, the resultant mixture of DNA fragments encoding partial sequences of the protein are ligated downstream of another protein (for example, see FIG. 3).

Figure 3:
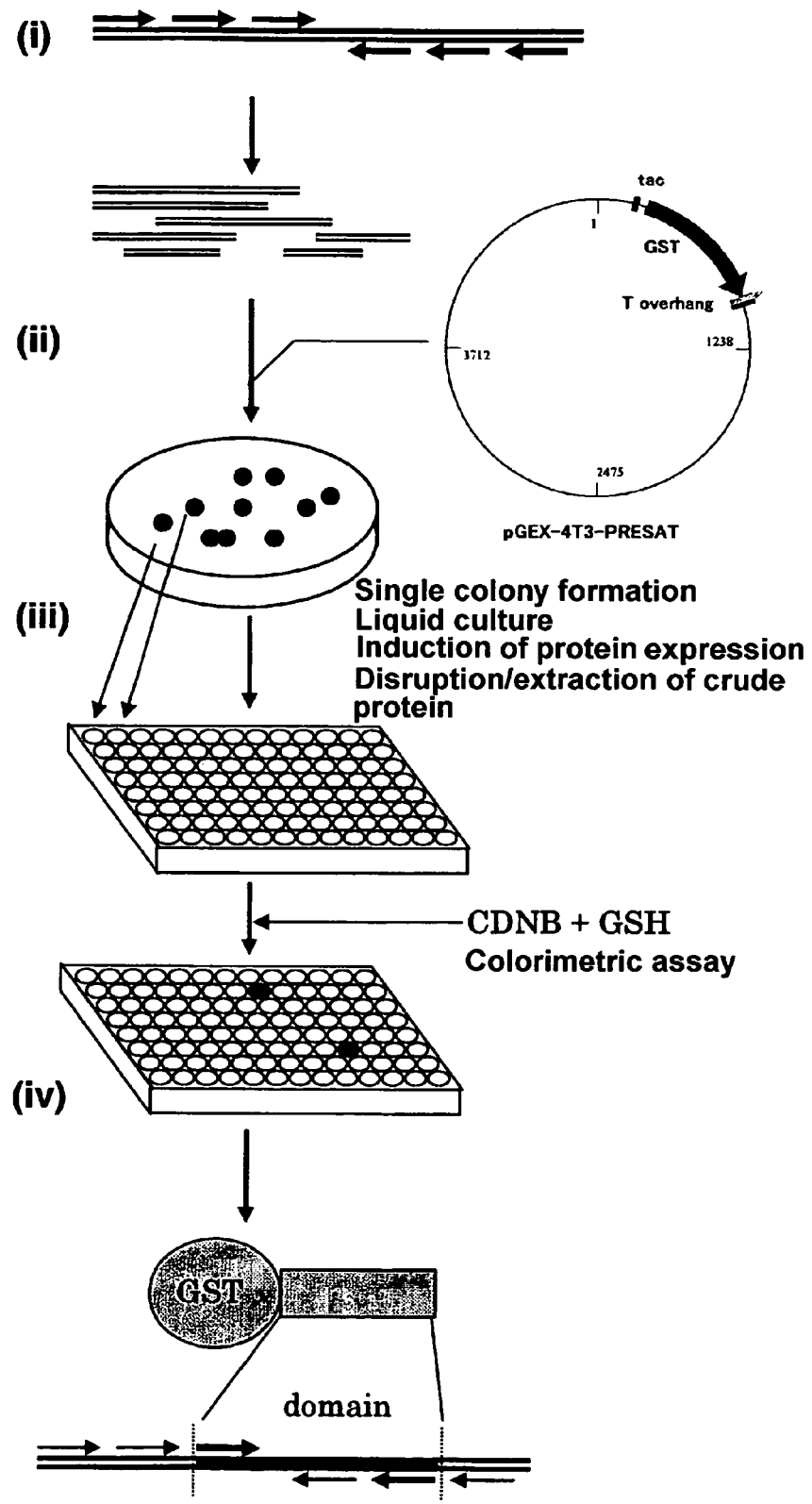
FIG. 3 is a scheme of a high-throughput method of determining the domain boundary of soluble protein domains using a dGST-T vector. (i) Various PCR primers are designed and used to amplify a series of partial cDNA fragments of interest which are presumed to contain a protein domain. (ii) These fragments are inserted into pGEX-4T3-PRESAT, which is then selected for ORF orientation with NcoI or NdeI and transformed into *E. coli* for colony isolation. (iii) Individual colonies are cultured in 96-well plates to allow expression of the protein of interest and/or protein domain of interest with varied lengths as GST-fusion proteins. (iv) The quantities of the fusion proteins are determined by CDNB color development assay. Those clones expressing high levels of GST-fusion protein are selected for further analysis.

Further, by using the vector of the present invention, it becomes possible to create a great number of protein and/or protein domain expression systems in parallel, for example, in 96-well microtiter plates, and to assay the solubility of the proteins and/or protein domains produced by such expression systems in parallel or select only those proteins and/or protein domains with high solubility at high speed (for example, see FIG. 3).

Further, the above-described method using the vector of the present invention and 96-well microtiter plates is capable of creating a great number of protein and/or protein domain expression systems in parallel and also conducting fully automated high-throughput selection of highly soluble proteins and/or protein domains produced, by applying automated colony isolation equipment, automated reagent dispensing/washing equipment capable of handling 96-well microtiter plates or laboratory automation equipment.

Figure 7:
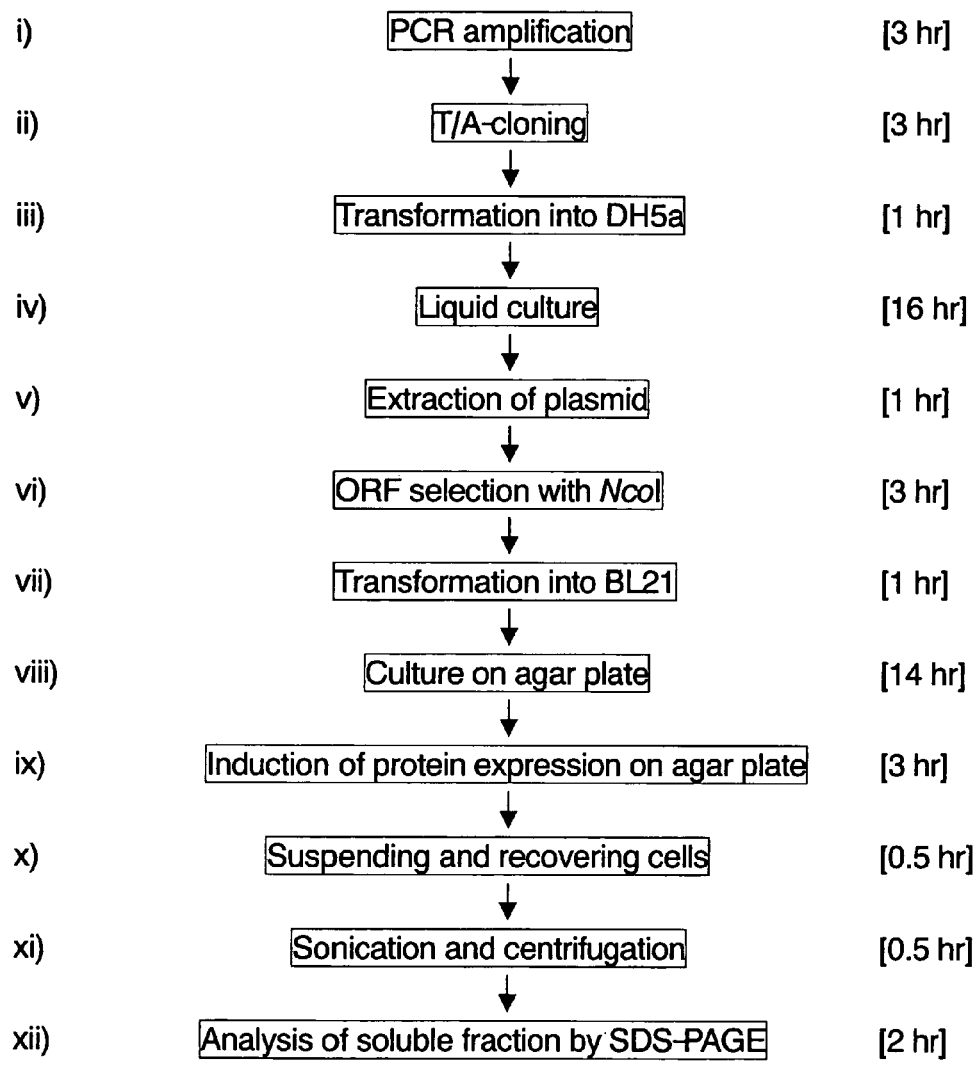
FIG. 7 is a scheme of a high-throughput solubility test for protein domains using a dGST-T vector. Approximate time required for each of the indicated operations is given in [ ]. (i) Specific PCR primers are designed and used to amplify a partial cDNA fragment of interest. This partial cDNA fragment may be any partial sequence presumed to contain the entire protein or the protein domain of interest. (ii) This fragment is inserted into pGEX-4T3-PRESAT followed by ligation. (iii) The resultant plasmid is transformed into $E.$ $coli$ DH5a. (iv) Liquid culture is conducted. (v) The plasmid is isolated and purified. (vi) The plasmid is digested with NcoI or NdeI for ORF selection. (vii) The selected plasmid is transformed into $E.$ $coli$ BL21 to (viii) allow formation of $E.$ $coli$ colonies. (ix) IPTG solution is sprayed thereto for inducing protein expression. (x) $E.$ $coli$ cells on agar medium are suspended and collected. (xi) Cells are disrupted to obtain total cell lysate, soluble fraction and insoluble fraction. (xii) SDS-PAGE is conducted to judge the quantity of GST-fusion protein contained in the soluble fraction based on the thickness of the band on the stained gel. The total time required for the entire process from (i) to (xii) is approximately 48 hours.

Further, by using the vector of the present invention, it becomes possible to judge whether or not a fusion protein comprising a specific single protein and/or protein domain of interest is capable of expression in *E. coli*, or whether or not the fusion protein is soluble, in 48 hours from the start of PCR reaction at the shortest (for example, see FIG. 7).

EXAMPLES

Hereinbelow, the present invention will be described specifically with reference to the following Examples. It should be noted that these Examples are provided only for the purpose of explanation and do not limit the scope of the present invention.

Restriction enzymes NcoI, NdeI, AhdI and AflII were purchased from New England Biolabs. Restriction enzymes KpnI and BamHI were purchased from Toyobo. T4 DNA ligase, Wizard plasmid miniprepkit and Wizard SV DNA gel purification kit were purchased from Promega. pGEM-T, pGEX-4T3 and pGEX-3X; pET32a; and pET21b were purchased from Promega, Amersham Pharmacia Biotech and Novagen, respectively. pET32aPACAP is a pET32a derivative prepared by inserting pET32a-derived thioredoxin gene-containing NdeI fragment into the NdeI site of pET21b and inserting PACAP artificial gene into the NheI site of the same pET21b. As cDNAs to be used as templates for PCR cloning, QUICK-Clone cDNAs of mouse spleen, mouse embryo and human HeLa cells were purchased from Clontech.

Example 1

Preparation of dGST-T Vector (FIG. 1)

Mutation was introduced into pGEX-4T3 vector using a 5' phosphorylated DNA represented by the sequence of SEQ ID NO: 21 by site-directed mutagenesis. As a result of this mutagenesis, the AhdI restriction enzyme site which pGEX-4T3 originally had in its sequence becomes uncleavable. Subsequently, PCR reaction was performed using pET32aPACAP vector as a template and a pair of primers represented by the sequences of SED ID NOS: 22 and 24. The resultant PCR product (approx. 500 bp, the sequence of one of the two DNA strands is shown in SEQ ID NO: 25) had an AhdI site linked to each of the two BamHI sites (FIG. 1). This PCR product was subcloned into a TA cloning vector pTEM-T. After confirmation of the sequence, the plasmid was purified. The purified plasmid was digested with restriction enzyme BamHI, followed by purification of an approx. 500 bp fragment (AhdI linker, SEQ ID NOS: 26 and 27). The mutation introduced pGEX-4T3 described above was linearized with BamHI, dephosphorylated and ligated to the above-described AhdI linker. The resultant plasmid was transformed into *E. coli*. After confirmation of the sequence, those transformants in which AhdI linker was introduced downstream of GST gene in the proper orientation were selected. Approximately 2 µg of the vector into which AhdI linker was introduced downstream of GST gene in the proper orientation was treated with 25 units of AhdI restriction enzyme at 37° C. for 3 hours for digestion, followed by purification using 1% agarose gel. Using Wizard SV gel/PCR clean-up system, an open circular vector of approx. 5 kb (pGEX-4T3-PRERSAT; FIG. 1) was purified and used in the following Examples.

Example 2

Figure 2:
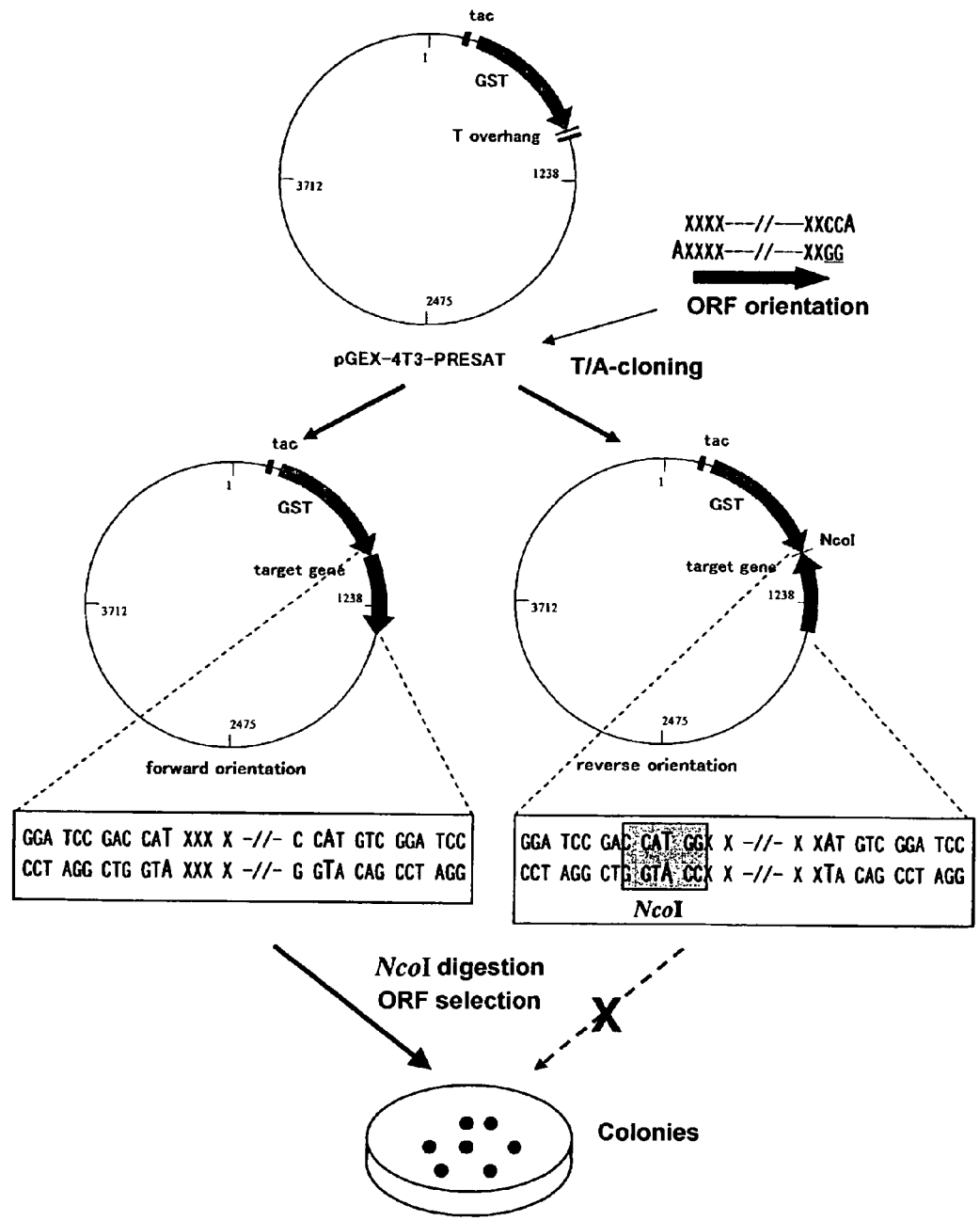
FIG. 2 shows the principle of the selection of ORF orientation.

Preparation of Novel Expression Systems by Parallel Operation (FIG. 2)

First, using primers appropriate for NcoI selection, five types of genes [regions comprising five MIT domains of SNX15a (human and mouse) and Vps4b (yeast, mouse and human); SEQ ID NOS: 28, 30, 32, 34 and 36] were amplified simultaneously and in parallel by PCR using appropriate cDNAs as templates. The primers used (SEQ ID NOS: 38-47) were appropriately designed so that they comprise a sequence complementary to a specific region of the cDNA of the relevant gene to be expressed as a protein, a complementary sequence to the stop codon, and GG residues at 5'-end to perform NcoI selection. Briefly, front primers must start with the first amino acid codon so that the reading frame coincides with that of the preceding GST, and the 5'-end nucleotides of front primers must not start with 5'-GG. Rear primers must contain a stop codon after the boundary of the presumed C terminal region of the relevant domain, and the 5'-end nucleotides of rear primers must start with 5'-GG. As a result, the PCR product amplified with these primers has an NcoI site (a site for the second restriction enzyme) generated only when it has been ligated to pGEX-4T3-PRESAT in the opposite orientation. This newly generated NcoI site is used in the subsequent selection step.

Any of the above-described genes is a 200-230 bp cDNA corresponding to a novel protein domain and encodes about 70 amino acid residues.

Figure 4:
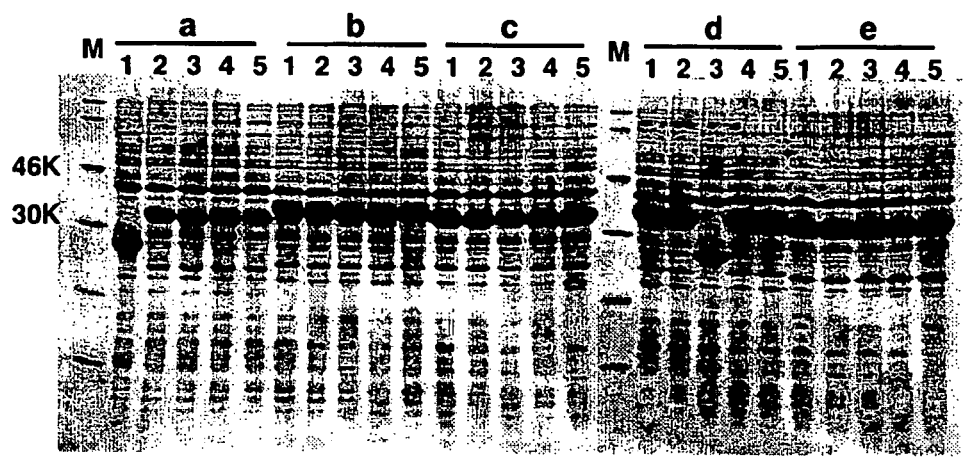

PCR amplification of a gene of interest was confirmed by electrophoresis. Then, the PCR product was ligated unpurified to pGEX-4T3-PRESAT vector, which was transformed into E. coli DH5a. The transformed DH5a was liquid cultured overnight without formation of single colonies. Next day, 1-3 μg of plasmid was purified from the resultant culture. This plasmid was digested with restriction enzyme NcoI and transformed into an expression host E. coli BL21 (DE3), which was then allowed to form single colonies. From the plates carrying single colonies, 3 single colonies for each of the genes were picked (3×5=15) and liquid cultured in LB medium. When OD reached about 0.5, IPTG was added to give a final concentration of 1 mM, and cells were cultured for another 4 hours. E. coli cells after completion of expression were harvested and sonicated. Then, the total cell was analyzed by SDS-PAGE, followed by confirmation of the band of the protein of interest (approx. 33-35 kD) on the gel (FIG. 4) (expression test). Of those colonies obtained, more than 90% of them (14/15) expressed a relevant fusion protein of interest with a predicted molecular weight, showing an extremely high efficiency.

Figure 5:
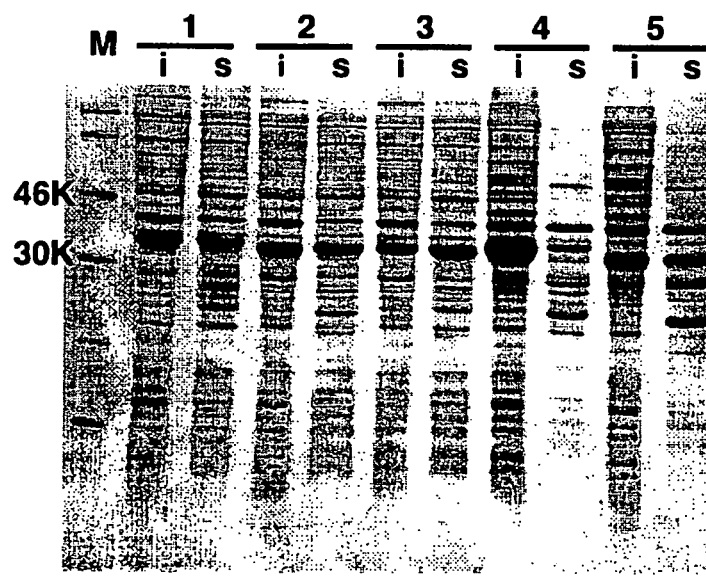
FIG. 5 shows the results of analysis of the solubility of GST-fusion proteins immediately after cell disruption, with 15% SDS-PAGE. Lane M represents molecular weight standards; lanes i1-s1 represent yeast Vps4; lanes i2-s2 represent human Vps4; lanes i3-s3 represent mouse Vps4; lanes i4-s4 represent human Snx15a; and lanes i5-s5 represent mouse Snx15a. Lanes marked with "i" are insoluble fractions and lanes marked with "s" are soluble fractions.

Subsequently, disrupted cells derived from those colonies in which the expression of a fusion protein of interest with a predicted molecular weight had been confirmed were separated into solubilized fraction and insolubilized fraction by centrifugation. These two fractions and the total cell fraction were separately analyzed by SDS-PAGE to examine whether the fusion protein of interest was soluble or not (FIG. 5) (solubility test).

Figure 6:
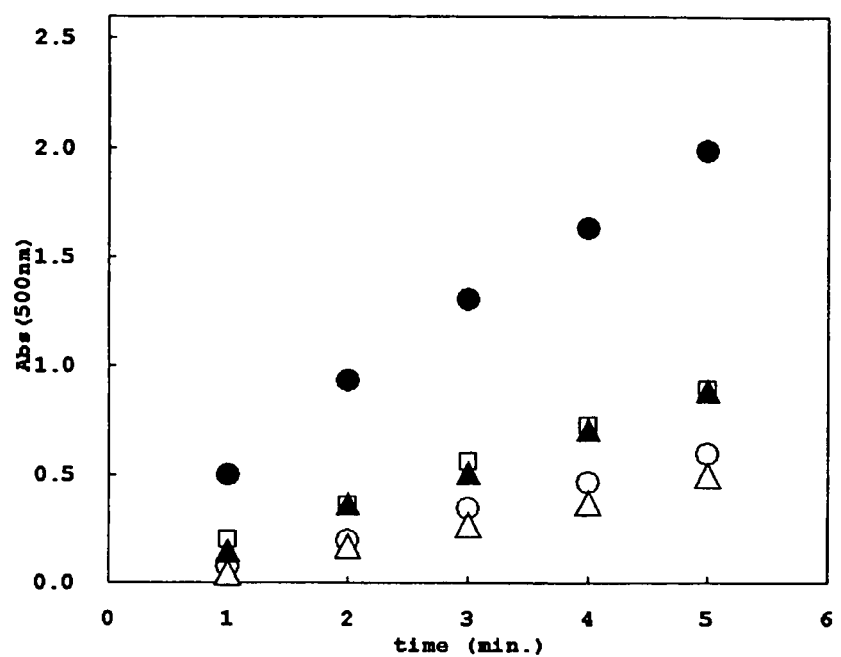

Also, GST activity measuring solution containing a mixture of 1-chloro-2,4-dinitrobenzene and glutathione was added to aliquots of solubilized fractions of proteins derived from those colonies in which expression of fusion proteins with predicted molecular weights had been confirmed to thereby start a reaction by GST, and determined the initial rate of the reaction by measuring the increase in UV absorbance at 350 nm with a spectrophotometer (FIG. 6) (CDNB assay). It was confirmed that the slopes of the straight lines in the graph are almost in proportion to the amount of relevant fusion protein of interest in the solubilized fraction, and thus it was found possible to carry out a semi-quantitative solubility test with a spectrophotometer.

Independently from the above test, the inventors picked 8 colonies from each plate, performing colony PCR and examined the ratio of plasmids from each clone comprising a gene of interest (i.e., efficiency of subcloning). As a result, it was confirmed that a gene with a correct length predicted from the target gene was integrated at the probability of 37/40 (92.5%).

Two clones were selected from those which were expressing a protein of a correct length, followed by determination and confirmation of the DNA sequences of the plasmids. It was confirmed that the sequences were completely correct and that they were in frame with GST.

The time period required for the entire process of the above operations was about 6 days, showing a significant reduction.

Example 3

Comparison of Efficiency between NcoI Selection and NdeI Selection

Comparative experiments were conducted to examine whether there would be any difference in efficiency between NcoI selection and NdeI selection in the preparation of expression systems for GST fusion proteins linked to protein fragments containing ubiquitin interacting motif (UIM).

A pair of primers for NcoI selection (SEQ ID NOS: 48 and 45) and a pair of primers for NdeI selection (SEQ ID NOS: 48 and 50) were used to amplify by PCR an approx. 200 bp fragment (the sequence of the coding strand is shown in SEQ ID NO: 51) of human Hrs gene comprising UIM sequence from human cDNA. The primers used were appropriately designed so that they comprise a sequence complementary to the cDNA of the relevant gene, a complementary sequence to the stop codon, and GG residues at 5'-end to perform NcoI selection. The primers for NdeI selection were appropriately designed in advance so that they comprise a complementary sequence to the stop codon and ATG residues at 5'-end. The above-described fragment is a 200 bp cDNA corresponding to a novel protein domain and encodes about 70 amino acid residues.

PCR amplification of the fragment was confirmed by electrophoresis. Then, the PCR product was ligated unpurified to dGST-T vector, which was transformed into E. coli .DH5a. The transformed DH5a was liquid cultured overnight without formation of single colonies. Next day, 1-3 μg of plasmid was purified from the resultant culture. This plasmid was digested with restriction enzyme NcoI or NdeI and transformed into an expression host E. coli BL21 (DE3), which was then allowed to form single colonies. Reaction conditions were as follows: 10 units of NcoI or 20 units of NdeI was used per 200 ng of plasmid, at 37° C., for 1 hour for both restriction enzymes. From the plates carrying single colonies, 3 single colonies for each were picked (3×5=15) and liquid cultured in LB medium. When OD reached about 0.5, IPTG was added to give a final concentration of 1 mM, and cells were cultured for another 4 hours (expression experiment). E. coli cells after completion of expression were harvested and sonicated. Then, the total cell, solubilized fraction and insolubilized fraction were analyzed by SDS-PAGE, followed by confirmation of the band of the fusion protein of interest (approx. 31 kD) on the gel. In the thus obtained colonies, the ratios of those colonies which expressed a fusion protein of interest with a predicted molecular weight were 14/15 when NcoI selection was used and 3/3 when NdeI selection was used, respectively. In both cases, the ratio was more than about 90% more than (14/15), showing extremely high efficiency.

Independently from the above experiment, the inventors picked several colonies from each plate, performing colony PCR and examined the ratio of plasmids in each clone comprising a gene of interest (i.e., efficiency of subcloning). As a result, it was confirmed that a gene with a correct length predicted from the target gene was integrated at the probability of 9/10 (90.0%) when NcoI selection was used and at the probability of 7/8 (88%) when NdeI selection was used; thus, the efficiency was almost equal.

From these experiments, it was found that both NcoI and NdeI may be used for the selection of ORF orientation.

Example 4

Method of Testing in a Short Period of Time the Expression Level in *E. coli* and Solubility of Fusion Proteins Prepared with dGST-T Vector (FIG. 7)

Using approx. 0.2 µg of mixture of the open circular vector prepared in Example 2 (which had human Vps4b gene integrated thereinto and underwent ORF selection by NcoI treatment), conditions for performing in a short period of time expression test and solubility test on the GST-Vps4 fusion protein (a gene of which was believed to have been constructed in that vector) were determined.

Figure 8:
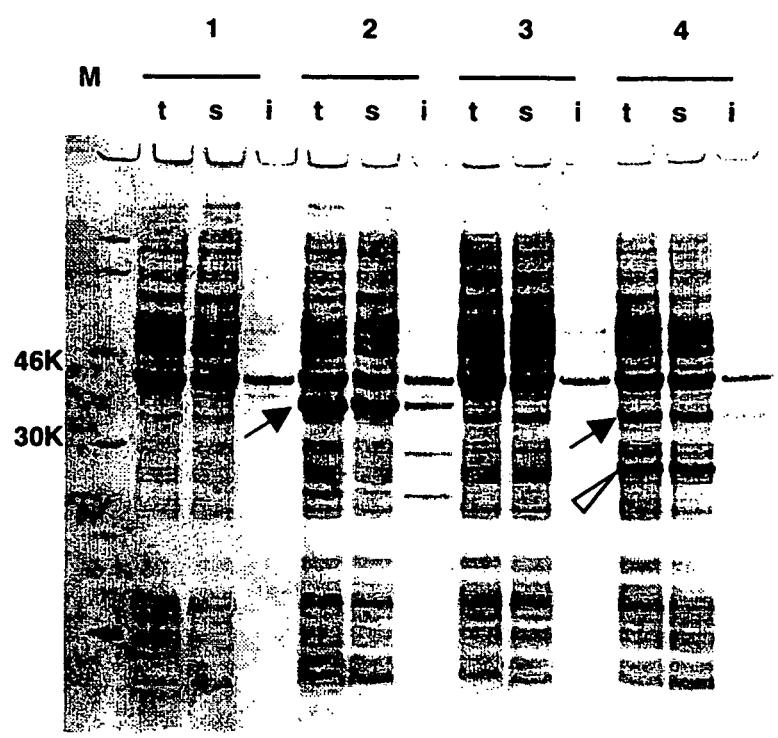
FIG. 8 shows the results of solubility test. Briefly, cDNA fragments encoding the domains of mVps4b and mSNX15a, respectively, are integrated into pGST-4T3-PRESTAT by TA-cloning. After ORF selection with NcoI, colonies formed on agar medium were subjected to expression induction on agar medium without allowing formation of single colonies. Lane M represents molecular weight standards; lanes t1, s1 and i1 represent GST-mouse Vps4b fusion protein samples without expression induction; lanes t2, s2 and i2 represent GST-mouse Vps4b fusion protein samples with expression induction using IPTG spray; lanes t3, s3 and i3 represent GST-mouse SNX15a fusion protein samples without expression induction; lanes t4, s4 and i4 represent GST-mouse SNX15a fusion protein samples with expression induction using IPTG spray; and "t", "i" and "s" represent total cell, insoluble fraction and soluble fraction, respectively. The arrow marks indicate bands of fusion proteins of which expression was confirmed. Mark Δ indicates the band which was believed to be GST alone.

Briefly, approx. 0.2 µg of the pGEX-4T3-PRESAT comprising human Vsp4b gene and already linearized by NcoI treatment as described in Example 2 was transformed into an expression host *E. coli* BL21 (DE3), which was then allowed to form colonies on LB plate medium at 37° C. over 14 hours. Onto this plate, 200 µl of 0.1 M IPTG solution was sprayed. Colonies were grown further at 37° C. for 3 hours to thereby allow protein expression on the plate. To the *E. coli* colonies on the plate, 180 µl of 20 mM Tris-HCl buffer containing 0.15 M NaCl (pH 7.0)(hereinafter, called TBS buffer) was added to prepare suspension. The cells were sonicated to prepare the total cell fraction, solubilized fraction and insolubilized fraction, followed by analysis by SDS-PAGE in the same manner as in Example 2 (FIG. 8). The time required from the suspending of *E. coli* to analysis by SDS-PAGE was about 3 hours.

Like in Example 2, the band of the fusion protein of interest with a molecular weight of approx. 32 kDa was also confirmed in this method. It was revealed that the expression level and solubility of this protein were sufficient for subsequent experiments.

In this experiment, *E. coli* comprising a gene of the fusion protein of interest was subjected to expression test and solubility test as it was (i.e., as a mixture) without the step of single colony formation. However, as shown in Example 2, when ORF selection with NcoI has been performed, *E. coli* cells not comprising the gene of the fusion protein of interest are less than 10% of the *E. coli* cells forming colonies on the plate medium. Thus, it was found possible to judge the expression level and solubility by expression test and solubility test using electrophoresis.

The time period required for the entire process of the above operations is about 21 hours, showing a significant reduction. The time period required for the preceding steps from PCR to ORF selection with NcoI is 27 hours at the minimum. Thus, it was revealed that the entire process for constructing single protein and/or protein domain expression systems and performing solubility test can be done in 48 hours at the minimum.

The designations of the vectors prepared by the present inventors, the designations of commercial plasmids based on which the vectors were prepared, the designation of tags, first restriction enzymes, second restriction enzymes, linker sequences and references are summarized in the following Table.

TABLE IV

| Designation of Vector | Designation of commericial plasmid used as a base | Designation of tag* | First restriction enzyme | Second restriction enzyme | Linker sequence | Reference |
|---|---|---|---|---|---|---|
| pGEX-4T3-PRESAT | pGEX-4T3 | GST-thrombin cleavage site | AhdI | NcoI NdeI | I | 1, 7 |
| pGEX-3X-PRESAT | pGEX-3X | GST-Factor Xa cleavage site | AhdI | NcoI NdeI | I | 1, 7 |
| pET-Trx-PRESAT | pET-32a | TRX-His6-Factor Xa cleavage site (6xHis tag disclosed as SEQ ID NO: 62) | AhdI | KpnI | II | 2, 3, 8 |
| pET-Hisx6-PRESAT (6xHis tag disclosed as SEQ ID NO: 62) | pET-32a | His6-Factor Xa cleavage site (6xHis tag disclosed as SEQ ID NO: 62) | AhdI | KpnI | II | 8 |
| pET-FLAG-PRESAT | pET-32a | FLAG®-Enterokinase cleavage site | AhdI | AflII | III | 4 |
| pET-LBT-PRESAT | pET-32a | LBT | AhdI | KpnI | II | 5 |
| pET-EGFP-PRESAT | pET-32a | EGFP-His6 (6xHis tag disclosed as SEQ ID NO: 62) | AhdI | KpnI | II | 6 |

*Including the designation of tag and the designation of protease cleavage sequence when the tag and a protein of interest are cleaved.
Abbreviations
GST: glutathione-S-transferase (*Schistosoma japonicum*)
TRX: thioredoxin (*E. coli*)
His6: His-His-His-His-His-His (SEQ ID NO: 62)
LBT: lanthanide binding tag
FLAG (registered trademark): Asp-Tyr-Lys-Asp-Asp-Asp-Asp-Lys (SEQ ID NO: 63)
EGFP: enhanced green fluorescence protein (*Aequorea victoria*)

Linker Sequences (the underlined sequence is the AhdI restriction site)

I (487 bp) description: Trx gene and a part of -PACAP artificial gene
(SEQ ID NO: 59)
GACCATTGGTCCACCTGACTGACGACAGTTTTGACACGGATGTACTCAAA

GCGGACGGGGCGATCCTCGTCGATTTCTGGGCAGAGTGGTGCGGTCCGTG

CAAAATGATCGCCCCGATTCTGGATGAAATCGCTGACGAATATCAGGGCA

AACTGACCGTTGCAAAACTGAACATCGATCAAACCCTGGCACTGCGCCG

-continued

```
AAATATGGCATCCGTGGTATCCCGACTCTGCTGCTGTTCAAAAACGGTGA

AGTGGCGGCAACCAAAGTGGGTGCACTGTCTAAAGGTCAGTTGAAAGAGT

TCCTCGACGCTAACCTGGCCGGTTCTGGTTCTGGCCATATGGCTAGCCAT

CACCACCACCACCACAGCAGCGGCATTGACGGCCGGCATAGCGATGGCAT

CTTTACCGATAGCTATAGCCGCTATCGCAAACAGATGGCGGTGAAAAAGT

ATCTGGCGGCGGTGCTGGGCTAATAAGACCAAATGTC

II (110 bp) description: PACAP artificial gene
                                        (SEQ ID NO: 60)
GACGGTCGGTCTAGCGATGGCATCTTTACCGATAGCTATAGCCGCTATCG

CAAACAGATGGCGGTGAAAAAGTATCTGGCGGCGGTGCTGGGCTAATAA

GACCAATGGTC

III (259 bp) description: human ubiquitin gene
                                        (SEQ ID NO: 61)
GACGATAAGTCTCATATGCAGATTTTCGTGAAAACCCTGACCGGCAAAC

CATCACCCTGGAAGTGGAACCGTCCGACACCATCGAAAACGTTAAAGCGA

AAATCCAGGACAAAGAAGGCATCCCGCCGGATCAGCAGCGTCTGATCTTC

GCGGGCAAACAGCTGGAAGACGGCCGTACCCTGTCCGATTACAACATCCA

GAAAGAATCTACCCTGCACCTGGTGCTGCGTCTGCGTGGCGGCTAATA

GACTTAAGGTC
```

REFERENCES

1. Smith D B, Johnson K S. (1998) Single-step purification of polypeptides expressed in *Escherichia coli* as fusions with glutathione S-transferase. *Gene* 67, 31-40
2. LaVallie, E. R, DiBlasio, E. A, Kovacic, S, Grant, K. L, Schendel, P. F. and McCoy, J. M. (1993) A thioredoxin gene fusion expression system that circumvents inclusion body formation in the *E. coli* cytoplasm. *Bio/Technology* 11, 187-193
3. Novy, R, Berg, J, Yaeger, K, and Mierendorf, R. (1995) *inNovations* 3, 7-9
4. Hopp T P, Prickett K S, Price V, Libby R T, March C J, Cerretti P, Urdal D L, and Conlon P J. (1988) A Short Polypeptide Marker Sequence Useful for Recombinant Protein Identification and Purification. *Biotechnology* 6, 1205-1210
5. Wohnert J, Franz K J, Nitz M, Imperiali B, Schwalbe H. (2003) Protein Alignment by a Coexpressed lanthanide-Binding Tag for the Measurement of Residual Dipor Couplings. *J. Am. Chem. Soc.* 125, 13338-13339
6. Waldo G S, Standish B M, Berendzen J, Terwilliger T C. (1999) Rapid protein-folding assay using green fluorescent protein. *Nat. Biotechnol.* 17, 691-695.
7. Goda N, Tenno T, Takasu H, Hiroaki H, and Shirakawa M. (2004) The PRESAT-vector: Asymmetric T-vector for high-throughput screening of soluble protein domains for structural proteomics. *Protein Science* 13, 652-658
8. Tenno T, Goda N, Tateishi Y, Tochio H, Mishima M, Hayashi H, Shirakawa M, and Hiroaki H. (2004) High-throughput construction method for expression vector of peptides for NMR study suited for isotopic labeling. *Protein Engineering, Design and Selection* 17, 305-314

All the publications, patents and patent applications cited herein are incorporated herein by reference in their entity.

INDUSTRIAL APPLICABILITY

According to the present invention, it has become possible to greatly reduce the time required for the entire process of constructing protein and/or protein domain expression systems and performing solubility test.

Sequence Listing Free Text

<SEQ ID NO: 1>
SEQ ID NO: 1 shows the nucleotide sequence of sequence (I).
<SEQ ID NO: 2>
SEQ ID NO: 2 shows the nucleotide sequence of sequence (II).
<SEQ ID NO: 3>
SEQ ID NO: 3 shows the nucleotide sequence of sequence (III).
<SEQ ID NO: 4>
SEQ ID NO: 4 shows the nucleotide sequence of sequence (IV).
<SEQ ID NO: 5>
SEQ ID NO: 5 shows the nucleotide sequence of sequence (V)<
<SEQ ID NO: 6>
SEQ ID NO: 6 shows the nucleotide sequence of sequence (VI).
<SEQ ID NO: 7>
SEQ ID NO: 7 shows the nucleotide sequence of sequence (VII).
<SEQ ID NO: 8>
SEQ ID NO: 8 shows the nucleotide sequence of sequence (VIII).
<SEQ ID NO: 9>
SEQ ID NO: 9 shows the nucleotide sequence of one example of sequence (IX) (when $N^1$ has one base).
<SEQ ID NO: 10>
SEQ ID NO: 10 shows the nucleotide sequence of one example of sequence (X) (when $N^2$ has one base).
<SEQ ID NO: 11>
SEQ ID NO: 11 shows the nucleotide sequence of one example of sequence (XI) (when $N^1$ has one base).
<SEQ ID NO: 12>
SEQ ID NO: 12 shows the nucleotide sequence of one example of sequence (XII) (when $N^2$ has one base).
<SEQ ID NO: 13>
SEQ ID NO: 13 shows the nucleotide sequence of one example of sequence (XIII) (when $N^1$ has one base).
<SEQ ID NO: 14>
SEQ ID NO: 14 shows the nucleotide sequence of one example of sequence (XIV) (when $N^2$ has one base).
<SEQ ID NO: 15>
SEQ ID NO: 15 shows the nucleotide sequence of one example of sequence (XV) (when $N^3$ has one base).
<SEQ ID NO: 16>
SEQ ID NO: 16 shows the nucleotide sequence of one example of sequence (XVI) (when $N^4$ has one base).
<SEQ ID NO: 17>
SEQ ID NO: 17 shows the nucleotide sequence of one example of sequence (XVII) (when $N^3$ has one base).
<SEQ ID NO: 18>
SEQ ID NO: 18 shows the nucleotide sequence of one example of sequence (XVIII) (when $N^4$ has one base).
<SEQ ID NO: 19>
SEQ ID NO: 19 shows the nucleotide sequence of one example of sequence (XIX) (when $N^3$ has one base).
<SEQ ID NO: 20>
SEQ ID NO: 20 shows the nucleotide sequence of one example of sequence (XX) (when $N^4$ has one base).
<SEQ ID NO: 21>
SEQ ID NO: 21 shows the sequence of the DNA used in site-directed mutagenesis of pGEX-4T3.

<SEQ ID NO: 22>

SEQ ID NO: 22 shows the nucleotide sequence of the front primer used in PCR reaction with pET32aPACAP as a template.

<SEQ ID NO: 23>

SEQ ID NO: 23 shows the nucleotide sequence of the rear primer used in PCR reaction with pET32aPACAP as a template.

<SEQ ID NO: 24>

SEQ ID NO: 24 shows the nucleotide sequence of the rear primer (for NcoI selection) used in PCR reaction with pET32aPACAP as a template.

<SEQ ID NO: 25>

SEQ ID NO: 25 shows the nucleotide sequence of one of the DNA strands of the approx. 500 bp PCR product described in Example 1. The other DNA strand was a complementary strand to this.

<SEQ ID NO: 26>

SEQ ID NO: 26 shows the nucleotide sequence of one of the two DNA strands which are the AhdI linker described in Example 1.

<SEQ ID NO: 27>

SEQ ID NO: 27 shows the nucleotide sequence of the other one of the two DNA strands which are the AhdI linker described in Example 1.

<SEQ ID NO: 28>

SEQ ID NO: 28 shows the nucleotide sequence of an approx. 220 bp fragment (coding strand) of MIT domain-comprising gene (human SNX15a) to be used as a PCR template. Sequences added by primers are not included.

<SEQ ID NO: 29>

SEQ ID NO: 29 shows the amino acid sequence encoded by the approx. 220 bp fragment (coding strand) of MIT domain-comprising gene (human SNX15a) to be used as a PCR template.

<SEQ ID NO: 30>

SEQ ID NO: 30 shows the nucleotide sequence of an approx. 220 bp fragment (coding strand) of MIT domain-comprising gene (mouse SNX15a) to be used as a PCR template. Sequences added by primers are not included.

<SEQ ID NO: 31>

SEQ ID NO: 31 shows the amino acid sequence encoded by the approx. 220 bp fragment (coding strand) of MIT domain-comprising gene (mouse SNX15a) to be used as a PCR template.

<SEQ ID NO: 32>

SEQ ID NO: 32 shows the nucleotide sequence of an approx. 220 bp fragment (coding strand) of MIT domain-comprising gene (yeast Vps4) to be used as a PCR template. Sequences added by primers are not included.

<SEQ ID NO: 33>

SEQ ID NO: 33 shows the amino acid sequence encoded by the approx. 220 bp fragment (coding strand) of MIT domain-comprising gene (yeast Vps4) to be used as a PCR template.

<SEQ ID NO: 34>

SEQ ID NO: 34 shows the nucleotide sequence of an approx. 220 bp fragment (coding strand) of MIT domain-comprising gene (human Vps4b) to be used as a PCR template. Sequences added by primers are not included.

<SEQ ID NO: 35>

SEQ ID NO: 35 shows the amino acid sequence encoded by the approx. 220 bp fragment (coding strand) of MIT domain-comprising gene (human Vps4b) to be used as a PCR template.

<SEQ ID NO: 36>

SEQ ID NO: 36 shows the nucleotide sequence of an approx. 220 bp fragment (coding strand) of MIT domain-comprising gene (mouse Vps4b) to be used as a PCR template. Sequences added by primers are not included.

<SEQ ID NO: 37>

SEQ ID NO: 37 shows the amino acid sequence encoded by the approx. 220 bp fragment (coding strand) of MIT domain-comprising gene (mouse Vps4b) to be used as a PCR template.

<SEQ ID NO: 38>

SEQ ID NO: 38 shows the nucleotide sequence of a primer (HSS15F).

<SEQ ID NO: 39>

SEQ ID NO: 39 shows the nucleotide sequence of a primer (HSS15R).

<SEQ ID NO: 40>

SEQ ID NO: 40 shows the nucleotide sequence of a primer (MMS15F).

<SEQ ID NO: 41>

SEQ ID NO: 41 shows the nucleotide sequence of a primer (MMS15R).

<SEQ ID NO: 42>

SEQ ID NO: 42 shows the nucleotide sequence of a primer (ScVPS4F).

<SEQ ID NO: 43>

SEQ ID NO: 43 shows the nucleotide sequence of a primer (ScVPS4R).

<SEQ ID NO: 44>

SEQ ID NO: 44 shows the nucleotide sequence of a primer (HsVPS4F).

<SEQ ID NO: 45>

SEQ ID NO: 45 shows the nucleotide sequence of a primer (HsVPS4R).

<SEQ ID NO: 46>

SEQ ID NO: 46 shows the nucleotide sequence of a primer (MmVPS4F).

<SEQ ID NO: 47>

SEQ ID NO: 47 shows the nucleotide sequence of a primer (MmVPS4R).

Abbreviations: Sc: yeast; Hs: human; Mm: mouse; VPS4: VPS4; S15: SNX15 F: FORWARD; R: REVERSE

<SEQ ID NO: 48>

SEQ ID NO: 48 shows the nucleotide sequence of a primer (HrsF)

<SEQ ID NO: 49>

SEQ ID NO: 49 shows the nucleotide sequence of a primer for NcoI selection (HrsR-Nco).

<SEQ ID NO: 50>

SEQ ID NO: 50 shows the nucleotide sequence of a primer for NdeI selection (HrsR-Nde).

<SEQ ID NO: 51>

SEQ ID NO: 51 shows the nucleotide sequence of an approx. 200 bp fragment (coding strand) of UIM sequence-comprising human Hrs gene to be used as a PCR template. Sequences added by primers are not included.

<SEQ ID NO: 52>

SEQ ID NO: 52 shows the amino acid sequence encoded by the approx. 200 bp fragment (coding strand) of UIM sequence-comprising human Hrs gene to be used as a PCR template.

<SEQ ID NO: 53>

SEQ ID NO: 53 shows the nucleotide sequence of a primer corresponding to the C-terminal of ORF (the protein domain of interest does not include a stop codon) when the first restriction enzyme is AhdI and the second restriction enzyme is NcoI.

<SEQ ID NO: 54>

SEQ ID NO: 54 shows the nucleotide sequence of a primer corresponding to the C-terminal of ORF (the protein domain of interest does not include a stop codon) when the first restriction enzyme is AhdI and the second restriction enzyme is NdeI.

<SEQ ID NO: 55>

SEQ ID NO: 55 shows one example of the nucleotide sequence of $N^1$ in sequences (IX) to (XIV).

<SEQ ID NO: 56>

SEQ ID NO: 56 shows one example of the nucleotide sequence of $N^2$ in sequences (IX) to (XIV).

<SEQ ID NO: 57>

SEQ ID NO: 57 shows one example of the nucleotide sequence of $N^3$ in sequences (XV) to (XX).

<SEQ ID NO: 58>

SEQ ID NO: 58 shows one example of the nucleotide sequence of $N^4$ in sequences (XV) to (XX).

<SEQ ID NO: 59>

SEQ ID NO: 59 shows the nucleotide sequence of linker I.

<SEQ ID NO: 60>

SEQ ID NO: 60 shows the nucleotide sequence of linker II.

<SEQ ID NO: 61>

SEQ ID NO: 61 shows the nucleotide sequence of linker III.

The invention claimed is:

1. A vector comprising:
   two first restriction enzyme recognition sequences different in nucleotide sequence both of which are recognized by a first restriction enzyme,
   wherein one of the first restriction enzyme recognition sequences comprises a part of a second restriction enzyme recognition sequence which is recognized by a second restriction enzyme that is different from the first restriction enzyme, and the other one of the first restriction enzyme recognition sequences does not comprise the part of the second restriction enzyme recognition sequence which is recognized by the second restriction enzyme; and
   a coding region of a specific protein for expressing a fusion protein which includes a protein and/or a protein domain encoded by a foreign gene and the specific protein linked to the protein and/or the protein domain,
   wherein the two first restriction enzyme recognition sequences different in nucleotide sequence are provided downstream of the coding region of the specific protein, one of said first restriction enzyme recognition sequences comprising the part of the second restriction enzyme recognition sequence is located proximal to the coding region of the specific protein, and the other first restriction enzyme recognition sequence not comprising said part of the second restriction enzyme recognition sequence is located distal to the coding region of the specific protein.

2. The vector according to claim 1, wherein the first restriction enzyme is a restriction enzyme which produces a 3'-overhang at the end of the DNA fragments it digested.

3. The vector according to claim 2, wherein the base at the 3'-overhang is thymine.

4. The vector according to claim 1, wherein the first restriction enzyme is selected from the group consisting of AhdI or an isoschizomer thereof, XcmI or an isoschizomer thereof, or a combination thereof.

5. The vector according to claim 4, wherein the first restriction enzyme is selected from the group consisting of AhdI or an isoschizomer thereof, or a combination thereof, and the second restriction enzyme is selected from the group consisting of NcoI, DsaI, EcoTI41, NdeI, SfeI, AvaI, SmlI, XhoI, PstI, EcoT22I, PshBI, AccI, ApaLI, PsiI, ScaI, SplI, Bsp107I, Bsp1286I, BspT107I, Bsp1407I, TatI, HgiCI, KpnI, SpeI, BlnI, NheI, XbaI: SspI, EcoRV and isoschizomers thereof.

6. The vector according to claim 1, wherein the two first restriction enzyme recognition sequences different in nucleotide sequence both of which are recognized by the first restriction enzyme are inserted into its multicloning site.

7. The vector according to claim 1, wherein the vector comprises a coding region of glutathione-S-transferase for expressing a protein and/or a protein domain encoded by a foreign gene in the form of a fusion protein linked to glutathione-S-transferase when the foreign gene is integrated in the vector.

8. The vector according to claim 7, wherein glutathione-S-transferase is isolated from a mammal, *Schistosoma japonicum* or *Escherichia coli*.

9. An open circular vector comprising a double-stranded DNA, which is obtained by treating the vector according to claim 1 with the first restriction enzyme.

10. A method of preparing a vector, comprising:
    introducing into a multicloning site of a plasmid, phage, cosmid, PI vector, bacterial artificial chromosome vector or yeast artificial chromosome vector a double-stranded DNA comprising two first restriction enzyme recognition sequences different in nucleotide sequence both of which are recognized by a first restriction enzyme,
    wherein one of the first restriction enzyme recognition sequences comprises a part of a second restriction enzyme recognition sequence which is recognized by a second restriction enzyme that is different from the first restriction enzyme, and the other one of the first restriction enzyme recognition sequences does not comprise said part of the second restriction enzyme recognition sequence which is recognized by the second restriction enzyme;
    reacting the first restriction enzyme recognition sequences with the first restriction enzyme to expose the part of the second restriction enzyme recognition sequence contained in the first restriction enzyme recognition sequence: and
    attaching the part of the second restriction enzyme recognition sequence to a foreign gene, which is configured to complete the second restriction enzyme recognition sequence if inserted in one orientation but not complete the second restriction enzyme recognition sequence if inserted in the opposite orientation.

11. A double-stranded DNA prepared by a process comprising:
    reacting the vector according to claim 1 with the first restriction enzyme to expose the part of the second restriction enzyme recognition sequence contained in the first restriction enzyme recognition sequence.

12. A method of preparing a protein and/or a protein domain encoded by a foreign gene, comprising:
    introducing into a vector a double-stranded DNA comprising two first restriction enzyme recognition sequences different in nucleotide sequence both of which are recognized by a first restriction enzyme,
    wherein one of the first restriction enzyme recognition sequences comprises a part of a second restriction enzyme recognition sequence which is recognized by a second restriction enzyme that is different from the first restriction enzyme, and the other one of the first restriction enzyme recognition sequences does not comprise said part of the second restriction enzyme recognition sequence which is recognized by the second restriction enzyme;
    reacting the first restriction enzyme recognition sequences with the first restriction enzyme to expose the part of the second restriction enzyme recognition sequence contained in the first restriction enzyme recognition sequence;

attaching the part of the second restriction enzyme recognition sequence to the foreign gene, which is configured to complete the second restriction enzyme recognition sequence if inserted in one orientation but not complete the second restriction enzyme recognition sequence if inserted in the opposite orientation;

applying the second restriction enzyme to the vector, wherein when the foreign gene is so oriented to ligate to not produce the second restriction enzyme recognition sequence recognized by the second restriction enzyme, the second restriction enzyme does not digest the vector, and the vector is not linearized and remains circular; but when the foreign gene is so reversibly oriented to ligate to complete the second restriction enzyme recognition sequence recognized by the second restriction enzyme, the second restriction enzyme digests to linearize the vector; and selecting the vector that is unlinearized by transforming a bacterial cell with the vector that remains circular.

* * * * *

SEQUENCE LISTING

```
<160> NUMBER OF SEQ ID NOS: 132

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 1
gacnntnngt c                                                          11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 2
gacnnanngt c                                                          11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 3
gacnnanngt c                                                              11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 4
gacnntnngt c                                                              11

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 5
ccannnntnn nntgg                                                          15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
```

```
<223> OTHER INFORMATION: see specification as filed for detailed
      description of substitutions and preferred embodiments

<400> SEQUENCE: 6
ccannnnann nntgg                                                          15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 7
ccannnnann nntgg                                                          15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 8
ccannnntnn nntgg                                                          15

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
```

-continued

```
<221> NAME/KEY: modified_base
<222> LOCATION: (19)..(20)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 9
gacnntnngt cngacnnann gtc                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (16)..(17)
<223> OTHER INFORMATION: a, c, g, t, unknown or other
<220> FEATURE:
<221> NAME/KEY: modified_base
<222> LOCATION: (19)..(20)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 10
gacnntnngt cngacnnann gtc                                              23

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (20)..(23)
<223> OTHER INFORMATION: a, c, g, t, unknown or other
<220> FEATURE:
<221> NAME/KEY: modified_base
<222> LOCATION: (25)..(28)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 11
```
ccannnntnn nntggnccan nnnannnntg g                              31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (20)..(23)
<223> OTHER INFORMATION: a, c, g, t, unknown or other
<220> FEATURE:
<221> NAME/KEY: modified_base
<222> LOCATION: (25)..(28)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 12
ccannnntnn nntggnccan nnnannnntg g                              31

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (7)..(8)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (16)..(19)
<223> OTHER INFORMATION: a, c, g, t, unknown or other
<220> FEATURE:
<221> NAME/KEY: modified_base
<222> LOCATION: (21)..(24)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 13
gacnntnngt cnccannnna nnnntgg                                   27

<210> SEQ ID NO 14
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
<220> FEATURE:
<221> NAME/KEY: modified_base
<222> LOCATION: (9)..(12)
<223> OTHER INFORMATION: a, c, g, t, unknown or other
<220> FEATURE:
<221> NAME/KEY: modified_base
<222> LOCATION: (16)..(16)
<223> OTHER INFORMATION: a, c, g, t, unknown or other
<220> FEATURE:
<221> NAME/KEY: modified_base
<222> LOCATION: (20)..(21)
<223> OTHER INFORMATION: a, c, g, t, unknown or other
<220> FEATURE:
<221> NAME/KEY: modified_base
<222> LOCATION: (23)..(24)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 14
ccannnntnn nntggngacn nanngtc                                              27

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 15
nngtcngacn nt                                                              12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (10)..(11)
<223> OTHER INFORMATION: a, c, g, t, unknown or other
<220> FEATURE:
```

```
<223> OTHER INFORMATION: see specification as filed for detailed
      description of substitutions and preferred embodiments

<400> SEQUENCE: 16
nngtcngacn nt                                                              12

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, g, t, unknown or other
<220> FEATURE:
<221> NAME/KEY: modified_base
<222> LOCATION: (8)..(8)
<223> OTHER INFORMATION: a, c, g, t, unknown or other
<220> FEATURE:
<221> NAME/KEY: modified_base
<222> LOCATION: (12)..(15)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 17
nnnntggncc annnnt                                                          16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, g, t, unknown or other
<220> FEATURE:
<221> NAME/KEY: modified_base
<222> LOCATION: (8)..(8)
<223> OTHER INFORMATION: a, c, g, t, unknown or other
<220> FEATURE:
<221> NAME/KEY: modified_base
<222> LOCATION: (12)..(15)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 18
nnnntggncc annnnt                                                          16

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, g, t, unknown or other
<220> FEATURE:
<221> NAME/KEY: modified_base
<222> LOCATION: (8)..(8)
<223> OTHER INFORMATION: a, c, g, t, unknown or other
<220> FEATURE:
```

```
<221> NAME/KEY: modified_base
<222> LOCATION: (12)..(13)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 19
nnnntggnga cnnt                                                              14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (10)..(13)
<223> OTHER INFORMATION: a, c, g, t, unknown or other
<220> FEATURE:
<223> OTHER INFORMATION: see specification as filed for detailed
      description of substitutions and preferred embodiments

<400> SEQUENCE: 20
nngtcncaan nnnt                                                              14

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gttatctaca ccacggggag ccaggcaact atgg                                        34

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggatccgacc attggtccac ctgactgacg acagttttga c                                41

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggatccgacc attggtctta ttagcccagc accgccg                                     37

<210> SEQ ID NO 24
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggatccgaca tttggtctta ttagcccagc accgccg                               37

<210> SEQ ID NO 25
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ggatccgacc attggtccac ctgactgacg acagttttga cacggatgta ctcaaagcgg      60
acggggcgat cctcgtcgat ttctgggcag agtggtgcgg tccgtgcaaa atgatcgccc     120
cgattctgga tgaaatcgct gacgaatatc agggcaaact gaccgttgca aaactgaaca     180
tcgatcaaaa ccctggcact gcgccgaaat atggcatccg tggtatcccg actctgctgc     240
tgttcaaaaa cggtgaagtg gcggcaacca agtgggtgc actgtctaaa ggtcagttga      300
aagagttcct cgacgctaac ctggccggtt ctggttctgg ccatatggct agccatcacc     360
accaccacca cagcagcggc attgacggcc ggcatagcga tggcatcttt accgatagct     420
atagccgcta tcgcaaacag atggcggtga aaaagtatct ggcggcggtg ctgggctaat     480
aagaccaaat gtcggatcc                                                  499

<210> SEQ ID NO 26
<211> LENGTH: 493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gatccgacca ttggtccacc tgactgacga cagttttgac acggatgtac tcaaagcgga      60
cggggcgatc ctcgtcgatt tctgggcaga gtggtgcggt ccgtgcaaaa tgatcgcccc     120
gattctggat gaaatcgctg acgaatatca gggcaaactg accgttgcaa aactgaacat     180
cgatcaaaac cctggcactg cgccgaaata tggcatccgt ggtatcccga ctctgctgct     240
gttcaaaaac ggtgaagtgg cggcaaccaa agtgggtgca ctgtctaaag gtcagttgaa     300
agagttcctc gacgctaacc tggccggttc tggttctggc catatggcta gccatcacca     360
ccaccaccac agcagcggca ttgacggccg gcatagcgat ggcatctttt accgatagcta    420 tagccgctat cgcaaacaga tggcggtgaa aaagtatctg gcggcggtgc tgggctaata     480
agaccaaatg tcg                                                        493

<210> SEQ ID NO 27
<211> LENGTH: 493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
```

```
gatccgacat ttggtcttat tagcccagca ccgccgccag atactttttc accgccatct      60
gtttgcgata gcggctatag ctatcggtaa agatgccatc gctatgccgg ccgtcaatgc     120
cgctgctgtg gtggtggtgg tgatggctag ccatatggcc agaaccagaa ccggccaggt     180
tagcgtcgag gaactctttc aactgacctt tagacagtgc acccactttg gttgccgcca     240
cttcaccgtt tttgaacagc agcagagtcg ggataccacg gatgccatat tcggcgcag      300 tgccagggtt ttgatcgatg ttcagttttg caacggtcag tttgccctga tattcgtcag     360
cgatttcatc cagaatcggg gcgatcattt tgcacggacc gcaccactct gcccagaaat     420
cgacgaggat cgccccgtcc gctttgagta catccgtgtc aaaactgtcg tcagtcaggt     480
ggaccaatgg tcg                                                        493

<210> SEQ ID NO 28
<211> LENGTH: 234
<212> TYPE: DNA
<213> ORGANISM: Homo sapiens
<220> FEATURE:
<221> NAME/KEY: CDS
<222> LOCATION: (1)..(234)

<400> SEQUENCE: 28 acc cct gcc tac cta agc cag gcc aca gag ctc atc acc cag gcc ctg       48
Thr Pro Ala Tyr Leu Ser Gln Ala Thr Glu Leu Ile Thr Gln Ala Leu
1               5                   10                  15 cgg gat gag aag gca ggc gct tac gct gct gca ctc cag ggc tat cga       96
Arg Asp Glu Lys Ala Gly Ala Tyr Ala Ala Ala Leu Gln Gly Tyr Arg
            20                  25                  30 gac ggc gtg cac gtc ttg ctt cag gga gtc ccc agt gac ccg ttg cct      144
Asp Gly Val His Val Leu Leu Gln Gly Val Pro Ser Asp Pro Leu Pro
        35                  40                  45 gcc cgc cag gaa ggt gtg aag aag aag gca gct gag tac ctg aag cgg      192
Ala Arg Gln Glu Gly Val Lys Lys Lys Ala Ala Glu Tyr Leu Lys Arg
    50                  55                  60 gca gag gag atc ctg cgc ctg cac ctg tct caa ctc cca ccc              234
Ala Glu Glu Ile Leu Arg Leu His Leu Ser Gln Leu Pro Pro
65                  70                  75

<210> SEQ ID NO 29
<211> LENGTH: 78
<212> TYPE: PRT
<213> ORGANISM: Homo sapiens

<400> SEQUENCE: 29

Thr Pro Ala Tyr Leu Ser Gln Ala Thr Glu Leu Ile Thr Gln Ala Leu
1               5                   10                  15

Arg Asp Glu Lys Ala Gly Ala Tyr Ala Ala Ala Leu Gln Gly Tyr Arg
            20                  25                  30

Asp Gly Val His Val Leu Leu Gln Gly Val Pro Ser Asp Pro Leu Pro
        35                  40                  45

Ala Arg Gln Glu Gly Val Lys Lys Lys Ala Ala Glu Tyr Leu Lys Arg
    50                  55                  60

Ala Glu Glu Ile Leu Arg Leu His Leu Ser Gln Leu Pro Pro
65                  70                  75

<210> SEQ ID NO 30
<211> LENGTH: 210
<212> TYPE: DNA
<213> ORGANISM: Mus musculus
<220> FEATURE:
<221> NAME/KEY: CDS
<222> LOCATION: (1)..(210)
```

-continued

```
<400> SEQUENCE: 30 tac ctt ggc cag gcc aca gag ctc atc act caa gcc ctg cgg aat gaa     48
Tyr Leu Gly Gln Ala Thr Glu Leu Ile Thr Gln Ala Leu Arg Asn Glu
1               5                   10                  15 aag gct ggc gcc tac gct gct gct ctc caa ggc tac caa gat ggg gtg     96
Lys Ala Gly Ala Tyr Ala Ala Ala Leu Gln Gly Tyr Gln Asp Gly Val
            20                  25                  30 cac att ctt ctg cag ggt gtc tca ggt gac cca tcc cct gcc cgc cgg    144
His Ile Leu Leu Gln Gly Val Ser Gly Asp Pro Ser Pro Ala Arg Arg
        35                  40                  45 gaa ggt gtg aag aag aag gca gcc gag tac ctg aag cgg gca gag atg    192
Glu Gly Val Lys Lys Lys Ala Ala Glu Tyr Leu Lys Arg Ala Glu Met
    50                  55                  60 ctt cac aca cac ttg ccc                                            210
Leu His Thr His Leu Pro
65                  70

<210> SEQ ID NO 31
<211> LENGTH: 70
<212> TYPE: PRT
<213> ORGANISM: Mus musculus

<400> SEQUENCE: 31

Tyr Leu Gly Gln Ala Thr Glu Leu Ile Thr Gln Ala Leu Arg Asn Glu
1               5                   10                  15

Lys Ala Gly Ala Tyr Ala Ala Ala Leu Gln Gly Tyr Gln Asp Gly Val
            20                  25                  30

His Ile Leu Leu Gln Gly Val Ser Gly Asp Pro Ser Pro Ala Arg Arg
        35                  40                  45

Glu Gly Val Lys Lys Lys Ala Ala Glu Tyr Leu Lys Arg Ala Glu Met
    50                  55                  60

Leu His Thr His Leu Pro
65                  70

<210> SEQ ID NO 32
<211> LENGTH: 212
<212> TYPE: DNA
<213> ORGANISM: Saccharomyces cerevisiae
<220> FEATURE:
<221> NAME/KEY: CDS
<222> LOCATION: (1)..(210)

<400> SEQUENCE: 32 atg agc acg gga gat ttt tta act aag gga ata gaa ctg gtt caa aag     48
Met Ser Thr Gly Asp Phe Leu Thr Lys Gly Ile Glu Leu Val Gln Lys
1               5                   10                  15 gcc att gac ctg gac aca gcc acg cag tat gag gag gcg tat aca tca     96
Ala Ile Asp Leu Asp Thr Ala Thr Gln Tyr Glu Glu Ala Tyr Thr Ser
            20                  25                  30 tac tat aac gga tta gat tat ttg atg ttg gct ttg aaa tac gag aaa    144
Tyr Tyr Asn Gly Leu Asp Tyr Leu Met Leu Ala Leu Lys Tyr Glu Lys
        35                  40                  45 aac cct aag tcg aag gat ttg ata aga gcg aag ttt aca gag tat cta    192
Asn Pro Lys Ser Lys Asp Leu Ile Arg Ala Lys Phe Thr Glu Tyr Leu
    50                  55                  60 aac cgt gca gag cag ttg aa                                         212
Asn Arg Ala Glu Gln Leu
65                  70

<210> SEQ ID NO 33
<211> LENGTH: 70
```

```
<212> TYPE: PRT
<213> ORGANISM: Saccharomyces cerevisiae

<400> SEQUENCE: 33

Met Ser Thr Gly Asp Phe Leu Thr Lys Gly Ile Glu Leu Val Gln Lys
1               5                   10                  15

Ala Ile Asp Leu Asp Thr Ala Thr Gln Tyr Glu Ala Tyr Thr Ser
            20                  25                  30

Tyr Tyr Asn Gly Leu Asp Tyr Leu Met Leu Ala Leu Lys Tyr Glu Lys
                35                  40                  45

Asn Pro Lys Ser Lys Asp Leu Ile Arg Ala Lys Phe Thr Glu Tyr Leu
    50                  55                  60

Asn Arg Ala Glu Gln Leu
65              70

<210> SEQ ID NO 34
<211> LENGTH: 231
<212> TYPE: DNA
<213> ORGANISM: Homo sapiens
<220> FEATURE:
<221> NAME/KEY: CDS
<222> LOCATION: (1)..(231)

<400> SEQUENCE: 34 atg tca tcc act tcg ccc aac ctc cag aaa gcg ata gat ctg gct agc      48
Met Ser Ser Thr Ser Pro Asn Leu Gln Lys Ala Ile Asp Leu Ala Ser
1               5                   10                  15 aaa gca gcg caa gaa gac aag gct ggg aac tac gaa gaa gcc ctt cag      96
Lys Ala Ala Gln Glu Asp Lys Ala Gly Asn Tyr Glu Glu Ala Leu Gln
            20                  25                  30 ctc tat cag cat gct gtg cag tat ttt ctt cat gtc gtt aaa tat gaa    144
Leu Tyr Gln His Ala Val Gln Tyr Phe Leu His Val Val Lys Tyr Glu
        35                  40                  45 gca cag ggt gat aaa gcc aag caa agt atc agg gca aag tgt aca gaa    192
Ala Gln Gly Asp Lys Ala Lys Gln Ser Ile Arg Ala Lys Cys Thr Glu
    50                  55                  60 tat ctt gat aga gca gaa aaa cta aag gag tac ctg aaa                231
Tyr Leu Asp Arg Ala Glu Lys Leu Lys Glu Tyr Leu Lys
65                  70                  75

<210> SEQ ID NO 35
<211> LENGTH: 77
<212> TYPE: PRT
<213> ORGANISM: Homo sapiens

<400> SEQUENCE: 35

Met Ser Ser Thr Ser Pro Asn Leu Gln Lys Ala Ile Asp Leu Ala Ser
1               5                   10                  15

Lys Ala Ala Gln Glu Asp Lys Ala Gly Asn Tyr Glu Glu Ala Leu Gln
            20                  25                  30

Leu Tyr Gln His Ala Val Gln Tyr Phe Leu His Val Val Lys Tyr Glu
        35                  40                  45

Ala Gln Gly Asp Lys Ala Lys Gln Ser Ile Arg Ala Lys Cys Thr Glu
    50                  55                  60

Tyr Leu Asp Arg Ala Glu Lys Leu Lys Glu Tyr Leu Lys
65                  70                  75

<210> SEQ ID NO 36
<211> LENGTH: 231
<212> TYPE: DNA
<213> ORGANISM: Mus musculus
<220> FEATURE:
```

```
<221> NAME/KEY: CDS
<222> LOCATION: (1)..(231)

<400> SEQUENCE: 36 atg gcg tcc acg aac acc aac ctg cag aaa gca ata gat ctt gca agc      48
Met Ala Ser Thr Asn Thr Asn Leu Gln Lys Ala Ile Asp Leu Ala Ser
1               5                   10                  15 aaa gca gcc cag gaa gac aaa gct ggg aac tat gag gaa gct ctt caa      96
Lys Ala Ala Gln Glu Asp Lys Ala Gly Asn Tyr Glu Glu Ala Leu Gln
            20                  25                  30 ctc tac caa cat gct gtg cag tat ttt ctc cat gtt gtt aaa tat gaa     144
Leu Tyr Gln His Ala Val Gln Tyr Phe Leu His Val Val Lys Tyr Glu
        35                  40                  45 gca caa ggt gat aaa gcc aag caa agt atc agg gcc aag tgt aca gaa     192
Ala Gln Gly Asp Lys Ala Lys Gln Ser Ile Arg Ala Lys Cys Thr Glu
    50                  55                  60 tat ctc gat aga gca gaa aaa cta aag gaa tat ctg aag                 231
Tyr Leu Asp Arg Ala Glu Lys Leu Lys Glu Tyr Leu Lys
65                  70                  75

<210> SEQ ID NO 37
<211> LENGTH: 77
<212> TYPE: PRT
<213> ORGANISM: Mus musculus

<400> SEQUENCE: 37

Met Ala Ser Thr Asn Thr Asn Leu Gln Lys Ala Ile Asp Leu Ala Ser
1               5                   10                  15

Lys Ala Ala Gln Glu Asp Lys Ala Gly Asn Tyr Glu Glu Ala Leu Gln
            20                  25                  30

Leu Tyr Gln His Ala Val Gln Tyr Phe Leu His Val Val Lys Tyr Glu
        35                  40                  45

Ala Gln Gly Asp Lys Ala Lys Gln Ser Ile Arg Ala Lys Cys Thr Glu
    50                  55                  60

Tyr Leu Asp Arg Ala Glu Lys Leu Lys Glu Tyr Leu Lys
65                  70                  75

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
acccctgcct acctaagcca g                                              21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggattacagg tgcaggcgca gg                                             22

<210> SEQ ID NO 40
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 40
taccttggcc aggccacag                                                    19

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggattagggc aagtgtgtgt gaagc                                             25

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atgagcacgg gagatttttt aactaag                                           27

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggattattcc aagtgctttt tcaactgctc                                        30

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atgtcatcca cttcgccc                                                     18

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggattatttc aggtactcct ttagtttttc tgctc                                  35

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 46
atggcgtcca cgaacacc                                                        18

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggattacttc agatattcct ttagtttttc tgctctatc                                  39

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agggacgaga cggccc                                                          16

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggattaaggt gaagagtaca ggctgctg                                             28

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgattaagg tgaagagtac aggctgctg                                            29

<210> SEQ ID NO 51
<211> LENGTH: 190
<212> TYPE: DNA
<213> ORGANISM: Homo sapiens
<220> FEATURE:
<221> NAME/KEY: CDS
<222> LOCATION: (1)..(189)

<400> SEQUENCE: 51 aag agg gac gag acg gcc ctg cag gag gag gag gag ctg cag ctg gcc            48
Lys Arg Asp Glu Thr Ala Leu Gln Glu Glu Glu Glu Leu Gln Leu Ala
1               5                   10                  15 ctg gcg ctg tca cag tca gag gcg gag gag aag gag agg ctg aga cag            96
Leu Ala Leu Ser Gln Ser Glu Ala Glu Glu Lys Glu Arg Leu Arg Gln
            20                  25                  30 aag tcc acg tac act tcg tac ccc aag gcg gag ccc atg ccc tcg gcc           144
Lys Ser Thr Tyr Thr Ser Tyr Pro Lys Ala Glu Pro Met Pro Ser Ala
        35                  40                  45
```

```
tcc tca gcg ccc ccc gcc agc agc ctg tac tct tca cct gtg aac t      190
Ser Ser Ala Pro Pro Ala Ser Ser Leu Tyr Ser Ser Pro Val Asn
    50                  55                  60
```

<210> SEQ ID NO 52
<211> LENGTH: 63
<212> TYPE: PRT
<213> ORGANISM: Homo sapiens

<400> SEQUENCE: 52

```
Lys Arg Asp Glu Thr Ala Leu Gln Glu Glu Glu Leu Gln Leu Ala
1               5                   10                  15

Leu Ala Leu Ser Gln Ser Glu Ala Glu Glu Lys Glu Arg Leu Arg Gln
            20                  25                  30

Lys Ser Thr Tyr Thr Ser Tyr Pro Lys Ala Glu Pro Met Pro Ser Ala
        35                  40                  45

Ser Ser Ala Pro Pro Ala Ser Ser Leu Tyr Ser Ser Pro Val Asn
    50                  55                  60
```

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(7)
<223> OTHER INFORMATION: a, c, g, t, unknown or other

<400> SEQUENCE: 53 ggnnnnntta                                                          10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 54 atgnnnntta                                                          10

<210> SEQ ID NO 55
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
cacctgactg acgacagttt tgacacggat gtactcaaag cggacggggc gatcctcgtc    60
gatttctggg cagagtggtg cggtccgtgc aaaatgatcg ccccgattct ggatgaaatc   120
gctgacgaat atcagggcaa actgaccgtt gcaaaactga acatcgatca aaaccctggc   180
actgcgccga atatggcat ccgtggtatc ccgactctgc tgctgttcaa aacggtgaa    240 gtggcggcaa ccaaagtggg tgcactgtct aaggtcagt tgaaagagtt cctcgacgct   300
aacctggccg ttctggttc tggccatatg gctagccatc accaccacca ccacagcagc   360
```

```
ggcattgacg gccggcatag cgatggcatc tttaccgata gctatagccg ctatcgcaaa    420
cagatggcgg tgaaaaagta tctggcggcg gtgctgggct aataa                    465

<210> SEQ ID NO 56
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ttattagccc agcaccgccg ccagatactt tttcaccgcc atctgtttgc gatagcggct     60
atagctatcg gtaaagatgc catcgctatg ccggccgtca atgccgctgc tgtggtggtg   120
gtggtgatgg ctagccatat ggccagaacc agaaccggcc aggttagcgt cgaggaactc   180
tttcaactga cctttagaca gtgcacccac tttggttgcc gccacttcac cgttttttgaa  240 cagcagcaga gtcgggatac cacggatgcc atatttcggc gcagtgccag ggttttgatc   300
gatgttcagt tttgcaacgg tcagtttgcc ctgatattcg tcagcgattt catccagaat   360
cggggcgatc attttgcacg gaccgcacca ctctgcccag aaatcgacga ggatcgcccc   420
gtccgctttg agtacatccg tgtcaaaact gtcgtcagtc aggtg                    465

<210> SEQ ID NO 57
<211> LENGTH: 4974
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ggatccccga attcccgggt cgactcgagc ggccgcatcg tgactgactg acgatctgcc     60
tcgcgcgttt cggtgatgac ggtgaaaacc tctgacacat gcagctcccg gagacggtca   120
cagcttgtct gtaagcggat gccgggagca gacaagcccg tcagggcgcg tcagcgggtg   180
ttggcgggtg tcggggcgca gccatgaccc agtcacgtag cgatagcgga gtgtataatt   240
cttgaagacg aaagggcctc gtgatacgcc tatttttata ggttaatgtc atgataataa   300
tggtttctta gacgtcaggt ggcactttc ggggaaatgt gcgcggaacc cctatttgtt   360
tatttttcta aatacattca aatatgtatc cgctcatgag acaataaccc tgataaatgc   420
ttcaataata ttgaaaaagg aagagtatga gtattcaaca tttccgtgtc gcccttattc   480 cctttttttgc ggcattttgc cttcctgttt ttgctcaccc agaaacgctg gtgaaagtaa   540
aagatgctga agatcagttg ggtgcacgag tgggttacat cgaactggat ctcaacagcg   600
gtaagatcct tgagagtttt cgccccgaag aacgttttcc aatgatgagc acttttaaag   660
ttctgctatg tggcgcggta ttatcccgtg ttgacgccgg gcaagagcaa ctcggtcgcc   720
gcatacacta ttctcagaat gacttggttg agtactcacc agtcacagaa aagcatctta   780
cggatggcat gacagtaaga gaattatgca gtgctgccat aaccatgagt gataacactg   840
cggccaactt acttctgaca acgatcggag gaccgaagga gctaaccgct ttttgcaca   900 acatggggga tcatgtaact cgccttgatc gttgggaacc ggagctgaat gaagccatac   960
caaacgacga gcgtgacacc acgatgcctg cagcaatggc aacaacgttg cgcaaactat  1020
taactggcga actacttact ctagcttccc ggcaacaatt aatagactgg atggaggcgg  1080
ataaagttgc aggaccactt ctgcgctcgg cccttccggc tggctggttt attgctgata  1140
```

-continued

```
aatctggagc cggtgagcgt gggtctcgcg gtatcattgc agcactgggg ccagatggta    1200
agccctcccg tatcgtagtt atctacacca cggggagcca ggcaactatg gatgaacgaa    1260
atagacagat cgctgagata ggtgcctcac tgattaagca ttggtaactg tcagaccaag    1320
tttactcata tatactttag attgatttaa aacttcattt ttaatttaaa aggatctagg    1380
tgaagatcct ttttgataat ctcatgacca aaatccctta acgtgagttt tcgttccact    1440
gagcgtcaga ccccgtagaa aagatcaaag gatcttcttg agatcctttt tttctgcgcg    1500
taatctgctg cttgcaaaca aaaaaaccac cgctaccagc ggtggtttgt ttgccggatc    1560
aagagctacc aactctttt ccgaaggtaa ctggcttcag cagagcgcag ataccaaata    1620
ctgtccttct agtgtagccg tagttaggcc accacttcaa gaactctgta gcaccgccta    1680
catacctcgc tctgctaatc ctgttaccag tggctgctgc cagtggcgat aagtcgtgtc    1740
ttaccgggtt ggactcaaga cgatagttac cggataaggc gcagcggtcg ggctgaacgg    1800
ggggttcgtg cacacagccc agcttggagc gaacgaccta caccgaactg agatacctac    1860
agcgtgagct atgagaaagc gccacgcttc ccgaagggag aaaggcggac aggtatccgg    1920
taagcggcag ggtcggaaca ggagagcgca cgagggagct tccaggggga aacgcctggt    1980
atctttatag tcctgtcggg tttcgccacc tctgacttga gcgtcgattt ttgtgatgct    2040
cgtcaggggg gcggagccta tggaaaaacg ccagcaacgc ggccttttta cggttcctgg    2100
ccttttgctg gccttttgct cacatgttct ttcctgcgtt atcccctgat tctgtggata    2160
accgtattac cgcctttgag tgagctgata ccgctcgccg cagccgaacg accgagcgca    2220
gcgagtcagt gagcgaggaa gcggaagagc gcctgatgcg gtattttctc cttacgcatc    2280
tgtgcggtat ttcacaccgc ataaattccg acaccatcga atggtgcaaa acctttcgcg    2340
gtatggcatg atagcgcccg gaagagagtc aattcagggt ggtgaatgtg aaaccagtaa    2400
cgttatacga tgtcgcagag tatgccggtg tctcttatca gaccgtttcc cgcgtggtga    2460
accaggccag ccacgtttct gcgaaaacgc gggaaaaagt ggaagcggcg atggcggagc    2520
tgaattacat tcccaaccgc gtggcacaac aactggcggg caaacagtcg ttgctgattg    2580
gcgttgccac ctccagtctg gccctgcacg cgccgtcgca aattgtcgcg gcgattaaat    2640
ctcgcgccga tcaactgggt gccagcgtgg tggtgtcgat ggtagaacga agcggcgtcg    2700
aagcctgtaa agcggcggtg cacaatcttc tcgcgcaacg cgtcagtggg ctgatcatta    2760
actatccgct ggatgaccag gatgccattg ctgtggaagc tgcctgcact aatgttccgg    2820 cgttattct tgatgtctct gaccagacac ccatcaacag tattatttc tcccatgaag    2880 acggtacgcg actgggcgtg gagcatctgg tcgcattggg tcaccagcaa atcgcgctgt    2940
tagcgggccc attaagttct gtctcggcgc gtctgcgtct ggctggctgg cataaatatc    3000
tcactcgcaa tcaaattcag ccgatagcgg aacgggaagg cgactggagt gccatgtccg    3060
gttttcaaca aaccatgcaa atgctgaatg agggcatcgt tcccactgcg atgctggttg    3120
ccaacgatca gatggcgctg ggcgcaatgc gcgccattac cgagtccggg ctgcgcgttg    3180
gtgcggatat ctcggtagtg ggatacgacg ataccgaaga cagctcatgt tatatcccgc    3240
cgttaaccac catcaaacag gattttcgcc tgctggggca aaccagcgtg gaccgcttgc    3300
tgcaactctc tcagggccag gcggtgaagg gcaatcagct gttgcccgtc tcactggtga    3360
aaagaaaaac caccctggcg cccaatacgc aaaccgcctc tccccgcgcg ttggccgatt    3420
cattaatgca gctggcacga caggtttccc gactggaaag cgggcagtga gcgcaacgca    3480
attaatgtga gttagctcac tcattaggca ccccaggctt tacactttat gcttccggct    3540
```

```
cgtatgttgt gtggaattgt gagcggataa caatttcaca caggaaacag ctatgaccat    3600
gattacggat tcactggccg tcgttttaca acgtcgtgac tgggaaaacc ctggcgttac    3660
ccaacttaat cgccttgcag cacatccccc tttcgccagc tggcgtaata gcgaagaggc    3720
ccgcaccgat cgcccttccc aacagttgcg cagcctgaat ggcgaatggc gctttgcctg    3780
gtttccggca ccagaagcgg tgccggaaag ctggctggag tgcgatcttc ctgaggccga    3840
tactgtcgtc gtcccctcaa actggcagat gcacggttac gatgcgccca tctacaccaa    3900
cgtaacctat cccattacgg tcaatccgcc gtttgttccc acggagaatc cgacgggttg    3960
ttactcgctc acatttaatg ttgatgaaag ctggctacag aaggccaga cgcgaattat    4020
ttttgatggc gttggaatta cgttatcgac tgcacggtgc accaatgctt ctggcgtcag    4080
gcagccatcg gaagctgtgg tatggctgtg caggtcgtaa atcactgcat aattcgtgtc    4140
gctcaaggcg cactcccgtt ctggataatg ttttttgcgc cgacatcata acggttctgg    4200
caaatattct gaaatgagct gttgacaatt aatcatcggc tcgtataatg tgtggaattg    4260
tgagcggata acaatttcac acaggaaaca gtattcatgt cccctatact aggttattgg    4320
aaaattaagg gccttgtgca acccactcga cttcttttgg aatatcttga agaaaaatat    4380
gaagagcatt tgtatgagcg cgatgaaggt gataaatggc gaaacaaaaa gtttgaattg    4440
ggtttggagt ttcccaatct tccttattat attgatggtg atgttaaatt aacacagtct    4500
atggccatca tacgttatat agctgacaag cacaacatgt gggtggttg tccaaaagag    4560
cgtgcagaga tttcaatgct tgaaggagcg gttttggata ttagatacgg tgtttcgaga    4620
attgcatata gtaaagactt tgaaactctc aaagttgatt ttcttagcaa gctacctgaa    4680
atgctgaaaa tgttcgaaga tcgttttatgt cataaaacat atttaaatgg tgatcatgta    4740
acccatcctg acttcatgtt gtatgacgct cttgatgttg ttttatacat ggacccaatg    4800
tgcctggatg cgttcccaaa attagtttgt tttaaaaaac gtattgaagc tatcccacaa    4860
attgataagt acttgaaatc cagcaagtat atagcatggc ctttgcaggg ctggcaagcc    4920
acgtttggtg gtggcgacca tcctccaaaa tcggatctgg ttccgcgtgg atcc          4974
```

<210> SEQ ID NO 58
<211> LENGTH: 4974
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
ggatccacgc ggaaccagat ccgatttttgg aggatggtcg ccaccaccaa acgtggcttg      60
ccagccctgc aaaggccatg ctatatactt gctggatttc aagtacttat caatttgtgg     120
gatagcttca atacgttttt taaaacaaac taattttggg aacgcatcca ggcacattgg     180
gtccatgtat aaaacaacat caagagcgtc atacaacatg aagtcaggat gggttacatg     240
atcaccattt aaatatgttt tatgacataa acgatcttcg aacattttca gcatttcagg     300
tagcttgcta agaaaatcaa ctttgagagt ttcaaagtct ttactatatg caattctcga     360
aacaccgtat ctaatatcca aaccgctcc ttcaagcatt gaaatctctg cacgctcttt     420
tggacaacca cccaacatgt gtgcttgtc agctatataa cgtatgatgg ccatagactg     480
tgttaattta acatcaccat caatataata aggaagattg gaaactcca acccaattc      540
aaactttttg tttcgccatt tatcaccttc atcgcgctca tacaaatgct cttcatattt     600
```

```
ttcttcaaga tattccaaaa gaagtcgagt gggttgcaca aggcccttaa ttttccaata    660
acctagtata ggggacatga atactgtttc ctgtgtgaaa ttgttatccg ctcacaattc    720
cacacattat acgagccgat gattaattgt caacagctca tttcagaata tttgccagaa    780
ccgttatgat gtcggcgcaa aaacattat ccagaacggg agtgcgcctt gagcgacacg     840
aattatgcag tgatttacga cctgcacagc cataccacag cttccgatgg ctgcctgacg    900
ccagaagcat tggtgcaccg tgcagtcgat aacgtaattc caacgccatc aaaaataatt    960
cgcgtctggc cttcctgtag ccagctttca tcaacattaa atgtgagcga gtaacaaccc   1020
gtcggattct ccgtgggaac aaacggcgga ttgaccgtaa tgggataggt tacgttggtg   1080
tagatgggcg catcgtaacc gtgcatctgc cagtttgagg ggacgacgac agtatcggcc   1140
tcaggaagat cgcactccag ccagctttcc ggcaccgctt ctggtgccgg aaaccaggca   1200
aagcgccatt cgccattcag gctgcgcaac tgttgggaag ggcgatcggt gcgggcctct   1260
tcgctattac gccagctggc gaagggggga tgtgctgcaa ggcgattaag ttgggtaacg   1320
ccagggtttt cccagtcacg acgttgtaaa acgacggcca gtgaatccgt aatcatggtc   1380
atagctgttt cctgtgtgaa attgttatcc gctcacaatt ccacacaaca tacgagccgg   1440
aagcataaag tgtaaagcct ggggtgccta atgagtgagc taactcacat taattgcgtt   1500
gcgctcactg cccgctttcc agtcgggaaa cctgtcgtgc cagctgcatt aatgaatcgg   1560
ccaacgcgcg gggagaggcg gtttgcgtat tgggcgccag ggtggttttt cttttcacca   1620
gtgagacggg caacagctga ttgcccttca ccgcctggcc ctgagagagt tgcagcaagc   1680
ggtccacgct ggtttgcccc agcaggcgaa aatcctgttt gatggtggtt aacggcggga   1740
tataacatga gctgtcttcg gtatcgtcgt atcccactac cgagatatcc gcaccaacgc   1800
gcagcccgga ctcggtaatg gcgcgcattg cgcccagcgc catctgatcg ttggcaacca   1860
gcatcgcagt gggaacgatg ccctcattca gcatttgcat ggtttgttga aaaccggaca   1920
tggcactcca gtcgccttcc cgttccgcta tcggctgaat ttgattgcga gtgagatatt   1980
tatgccagcc agccagacgc agacgcgccg agacagaact taatgggccc gctaacagcg   2040
cgatttgctg gtgacccaat gcgaccagat gctccacgcc cagtcgcgta ccgtcttcat   2100
gggagaaaat aatactgttg atgggtgtct ggtcagagac atcaagaaat aacgccggaa   2160
cattagtgca ggcagcttcc acagcaatgg catcctggtc atccagcgga tagttaatga   2220
tcagcccact gacgcgttgc gcgagaagat tgtgcaccgc cgctttacag gcttcgacgc   2280
cgcttcgttc taccatcgac accaccacgc tggcacccag ttgatcggcg cgagatttaa   2340
tcgccgcgac aatttgcgac ggcgcgtgca gggccagact ggaggtggca acgccaatca   2400
gcaacgactg tttgcccgcc agttgttgtg ccacgcggtt gggaatgtaa ttcagctccg   2460
ccatcgccgc ttccactttt tcccgcgttt tcgcagaaac gtggctggcc tggttcacca   2520
cgcgggaaac ggtctgataa gagacaccgg catactctgc gacatcgtat aacgttactg   2580
gtttcacatt caccaccctg aattgactct cttccgggcg ctatcatgcc ataccgcgaa   2640
aggttttgca ccattcgatg gtgtcggaat ttatgcggtg tgaaataccg cacagatgcg   2700
taaggagaaa ataccgcatc aggcgctctt ccgcttcctc gctcactgac tcgctgcgct   2760
cggtcgttcg gctgcggcga gcggtatcag ctcactcaaa ggcggtaata cggttatcca   2820
cagaatcagg ggataacgca ggaaagaaca tgtgagcaaa aggccagcaa aaggccagga   2880
accgtaaaaa ggccgcgttg ctggcgtttt tccataggct ccgcccccct gacgagcatc   2940
acaaaaatcg acgctcaagt cagaggtggc gaaacccgac aggactataa agataccagg   3000
```

```
cgtttccccc tggaagctcc ctcgtgcgct ctcctgttcc gaccctgccg cttaccggat    3060
acctgtccgc ctttctccct tcgggaagcg tggcgctttc tcatagctca cgctgtaggt    3120
atctcagttc ggtgtaggtc gttcgctcca agctgggctg tgtgcacgaa ccccccgttc    3180
agcccgaccg ctgcgcctta tccggtaact atcgtcttga gtccaacccg gtaagacacg    3240
acttatcgcc actggcagca gccactggta acaggattag cagagcgagg tatgtaggcg    3300
gtgctacaga gttcttgaag tggtggccta actacggcta cactagaagg acagtatttg    3360
gtatctgcgc tctgctgaag ccagttacct tcggaaaaag agttggtagc tcttgatccg    3420
gcaaacaaac caccgctggt agcggtggtt ttttgtttg caagcagcag attacgcgca    3480
gaaaaaaagg atctcaagaa gatcctttga tcttttctac ggggtctgac gctcagtgga    3540
acgaaaactc acgttaaggg attttggtca tgagattatc aaaaaggatc ttcacctaga    3600
tccttttaaa ttaaaaatga gttttaaat caatctaaag tatatatgag taaacttggt    3660
ctgacagtta ccaatgctta atcagtgagg cacctatctc agcgatctgt ctatttcgtt    3720
catccatagt tgcctggctc cccgtggtgt agataactac gatacgggag ggcttaccat    3780
ctggccccag tgctgcaatg ataccgcgag acccacgctc accggctcca gatttatcag    3840
caataaacca gccagccgga agggccgagc gcagaagtgg tcctgcaact ttatccgcct    3900
ccatccagtc tattaattgt tgccgggaag ctagagtaag tagttcgcca gttaatagtt    3960
tgcgcaacgt tgttgccatt gctgcaggca tcgtggtgtc acgctcgtcg tttggtatgg    4020
cttcattcag ctccggttcc caacgatcaa ggcgagttac atgatccccc atgttgtgca    4080
aaaaagcggt tagctccttc ggtcctccga tcgttgtcag aagtaagttg gccgcagtgt    4140
tatcactcat ggttatggca gcactgcata attctcttac tgtcatgcca tccgtaagat    4200
gcttttctgt gactggtgag tactcaacca agtcattctg agaatagtgt atgcggcgac    4260
cgagttgctc ttgcccggcg tcaacacggg ataataccgc gccacatagc agaactttaa    4320
aagtgctcat cattggaaaa cgttcttcgg ggcgaaaact ctcaaggatc ttaccgctgt    4380
tgagatccag ttcgatgtaa cccactcgtg cacccaactg atcttcagca tcttttactt    4440
tcaccagcgt ttctgggtga gcaaaaacag gaaggcaaaa tgccgcaaaa aagggaataa    4500
gggcgacacg gaaatgttga atactcatac tcttcctttt tcaatattat tgaagcattt    4560
atcagggtta ttgtctcatg agcggataca tatttgaatg tatttagaaa aataaacaaa    4620
taggggttcc gcgcacattt ccccgaaaag tgccacctga cgtctaagaa accattatta    4680
tcatgacatt aacctataaa aataggcgta tcacgaggcc ctttcgtctt caagaattat    4740
acactccgct atcgctacgt gactgggtca tggctgcgcc ccgacacccg ccaacacccg    4800
ctgacgcgcc ctgacgggct tgtctgctcc cggcatccgc ttacagacaa gctgtgaccg    4860
tctccgggag ctgcatgtgt cagaggtttt caccgtcatc accgaaacgc gcgaggcaga    4920
tcgtcagtca gtcacgatgc ggccgctcga gtcgacccgg gaattcgggg atcc           4974
```

<210> SEQ ID NO 59
<211> LENGTH: 487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gaccattggt ccacctgact gacgacagtt ttgacacgga tgtactcaaa gcggacgggg      60
cgatcctcgt cgatttctgg gcagagtggt gcggtccgtg caaaatgatc gccccgattc     120
```

```
tggatgaaat cgctgacgaa tatcagggca aactgaccgt tgcaaaactg aacatcgatc    180
aaaaccctgg cactgcgccg aaatatggca tccgtggtat cccgactctg ctgctgttca    240
aaaacggtga agtggcggca accaaagtgg gtgcactgtc taaaggtcag ttgaaagagt    300
tcctcgacgc taacctggcc ggttctggtt ctggccatat ggctagccat caccaccacc    360
accacagcag cggcattgac ggccggcata gcgatggcat ctttaccgat agctatagcc    420
gctatcgcaa acagatggcg gtgaaaaagt atctggcggc ggtgctgggc taataagacc    480
aaatgtc                                                              487
```

<210> SEQ ID NO 60
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
gacggtcggt ctagcgatgg catctttacc gatagctata gccgctatcg caaacagatg     60
gcggtgaaaa agtatctggc ggcggtgctg ggctaataag accaatggtc                110
```

<210> SEQ ID NO 61
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gacgataagt ctcatatgca gattttcgtg aaaaccctga ccggcaaaac catcaccctg     60
gaagtggaac cgtccgacac catcgaaaac gttaaagcga aaatccagga caaagaaggc    120
atcccgccgg atcagcagcg tctgatcttc gcgggcaaac agctggaaga cggccgtacc    180
ctgtccgatt acaacatcca gaaagaatct accctgcacc tggtgctgcg tctgcgtggc    240
ggctaataga cttaaggtc                                                 259
```

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 62

His His His His His His
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Tyr Lys Asp Asp Asp Asp Lys
1               5

```
<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gacaaaatgt cggatcc                                              17

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggatccgacc atatgtcgga tcc                                       23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggatccgaca tttggtcgga tcc                                       23

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(16)
<223> OTHER INFORMATION: a, c, g, t, unknown or other

<400> SEQUENCE: 67
ggatccgacc atnnnn                                               16

<210> SEQ ID NO 68
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccatgtcgga tcc                                                  13

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(16)
<223> OTHER INFORMATION: a, c, g, t, unknown or other
```

```
<400> SEQUENCE: 69
ggatccgacc atggnn                                                      16

<210> SEQ ID NO 70
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other

<400> SEQUENCE: 70
nnatgtcgga tcc                                                         13

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gaccattggt c                                                           11

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 72
gacncttggt c                                                           11

<210> SEQ ID NO 73
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gactattggt c                                                           11

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cacaattggt c                                                           11

<210> SEQ ID NO 75
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gacgattggt c                                                              11

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 76
gacnattggt c                                                              11

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gacaaaatgt c                                                              11

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gacatttggt c                                                              11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 79
gacngttggt c                                                              11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (4)..(4)
<223> OTHER INFORMATION: a, c, g, t, unknown or other

<400> SEQUENCE: 80
gacntttggt c                                                          11

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gacagttggt c                                                          11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaccgttggt c                                                          11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gacggttggt c                                                          11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gactgttggt c                                                          11

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gacacttggt c                                                          11

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
                          oligonucleotide

<400> SEQUENCE: 86
gacaaattgt c                                                            11

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gacccttggt c                                                            11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gacgcttggt c                                                            11

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gactcttggt c                                                            11

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ccaataaatg gctgg                                                        15

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 91
ccanccatgg tatgg                                                        15

<210> SEQ ID NO 92
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 92
ccanncatgg tatgg                                                     15

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: a, c, g, t, unknown or other

<400> SEQUENCE: 93
ccannnctgg tatgg                                                     15

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 94
ccanctatgg tatgg                                                     15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 95
ccancaatgg tatgg                                                     15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 96
ccancgatgg tatgg                                                     15
```

```
<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: a, c, g, t, unknown or other

<400> SEQUENCE: 97
ccannnctgg tatgg                                                          15

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccaataaacc gctgg                                                          15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccaataaatg gctgg                                                          15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: a, c, g, t, unknown or other

<400> SEQUENCE: 100
ccannnatgg tatgg                                                          15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 101
ccannattgg tatgg                                                          15

<210> SEQ ID NO 102
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: a, c, g, t, unknown or other

<400> SEQUENCE: 102
ccannngtgg tatgg                                                    15

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: a, c, g, t, unknown or other

<400> SEQUENCE: 103
ccannnttgg tatgg                                                    15

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 104
ccannagtgg tatgg                                                    15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccaataaatg gctgg                                                    15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 106
ccanncgtgg tatgg                                                    15

<210> SEQ ID NO 107
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 107
ccannggtgg tatgg                                                      15

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 108
ccanntgtgg tatgg                                                      15

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 109
ccannactgg tatgg                                                      15

<210> SEQ ID NO 110
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 110
ccanncctgg tatgg                                                      15

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 111
```
ccanngctgg tatgg                                                    15

<210> SEQ ID NO 112
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 112
ccanntctgg tatgg                                                    15

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 113
ccannaatgg tatgg                                                    15

<210> SEQ ID NO 114
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, t, unknown or other

<400> SEQUENCE: 114
ccanngatgg tatgg                                                    15

<210> SEQ ID NO 115
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other

<400> SEQUENCE: 115
ccnaaatggt atgg                                                     14

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)..(4)
<223> OTHER INFORMATION: a, c, g, t, unknown or other

<400> SEQUENCE: 116
ccangaatgg tatgg                                              15

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 117
ccanacatgg tatgg                                              15

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 118
ccangcatgg tatgg                                              15

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 119
ccantcatgg tatgg                                              15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 120
ccanagatgg tatgg                                              15

<210> SEQ ID NO 121
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 121
ccanggatgg tatgg                                                    15

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 122
ccantgatgg tatgg                                                    15

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 123
ccangtatgg tatgg                                                    15

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, g, t, unknown or other

<400> SEQUENCE: 124
ccanttatgg tatgg                                                    15

<210> SEQ ID NO 125
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ccaaacgtgg tatgg                                                    15

<210> SEQ ID NO 126
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ccacacgtgg tatgg                                                    15

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ccagacgtgg tatgg                                                    15

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccatacgtgg tatgg                                                    15

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ccaaagctgg tatgg                                                    15

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccacacctgg tatgg                                                    15

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccagagctgg tatgg                                                    15

<210> SEQ ID NO 132
<211> LENGTH: 18
<212> TYPE: DNA
<213> ORGANISM: Artificial Sequence
```

```
-continued

<220> FEATURE:
<223> OTHER INFORMATION: Description of Artificial Sequence: Synthetic
      oligonucleotide

<400> SEQUENCE: 132
ggatccgacc attggtcc                                                       18
```